(12) United States Patent
Abate-Daga

(10) Patent No.: US 12,083,148 B2
(45) Date of Patent: Sep. 10, 2024

(54) IL13Ra2-BINDING CHIMERIC ANTIGEN RECEPTORS

(71) Applicant: H. LEE MOFFITT CANCER CENTER AND RESEARCH INSTITUTE, INC., Tampa, FL (US)

(72) Inventor: Daniel Abate-Daga, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 938 days.

(21) Appl. No.: 16/487,367

(22) PCT Filed: Feb. 22, 2018

(86) PCT No.: PCT/US2018/019147
§ 371 (c)(1),
(2) Date: Aug. 20, 2019

(87) PCT Pub. No.: WO2018/156711
PCT Pub. Date: Aug. 30, 2018

(65) Prior Publication Data
US 2020/0061114 A1    Feb. 27, 2020

Related U.S. Application Data

(60) Provisional application No. 62/462,054, filed on Feb. 22, 2017.

(51) Int. Cl.
| | | |
|---|---|---|
| *A61K 35/17* | (2015.01) |
| *C07K 14/715* | (2006.01) |
| *C07K 14/725* | (2006.01) |
| *C07K 16/28* | (2006.01) |
| *C12N 5/0783* | (2010.01) |

(52) U.S. Cl.
CPC .......... *A61K 35/17* (2013.01); *C07K 14/7051* (2013.01); *C07K 14/7155* (2013.01); *C07K 16/2866* (2013.01); *C12N 5/0636* (2013.01); *C07K 2317/622* (2013.01); *C07K 2319/03* (2013.01)

(58) Field of Classification Search
CPC ................ A61K 35/17; C07K 14/7051; C07K 14/7155; C07K 16/2866; C12N 5/0636
See application file for complete search history.

(56) References Cited

U.S. PATENT DOCUMENTS

| | | | |
|---|---|---|---|
| 2013/0129753 A1* | 5/2013 | Doroski ............. | A61K 47/6803 530/331 |
| 2013/0336982 A1 | 12/2013 | Mader et al. | |
| 2016/0340649 A1* | 11/2016 | Brown ............... | C07K 14/5437 |

FOREIGN PATENT DOCUMENTS

WO     2016090369 A1    6/2016

OTHER PUBLICATIONS

Krenciute et al. Characterization and functional analysis of scFv-based chimeric antigen receptors to redirect T cells to IL13Rα2-positive glioma. Mol. Ther. 24, 354-363, 2016. (Year: 2016).*
International Search Report and Written Opinion in PCT/US2018/019147. Mailed Jul. 27, 2018. 12 pages.
Kim, JW, et al. A Novel Single-Chain Antibody for Selective Targeting of IL13Ra2-Expressing Brain Tumors. Molecular Therapy. May 2015, vol. 23, Supplement 1; p. S10, Section 22, Background Paragraph; Conclusion Paragraph.

* cited by examiner

*Primary Examiner* — Elly-Gerald Stoica
(74) *Attorney, Agent, or Firm* — Meunier Carlin & Curfman LLC

(57) ABSTRACT

Disclosed herein are chimeric antigen receptor (CAR) polypeptides that can be used with adoptive cell transfer to target and kill IL13Ra2-expressing cancers. Also disclosed are immune effector cells, such as T cells or Natural Killer (NK) cells, that are engineered to express these CARs. Therefore, also disclosed are methods of providing an anti-tumor immunity in a subject with an IL13Ra2-expressing cancer that involves adoptive transfer of the disclosed immune effector cells engineered to express the disclosed CARs.

14 Claims, 5 Drawing Sheets

Specification includes a Sequence Listing.

IL13Ra2-BINDING CHIMERIC ANTIGEN RECEPTORS

CROSS REFERENCE TO RELATED APPLICATION

This application is a national stage application filed under 35 U.S.C. § 371 of International Application No. PCT/US2018/019147, filed on Feb. 22, 2018, which claims the benefit of U.S. Provisional Patent Application Ser. No. 62/462,054, filed Feb. 22, 2017, applications which are fully incorporated herein by reference in their entirety.

STATEMENT REGARDING FEDERALLY SPONSORED RESEARCH OR DEVELOPMENT

This invention was made with Government Support under Grant No. CA168536 awarded by the National Institutes of Health. The Government has certain rights in the invention.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Disclosed herein are chimeric antigen receptor (CAR) polypeptides that can be used with adoptive cell transfer to target and kill IL13Ra2-expressing cancers. The disclosed CAR polypeptides contain in an ectodomain an anti-IL13Ra2 binding agent that can bind IL13Ra2-expressing cancer cells. As with other CARs, the disclosed polypeptides can also contain a transmembrane domain and an endodomain capable of activating an immune effector cell. For example, the endodomain can contain an intracellular signaling domain and optionally one or more co-stimulatory signaling regions.

The anti-IL13Ra2 binding agent is in some embodiments an antibody fragment that specifically binds IL13Ra2. For example, the antigen binding domain can be a Fab or a single-chain variable fragment (scFv) of an antibody that specifically binds IL13Ra2. The anti-IL13Ra2 binding agent is in some embodiments an aptamer that specifically binds IL13Ra2. For example, the anti-IL13Ra2 binding agent can be a peptide aptamer selected from a random sequence pool based on its ability to bind IL13Ra2. The anti-IL13Ra2 binding agent can also be a natural ligand of IL13Ra2, or a variant and/or fragment thereof capable of binding IL13Ra2.

In some cases, the anti-IL13Ra2 $V_H$ domain comprises the amino acid sequence EVQLVESGGGLVQPGGSLRLS-CAASGFTFSRNGMSWVRQAPGKGLEWVATV SSGGSYIYYADSVKGRFTISRDNAKNSLYLQMNSL-RAEDTAVYYCARQGTTA LATRFFDVWGQGTLVTVSS (SEQ ID NO:1), or a fragment or variant thereof able to bind IL13Ra2.

In some cases, the anti-IL13Ra2 $V_H$ domain comprises the amino acid sequence EVQLVESGGGLVQPGGSLRLSCAASGFTFT-KYGVHWVRQAPGKGLEWVAV KWAGGSTDYN-SALMSRFTISRDNAKNSLYLQMNSLRAEDTAVYY-CARDHR DAMDYWGQGTLVTVSS (SEQ ID NO:2), or a fragment or variant thereof able to bind IL13Ra2.

In some cases, the anti-IL13Ra2 $V_H$ domain comprises the amino acid sequence EVQLVESGGGLVQPGGSLRLS-CAASGFTFSRNGMSWVRQTPDKRLEWVATV SSGGSYIYYADSVKGRFTISRDNAKNSLYLQMSSL-RAEDTAVYYCARQGTTA LATRFFDVWGQGTLVTVSS (SEQ ID NO:28), or a fragment or variant thereof able to bind IL13Ra2.

In some cases, the anti-IL13Ra2 $V_L$ domain comprises the amino acid sequence DIQMTQSPSSLSASVGDRVTITCKASQDVGTA-VAWYQQKPGKAPKLLIYSAS YRSTGVPSRFSGSGSGTDFTLTISSLQPEDFA-TYYCQHHYSAPWTFGGGTKVEI K (SEQ ID NO:3), or a fragment or variant thereof able to bind IL13Ra2.

In some cases, the anti-IL13Ra2 $V_L$ domain comprises the amino acid sequence DDIQMTQSPSSLSASVGDRVTITCTASLSVS-STYLHWYQQKPGKAPKLLIYSTS NLASGVPSRFSGSGSGTDFTLTISSLQPEDFATYY-CHQYHRSPLTFGGGTKVEI K (SEQ ID NO:4), or a fragment or variant thereof able to bind IL13Ra2.

In some cases, the anti-IL13Ra2 $V_L$ domain comprises the amino acid sequence DIQMTQSPSSLSASVGDRVTITCKASQDVGTA-VAWYQQIPGKAPKLLIYSASY RSTGVPDRFSGSGSGTDFSFlISSLQPEDFATYYCQHH-YSAPWTFGGGTKVEIK (SEQ ID NO:29), or a fragment or variant thereof able to bind IL13Ra2.

In some embodiments, the anti-IL13Ra2 $V_H$ domain the following CDR domains: CDR1: TKYGVH (SEQ ID NO:16), CDR2: VKWAGGSTDYNSALMS (SEQ ID NO:17), and CDR3: DHRDAMDY (SEQ ID NO:18). In some embodiments, the anti-IL13Ra2 $V_L$T comprises the following CDR domains: CDR1: TASLSVSSTYLH (SEQ ID NO:19), CDR2: SASYRST (SEQ ID NO:20), and CDR3: QHHYSAPWT (SEQ ID NO:21).

In some embodiments, the anti-IL13Ra2 $V_H$ domain the following CDR domains: CDR1: SRNGMS (SEQ ID NO:22), CDR2: TVSSGGSYIYYADSVKG (SEQ ID NO:23), and CDR3: QGTTALATRFFDV (SEQ ID NO:24). In some embodiments, the anti-IL13Ra2 $V_L$T comprises the following CDR domains: CDR1: KASQDVGTAVA (SEQ ID NO:25), CDR2: SASYRST (SEQ ID NO:26), and CDR3: QHHYSAPWT (SEQ ID NO:27).

In some embodiments, the intracellular signaling domain is a CD3 zeta (CD3ζ) signaling domain, and the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules.

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR binds to IL13Ra2.

Also disclosed is a method of providing an anti-tumor immunity in a subject with an IL13Ra2-expressing cancer that involves administering to the subject an effective amount of an immune effector cell genetically modified with a disclosed IL13Ra2-specific CAR. In some aspects, the cancer can be a melanoma (including, for example, melanoma brain metastases).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6A shows the expression of IL13RA2 on the surface of A375 melanoma cells was analyzed by flow cytometry. FIG. 6B shows A375 cells were seeded in an xCELLigence E-plate, and their growth was monitored over time based on the changes in the impedance of the plate resulting from the adherence of tumor cells. After approximately 20 hours, anti-IL13RA2 Hu08-HL CAR-T cells (CAR-T) or control untransduced T cells (UT) were added at the indicated ratios. The viability of tumor cells over time was estimated based on the fraction of adherent cells, and expressed in a relative unit (Normalized Cell Index). A normalized cell index of 1 corresponds to the amount of adherent tumor cells at the moment when T cells were added to the culture. Error bars represent standard deviation of replicates. FIG. 6C shows a bar graph depicting, the normalized cell index at 4, 24, and 48 hours post CAR-T cell administration.

DETAILED DESCRIPTION

Figure 1:
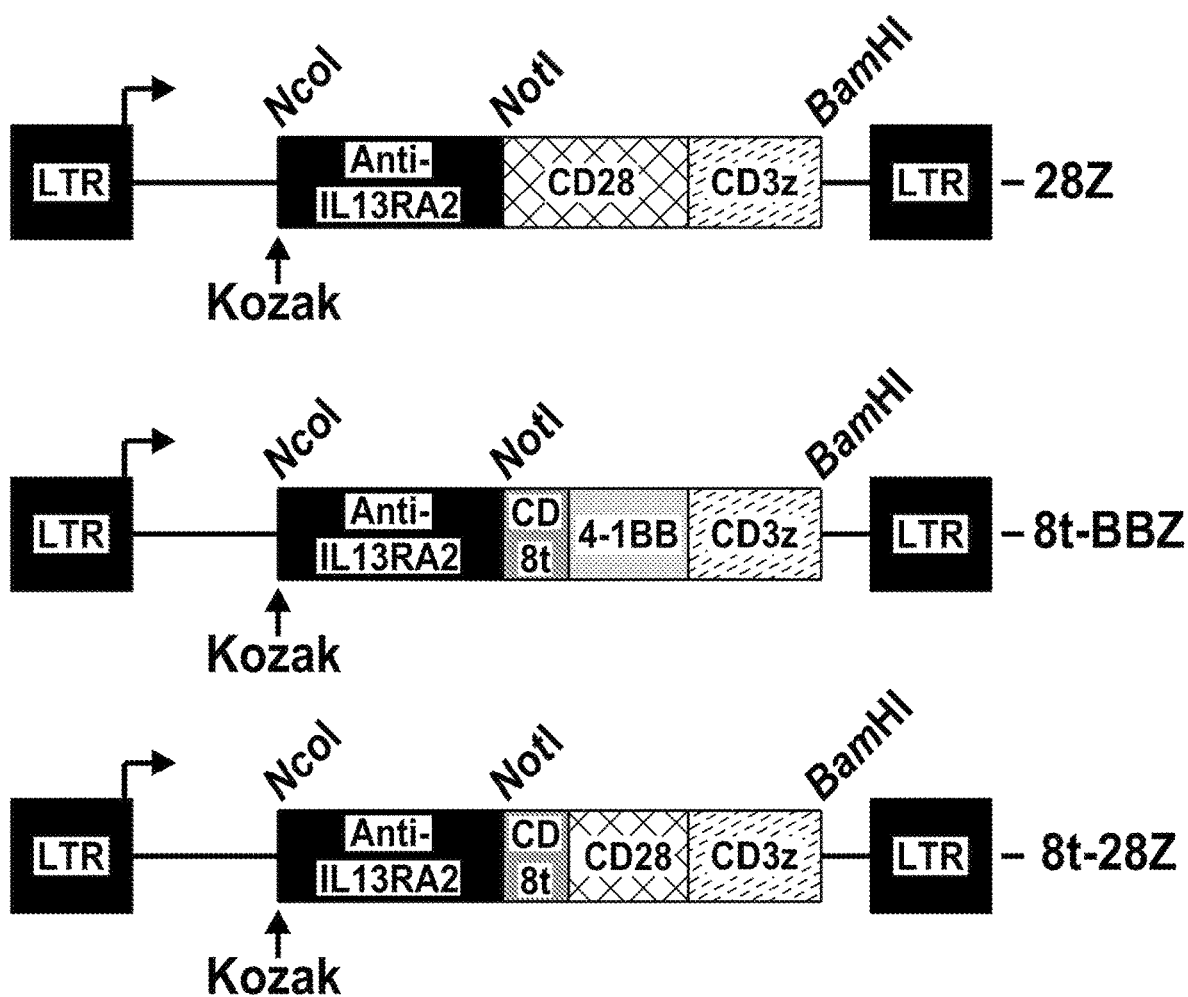
FIG. 1 is an illustration of three embodiments of the disclosed IL13Ra2-specific chimeric antigen receptor (CAR).

Disclosed herein are chimeric antigen receptors (CAR) that can specifically recognize tumor-associated antigens (TAA) on IL13Ra2-expressing cancers. Also disclosed are immune effector cells, such as T cells or Natural Killer (NK) cells, that are engineered to express these CARs. Therefore, also disclosed are methods for providing an anti-tumor immunity in a subject with IL13Ra2-expressing cancers that involves adoptive transfer of the disclosed immune effector cells engineered to express the disclosed IL13Ra2-specific CARs.

IL13Ra2-Specific Chimeric Antigen Receptors (CAR)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is an IL13Ra2-specific chimeric antigen receptor (CAR) that can be that can be expressed in immune effector cells to enhance antitumor activity against IL13Ra2-specific CARs.

The disclosed CAR is generally made up of three domains: an ectodomain, a transmembrane domain, and an endodomain. The ectodomain comprises the IL13Ra2-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR).

In some embodiments, the disclosed CAR is defined by the formula:

SP-IL13Ra2-HG-TM-CSR-ISD;

wherein "SP" represents an optional signal peptide,
wherein "IL13Ra2" represents a IL13Ra2-binding region,
wherein "HG" represents an optional hinge domain,
wherein "TM" represents a transmembrane domain,
wherein "CSR" represents one or more co-stimulatory signaling regions,
wherein "ISD" represents an intracellular signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3 chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements. Thus, specifically contemplated herein are CARs comprising any one or combination of two more co-stimulatory signaling elements for the group consisting of CD27, CD28, 4-1BB (CD137), OX40, CD30, CD40, ICOS, LFA-1, CD2, CD7, LIGHT, NKG2C, B7-H3, and a ligand that specifically binds with CD83, CD8, CD4, b2c, CD80, CD86, DAP10, DAP12, MyD88, BTNL3, and NKG2DCD28 and 4-1BB, CD28 and OX40, CD28 and LFA-1, CD28 and CD40. Thus, for example, specifically contemplated herein are CARs comprising co-stimulatory signaling elements for CD28 and CD40, CD28 and 4-1BB, CD28 and OX40, and CD28 and LFA-1.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-IL13Ra2 scFv) and the transmembrane domain. The hinge sequence can be any suitable sequence derived or obtained from any suitable molecule. In some embodiments, for example, the hinge sequence is derived from a CD8 alpha molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAH-R, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TN1R2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR. In some embodiments, the linker can be a spacer derived from the same source as the transmembrane domain. For example in some instances, the spacer can and the transmembrane domain are both derived from the CD28 or CD8 alpha, or from any other source for the transmembrane domain listed above including, but not limited to, the alpha, beta or zeta chain of the T-cell receptor, CD3 epsilon, CD45, CD4, CD5, CD8 beta, CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. In other embodiments, the transmembrane domain and the liner (such as a spacer) can be derived from different sources, for example, a CD28 transmembrane domain and a CD8 alpha spacer or a CD8 alpha transmembrane domain and a CD28 spacer.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of IL13Ra2-binding region, co-stimulatory signaling regions, and intracellular signaling domain that can occur in the disclosed CARs.

TABLE 1

First Generation CARs

| ScFv | Signal Domain |
|---|---|
| IL13Ra2 | CD8 |
| IL13Ra2 | CD3ζ |
| IL13Ra2 | CD3δ |
| IL13Ra2 | CD3γ |
| IL13Ra2 | CD3ε |
| IL13Ra2 | FcγRI-γ |
| IL13Ra2 | FcγRIII-γ |
| IL13Ra2 | FcεRIβ |
| IL13Ra2 | FcεRIγ |
| IL13Ra2 | DAP10 |
| IL13Ra2 | DAP12 |
| IL13Ra2 | CD32 |
| IL13Ra2 | CD79a |

TABLE 2

Second Generation CARs

| ScFv | Co-stimulatory Signal | Signal Domain | ScFv | Co-stimulatory Signal | Signal Domain |
|---|---|---|---|---|---|
| IL13Ra2 | CD28 | CD8 | IL13Ra2 | CD80 | FcεRIβ |
| IL13Ra2 | CD28 | CD3ζ | IL13Ra2 | CD80 | FcεRIγ |
| IL13Ra2 | CD28 | CD3δ | IL13Ra2 | CD80 | DAP10 |
| IL13Ra2 | CD28 | CD3γ | IL13Ra2 | CD80 | DAP12 |
| IL13Ra2 | CD28 | CD3ε | IL13Ra2 | CD80 | CD32 |
| IL13Ra2 | CD28 | FcγRI-γ | IL13Ra2 | CD80 | CD79a |
| IL13Ra2 | CD28 | FcγRIII-γ | IL13Ra2 | CD80 | CD79b |
| IL13Ra2 | CD28 | FcεRIβ | IL13Ra2 | CD86 | CD8 |
| IL13Ra2 | CD28 | FcεRIγ | IL13Ra2 | CD86 | CD3ζ |
| IL13Ra2 | CD28 | DAP10 | IL13Ra2 | CD86 | CD3δ |
| IL13Ra2 | CD28 | DAP12 | IL13Ra2 | CD86 | CD3γ |
| IL13Ra2 | CD28 | CD32 | IL13Ra2 | CD86 | CD3ε |
| IL13Ra2 | CD28 | CD79a | IL13Ra2 | CD86 | FcγRI-γ |
| IL13Ra2 | CD28 | CD79b | IL13Ra2 | CD86 | FcγRIII-γ |
| IL13Ra2 | CD8 | CD8 | IL13Ra2 | CD86 | FcεRIβ |
| IL13Ra2 | CD8 | CD3ζ | IL13Ra2 | CD86 | FcεRIγ |
| IL13Ra2 | CD8 | CD3δ | IL13Ra2 | CD86 | DAP10 |
| IL13Ra2 | CD8 | CD3γ | IL13Ra2 | CD86 | DAP12 |
| IL13Ra2 | CD8 | CD3ε | IL13Ra2 | CD86 | CD32 |
| IL13Ra2 | CD8 | FcγRI-γ | IL13Ra2 | CD86 | CD79a |
| IL13Ra2 | CD8 | FcγRIII-γ | IL13Ra2 | CD86 | CD79b |
| IL13Ra2 | CD8 | FcεRIβ | IL13Ra2 | OX40 | CD8 |
| IL13Ra2 | CD8 | FcεRIγ | IL13Ra2 | OX40 | CD3ζ |
| IL13Ra2 | CD8 | DAP10 | IL13Ra2 | OX40 | CD3δ |
| IL13Ra2 | CD8 | DAP12 | IL13Ra2 | OX40 | CD3γ |
| IL13Ra2 | CD8 | CD32 | IL13Ra2 | OX40 | CD3ε |
| IL13Ra2 | CD8 | CD79a | IL13Ra2 | OX40 | FcγRI-γ |
| IL13Ra2 | CD8 | CD79b | IL13Ra2 | OX40 | FcγRIII-γ |
| IL13Ra2 | CD4 | CD8 | IL13Ra2 | OX40 | FcεRIβ |
| IL13Ra2 | CD4 | CD3ζ | IL13Ra2 | OX40 | FcεRIγ |
| IL13Ra2 | CD4 | CD3δ | IL13Ra2 | OX40 | DAP10 |
| IL13Ra2 | CD4 | CD3γ | IL13Ra2 | OX40 | DAP12 |
| IL13Ra2 | CD4 | CD3ε | IL13Ra2 | OX40 | CD32 |
| IL13Ra2 | CD4 | FcγRI-γ | IL13Ra2 | OX40 | CD79a |
| IL13Ra2 | CD4 | FcγRIII-γ | IL13Ra2 | OX40 | CD79b |
| IL13Ra2 | CD4 | FcεRIβ | IL13Ra2 | DAP10 | CD8 |
| IL13Ra2 | CD4 | FcεRIγ | IL13Ra2 | DAP10 | CD3ζ |
| IL13Ra2 | CD4 | DAP10 | IL13Ra2 | DAP10 | CD3δ |
| IL13Ra2 | CD4 | DAP12 | IL13Ra2 | DAP10 | CD3γ |
| IL13Ra2 | CD4 | CD32 | IL13Ra2 | DAP10 | CD3ε |
| IL13Ra2 | CD4 | CD79a | IL13Ra2 | DAP10 | FcγRI-γ |

TABLE 2-continued

Second Generation CARs

| ScFv | Co-stimulatory Signal | Signal Domain | ScFv | Co-stimulatory Signal | Signal Domain |
|---|---|---|---|---|---|
| IL13Ra2 | CD4 | CD79b | IL13Ra2 | DAP10 | FcγRIII-γ |
| IL13Ra2 | b2c | CD8 | IL13Ra2 | DAP10 | FcεRIβ |
| IL13Ra2 | b2c | CD3ζ | IL13Ra2 | DAP10 | FcεRIγ |
| IL13Ra2 | b2c | CD3δ | IL13Ra2 | DAP10 | DAP10 |
| IL13Ra2 | b2c | CD3γ | IL13Ra2 | DAP10 | DAP12 |
| IL13Ra2 | b2c | CD3ε | IL13Ra2 | DAP10 | CD32 |
| IL13Ra2 | b2c | FcγRI-γ | IL13Ra2 | DAP10 | CD79a |
| IL13Ra2 | b2c | FcγRIII-γ | IL13Ra2 | DAP10 | CD79b |
| IL13Ra2 | b2c | FcεRIβ | IL13Ra2 | DAP12 | CD8 |
| IL13Ra2 | b2c | FcεRIγ | IL13Ra2 | DAP12 | CD3ζ |
| IL13Ra2 | b2c | DAP10 | IL13Ra2 | DAP12 | CD3δ |
| IL13Ra2 | b2c | DAP12 | IL13Ra2 | DAP12 | CD3γ |
| IL13Ra2 | b2c | CD32 | IL13Ra2 | DAP12 | CD3ε |
| IL13Ra2 | b2c | CD79a | IL13Ra2 | DAP12 | FcγRI-γ |
| IL13Ra2 | b2c | CD79b | IL13Ra2 | DAP12 | FcγRIII-γ |
| IL13Ra2 | CD137/41BB | CD8 | IL13Ra2 | DAP12 | FcεRIβ |
| IL13Ra2 | CD137/41BB | CD3ζ | IL13Ra2 | DAP12 | FcεRIγ |
| IL13Ra2 | CD137/41BB | CD3δ | IL13Ra2 | DAP12 | DAP10 |
| IL13Ra2 | CD137/41BB | CD3γ | IL13Ra2 | DAP12 | DAP12 |
| IL13Ra2 | CD137/41BB | CD3ε | IL13Ra2 | DAP12 | CD32 |
| IL13Ra2 | CD137/41BB | FcγRI-γ | IL13Ra2 | DAP12 | CD79a |
| IL13Ra2 | CD137/41BB | FcγRIII-γ | IL13Ra2 | DAP12 | CD79b |
| IL13Ra2 | CD137/41BB | FcεRIβ | IL13Ra2 | MyD88 | CD8 |
| IL13Ra2 | CD137/41BB | FcεRIγ | IL13Ra2 | MyD88 | CD3ζ |
| IL13Ra2 | CD137/41BB | DAP10 | IL13Ra2 | MyD88 | CD3δ |
| IL13Ra2 | CD137/41BB | DAP12 | IL13Ra2 | MyD88 | CD3γ |
| IL13Ra2 | CD137/41BB | CD32 | IL13Ra2 | MyD88 | CD3ε |
| IL13Ra2 | CD137/41BB | CD79a | IL13Ra2 | MyD88 | FcγRI-γ |
| IL13Ra2 | CD137/41BB | CD79b | IL13Ra2 | MyD88 | FcγRIII-γ |
| IL13Ra2 | ICOS | CD8 | IL13Ra2 | MyD88 | FcεRIβ |
| IL13Ra2 | ICOS | CD3ζ | IL13Ra2 | MyD88 | FcεRIγ |
| IL13Ra2 | ICOS | CD3δ | IL13Ra2 | MyD88 | DAP10 |
| IL13Ra2 | ICOS | CD3γ | IL13Ra2 | MyD88 | DAP12 |
| IL13Ra2 | ICOS | CD3ε | IL13Ra2 | MyD88 | CD32 |
| IL13Ra2 | ICOS | FcγRI-γ | IL13Ra2 | MyD88 | CD79a |
| IL13Ra2 | ICOS | FcγRIII-γ | IL13Ra2 | MyD88 | CD79b |
| IL13Ra2 | ICOS | FcεRIβ | IL13Ra2 | CD7 | CD8 |
| IL13Ra2 | ICOS | FcεRIγ | IL13Ra2 | CD7 | CD3ζ |
| IL13Ra2 | ICOS | DAP10 | IL13Ra2 | CD7 | CD3δ |
| IL13Ra2 | ICOS | DAP12 | IL13Ra2 | CD7 | CD3γ |
| IL13Ra2 | ICOS | CD32 | IL13Ra2 | CD7 | CD3ε |
| IL13Ra2 | ICOS | CD79a | IL13Ra2 | CD7 | FcγRI-γ |
| IL13Ra2 | ICOS | CD79b | IL13Ra2 | CD7 | FcγRIII-γ |
| IL13Ra2 | CD27 | CD8 | IL13Ra2 | CD7 | FcεRIβ |
| IL13Ra2 | CD27 | CD3ζ | IL13Ra2 | CD7 | FcεRIγ |
| IL13Ra2 | CD27 | CD3δ | IL13Ra2 | CD7 | DAP10 |
| IL13Ra2 | CD27 | CD3γ | IL13Ra2 | CD7 | DAP12 |
| IL13Ra2 | CD27 | CD3ε | IL13Ra2 | CD7 | CD32 |
| IL13Ra2 | CD27 | FcγRI-γ | IL13Ra2 | CD7 | CD79a |
| IL13Ra2 | CD27 | FcγRIII-γ | IL13Ra2 | CD7 | CD79b |
| IL13Ra2 | CD27 | FcεRIβ | IL13Ra2 | BTNL3 | CD8 |
| IL13Ra2 | CD27 | FcεRIγ | IL13Ra2 | BTNL3 | CD3ζ |
| IL13Ra2 | CD27 | DAP10 | IL13Ra2 | BTNL3 | CD3δ |
| IL13Ra2 | CD27 | DAP12 | IL13Ra2 | BTNL3 | CD3γ |
| IL13Ra2 | CD27 | CD32 | IL13Ra2 | BTNL3 | CD3ε |
| IL13Ra2 | CD27 | CD79a | IL13Ra2 | BTNL3 | FcγRI-γ |
| IL13Ra2 | CD27 | CD79b | IL13Ra2 | BTNL3 | FcγRIII-γ |
| IL13Ra2 | CD28δ | CD8 | IL13Ra2 | BTNL3 | FcεRIβ |
| IL13Ra2 | CD28δ | CD3ζ | IL13Ra2 | BTNL3 | FcεRIγ |
| IL13Ra2 | CD28δ | CD3δ | IL13Ra2 | BTNL3 | DAP10 |
| IL13Ra2 | CD28δ | CD3γ | IL13Ra2 | BTNL3 | DAP12 |
| IL13Ra2 | CD28δ | CD3ε | IL13Ra2 | BTNL3 | CD32 |
| IL13Ra2 | CD28δ | FcγRI-γ | IL13Ra2 | BTNL3 | CD79a |
| IL13Ra2 | CD28δ | FcγRIII-γ | IL13Ra2 | BTNL3 | CD79b |
| IL13Ra2 | CD28δ | FcεRIβ | IL13Ra2 | NKG2D | CD8 |
| IL13Ra2 | CD28δ | FcεRIγ | IL13Ra2 | NKG2D | CD3ζ |
| IL13Ra2 | CD28δ | DAP10 | IL13Ra2 | NKG2D | CD3δ |
| IL13Ra2 | CD28δ | DAP12 | IL13Ra2 | NKG2D | CD3γ |
| IL13Ra2 | CD28δ | CD32 | IL13Ra2 | NKG2D | CD3ε |
| IL13Ra2 | CD28δ | CD79a | IL13Ra2 | NKG2D | FcγRI-γ |
| IL13Ra2 | CD28δ | CD79b | IL13Ra2 | NKG2D | FcγRIII-γ |
| IL13Ra2 | CD80 | CD8 | IL13Ra2 | NKG2D | FcεRIβ |
| IL13Ra2 | CD80 | CD3ζ | IL13Ra2 | NKG2D | FcεRIγ |
| IL13Ra2 | CD80 | CD3δ | IL13Ra2 | NKG2D | DAP10 |
| IL13Ra2 | CD80 | CD3γ | IL13Ra2 | NKG2D | DAP12 |
| IL13Ra2 | CD80 | CD3ε | IL13Ra2 | NKG2D | CD32 |
| IL13Ra2 | CD80 | FcγRI-γ | IL13Ra2 | NKG2D | CD79a |
| IL13Ra2 | CD80 | FcγRIII-γ | IL13Ra2 | NKG2D | CD79b |

TABLE 3

Third Generation CARs

| ScFv | Co-stimulatory Signal | Co-stimulatory Signal | Signal Domain |
|---|---|---|---|
| IL13Ra2 | CD28 | CD28 | CD8 |
| IL13Ra2 | CD28 | CD28 | CD3ζ |
| IL13Ra2 | CD28 | CD28 | CD3δ |
| IL13Ra2 | CD28 | CD28 | CD3γ |
| IL13Ra2 | CD28 | CD28 | CD3ε |
| IL13Ra2 | CD28 | CD28 | FcγRI-γ |
| IL13Ra2 | CD28 | CD28 | FcγRIII-γ |
| IL13Ra2 | CD28 | CD28 | FcεRIβ |
| IL13Ra2 | CD28 | CD28 | FcεRIγ |
| IL13Ra2 | CD28 | CD28 | DAP10 |
| IL13Ra2 | CD28 | CD28 | DAP12 |
| IL13Ra2 | CD28 | CD28 | CD32 |
| IL13Ra2 | CD28 | CD28 | CD79a |
| IL13Ra2 | CD28 | CD28 | CD79b |
| IL13Ra2 | CD28 | CD8 | CD8 |
| IL13Ra2 | CD28 | CD8 | CD3ζ |
| IL13Ra2 | CD28 | CD8 | CD3δ |
| IL13Ra2 | CD28 | CD8 | CD3γ |
| IL13Ra2 | CD28 | CD8 | CD3ε |
| IL13Ra2 | CD28 | CD8 | FcγRI-γ |
| IL13Ra2 | CD28 | CD8 | FcγRIII-γ |
| IL13Ra2 | CD28 | CD8 | FcεRIβ |
| IL13Ra2 | CD28 | CD8 | FcεRIγ |
| IL13Ra2 | CD28 | CD8 | DAP10 |
| IL13Ra2 | CD28 | CD8 | DAP12 |
| IL13Ra2 | CD28 | CD8 | CD32 |
| IL13Ra2 | CD28 | CD8 | CD79a |
| IL13Ra2 | CD28 | CD8 | CD79b |
| IL13Ra2 | CD28 | CD4 | CD8 |
| IL13Ra2 | CD28 | CD4 | CD3ζ |
| IL13Ra2 | CD28 | CD4 | CD3δ |
| IL13Ra2 | CD28 | CD4 | CD3γ |
| IL13Ra2 | CD28 | CD4 | CD3ε |
| IL13Ra2 | CD28 | CD4 | FcγRI-γ |
| IL13Ra2 | CD28 | CD4 | FcγRIII-γ |
| IL13Ra2 | CD28 | CD4 | FcεRIβ |
| IL13Ra2 | CD28 | CD4 | FcεRIγ |
| IL13Ra2 | CD28 | CD4 | DAP10 |
| IL13Ra2 | CD28 | CD4 | DAP12 |
| IL13Ra2 | CD28 | CD4 | CD32 |
| IL13Ra2 | CD28 | CD4 | CD79a |
| IL13Ra2 | CD28 | CD4 | CD79b |
| IL13Ra2 | CD28 | b2c | CD8 |
| IL13Ra2 | CD28 | b2c | CD3ζ |
| IL13Ra2 | CD28 | b2c | CD3δ |
| IL13Ra2 | CD28 | b2c | CD3γ |
| IL13Ra2 | CD28 | b2c | CD3ε |
| IL13Ra2 | CD28 | b2c | FcγRI-γ |
| IL13Ra2 | CD28 | b2c | FcγRIII-γ |
| IL13Ra2 | CD28 | b2c | FcεRIβ |
| IL13Ra2 | CD28 | b2c | FcεRIγ |
| IL13Ra2 | CD28 | b2c | DAP10 |
| IL13Ra2 | CD28 | b2c | DAP12 |
| IL13Ra2 | CD28 | b2c | CD32 |
| IL13Ra2 | CD28 | b2c | CD79a |
| IL13Ra2 | CD28 | b2c | CD79b |
| IL13Ra2 | CD28 | CD137/41BB | CD8 |

TABLE 3-continued

Third Generation CARs

| ScFv | Co-stimulatory Signal | Co-stimulatory Signal | Signal Domain |
|---|---|---|---|
| IL13Ra2 | CD28 | CD137/41BB | CD3ζ |
| IL13Ra2 | CD28 | CD137/41BB | CD3δ |
| IL13Ra2 | CD28 | CD137/41BB | CD3γ |
| IL13Ra2 | CD28 | CD137/41BB | CD3ε |
| IL13Ra2 | CD28 | CD137/41BB | FcγRI-γ |
| IL13Ra2 | CD28 | CD137/41BB | FcγRIII-γ |
| IL13Ra2 | CD28 | CD137/41BB | FcεRIβ |
| IL13Ra2 | CD28 | CD137/41BB | FcεRIγ |
| IL13Ra2 | CD28 | CD137/41BB | DAP10 |
| IL13Ra2 | CD28 | CD137/41BB | DAP12 |
| IL13Ra2 | CD28 | CD137/41BB | CD32 |
| IL13Ra2 | CD28 | CD137/41BB | CD79a |
| IL13Ra2 | CD28 | CD137/41BB | CD79b |
| IL13Ra2 | CD28 | ICOS | CD8 |
| IL13Ra2 | CD28 | ICOS | CD3ζ |
| IL13Ra2 | CD28 | ICOS | CD3δ |
| IL13Ra2 | CD28 | ICOS | CD3γ |
| IL13Ra2 | CD28 | ICOS | CD3ε |
| IL13Ra2 | CD28 | ICOS | FcγRI-γ |
| IL13Ra2 | CD28 | ICOS | FcγRIII-γ |
| IL13Ra2 | CD28 | ICOS | FcεRIβ |
| IL13Ra2 | CD28 | ICOS | FcεRIγ |
| IL13Ra2 | CD28 | ICOS | DAP10 |
| IL13Ra2 | CD28 | ICOS | DAP12 |
| IL13Ra2 | CD28 | ICOS | CD32 |
| IL13Ra2 | CD28 | ICOS | CD79a |
| IL13Ra2 | CD28 | ICOS | CD79b |
| IL13Ra2 | CD28 | CD27 | CD8 |
| IL13Ra2 | CD28 | CD27 | CD3ζ |
| IL13Ra2 | CD28 | CD27 | CD3δ |
| IL13Ra2 | CD28 | CD27 | CD3γ |
| IL13Ra2 | CD28 | CD27 | CD3ε |
| IL13Ra2 | CD28 | CD27 | FcγRI-γ |
| IL13Ra2 | CD28 | CD27 | FcγRIII-γ |
| IL13Ra2 | CD28 | CD27 | FcεRIβ |
| IL13Ra2 | CD28 | CD27 | FcεRIγ |
| IL13Ra2 | CD28 | CD27 | DAP10 |
| IL13Ra2 | CD28 | CD27 | DAP12 |
| IL13Ra2 | CD28 | CD27 | CD32 |
| IL13Ra2 | CD28 | CD27 | CD79a |
| IL13Ra2 | CD28 | CD27 | CD79b |
| IL13Ra2 | CD28 | CD28δ | CD8 |
| IL13Ra2 | CD28 | CD28δ | CD3ζ |
| IL13Ra2 | CD28 | CD28δ | CD3δ |
| IL13Ra2 | CD28 | CD28δ | CD3γ |
| IL13Ra2 | CD28 | CD28δ | CD3ε |
| IL13Ra2 | CD28 | CD28δ | FcγRI-γ |
| IL13Ra2 | CD28 | CD28δ | FcγRIII-γ |
| IL13Ra2 | CD28 | CD28δ | FcεRIβ |
| IL13Ra2 | CD28 | CD28δ | FcεRIγ |
| IL13Ra2 | CD28 | CD28δ | DAP10 |
| IL13Ra2 | CD28 | CD28δ | DAP12 |
| IL13Ra2 | CD28 | CD28δ | CD32 |
| IL13Ra2 | CD28 | CD28δ | CD79a |
| IL13Ra2 | CD28 | CD28δ | CD79b |
| IL13Ra2 | CD28 | CD80 | CD8 |
| IL13Ra2 | CD28 | CD80 | CD3ζ |
| IL13Ra2 | CD28 | CD80 | CD3δ |
| IL13Ra2 | CD28 | CD80 | CD3γ |
| IL13Ra2 | CD28 | CD80 | CD3ε |
| IL13Ra2 | CD28 | CD80 | FcγRI-γ |
| IL13Ra2 | CD28 | CD80 | FcγRIII-γ |
| IL13Ra2 | CD28 | CD80 | FcεRIβ |
| IL13Ra2 | CD28 | CD80 | FcεRIγ |
| IL13Ra2 | CD28 | CD80 | DAP10 |
| IL13Ra2 | CD28 | CD80 | DAP12 |
| IL13Ra2 | CD28 | CD80 | CD32 |
| IL13Ra2 | CD28 | CD80 | CD79a |
| IL13Ra2 | CD28 | CD80 | CD79b |
| IL13Ra2 | CD28 | CD86 | CD8 |
| IL13Ra2 | CD28 | CD86 | CD3ζ |
| IL13Ra2 | CD28 | CD86 | CD3δ |
| IL13Ra2 | CD28 | CD86 | CD3γ |
| IL13Ra2 | CD28 | CD86 | CD3ε |
| IL13Ra2 | CD28 | CD86 | FcγRI-γ |
| IL13Ra2 | CD28 | CD86 | FcγRIII-γ |
| IL13Ra2 | CD28 | CD86 | FcεRIβ |
| IL13Ra2 | CD28 | CD86 | FcεRIγ |
| IL13Ra2 | CD28 | CD86 | DAP10 |
| IL13Ra2 | CD28 | CD86 | DAP12 |
| IL13Ra2 | CD28 | CD86 | CD32 |
| IL13Ra2 | CD28 | CD86 | CD79a |
| IL13Ra2 | CD28 | CD86 | CD79b |
| IL13Ra2 | CD28 | OX40 | CD8 |
| IL13Ra2 | CD28 | OX40 | CD3ζ |
| IL13Ra2 | CD28 | OX40 | CD3δ |
| IL13Ra2 | CD28 | OX40 | CD3γ |
| IL13Ra2 | CD28 | OX40 | CD3ε |
| IL13Ra2 | CD28 | OX40 | FcγRI-γ |
| IL13Ra2 | CD28 | OX40 | FcγRIII-γ |
| IL13Ra2 | CD28 | OX40 | FcεRIβ |
| IL13Ra2 | CD28 | OX40 | FcεRIγ |
| IL13Ra2 | CD28 | OX40 | DAP10 |
| IL13Ra2 | CD28 | OX40 | DAP12 |
| IL13Ra2 | CD28 | OX40 | CD32 |
| IL13Ra2 | CD28 | OX40 | CD79a |
| IL13Ra2 | CD28 | OX40 | CD79b |
| IL13Ra2 | CD28 | DAP10 | CD8 |
| IL13Ra2 | CD28 | DAP10 | CD3ζ |
| IL13Ra2 | CD28 | DAP10 | CD3δ |
| IL13Ra2 | CD28 | DAP10 | CD3γ |
| IL13Ra2 | CD28 | DAP10 | CD3ε |
| IL13Ra2 | CD28 | DAP10 | FcγRI-γ |
| IL13Ra2 | CD28 | DAP10 | FcγRIII-γ |
| IL13Ra2 | CD28 | DAP10 | FcεRIβ |
| IL13Ra2 | CD28 | DAP10 | FcεRIγ |
| IL13Ra2 | CD28 | DAP10 | DAP10 |
| IL13Ra2 | CD28 | DAP10 | DAP12 |
| IL13Ra2 | CD28 | DAP10 | CD32 |
| IL13Ra2 | CD28 | DAP10 | CD79a |
| IL13Ra2 | CD28 | DAP10 | CD79b |
| IL13Ra2 | CD28 | DAP12 | CD8 |
| IL13Ra2 | CD28 | DAP12 | CD3ζ |
| IL13Ra2 | CD28 | DAP12 | CD3δ |
| IL13Ra2 | CD28 | DAP12 | CD3γ |
| IL13Ra2 | CD28 | DAP12 | CD3ε |
| IL13Ra2 | CD28 | DAP12 | FcγRI-γ |
| IL13Ra2 | CD28 | DAP12 | FcγRIII-γ |
| IL13Ra2 | CD28 | DAP12 | FcεRIβ |
| IL13Ra2 | CD28 | DAP12 | FcεRIγ |
| IL13Ra2 | CD28 | DAP12 | DAP10 |
| IL13Ra2 | CD28 | DAP12 | DAP12 |
| IL13Ra2 | CD28 | DAP12 | CD32 |
| IL13Ra2 | CD28 | DAP12 | CD79a |
| IL13Ra2 | CD28 | DAP12 | CD79b |
| IL13Ra2 | CD28 | MyD88 | CD8 |
| IL13Ra2 | CD28 | MyD88 | CD3ζ |
| IL13Ra2 | CD28 | MyD88 | CD3δ |
| IL13Ra2 | CD28 | MyD88 | CD3γ |
| IL13Ra2 | CD28 | MyD88 | CD3ε |
| IL13Ra2 | CD28 | MyD88 | FcγRI-γ |
| IL13Ra2 | CD28 | MyD88 | FcγRIII-γ |
| IL13Ra2 | CD28 | MyD88 | FcεRIβ |
| IL13Ra2 | CD28 | MyD88 | FcεRIγ |
| IL13Ra2 | CD28 | MyD88 | DAP10 |
| IL13Ra2 | CD28 | MyD88 | DAP12 |
| IL13Ra2 | CD28 | MyD88 | CD32 |
| IL13Ra2 | CD28 | MyD88 | CD79a |
| IL13Ra2 | CD28 | MyD88 | CD79b |
| IL13Ra2 | CD28 | CD7 | CD8 |
| IL13Ra2 | CD28 | CD7 | CD3ζ |
| IL13Ra2 | CD28 | CD7 | CD3δ |
| IL13Ra2 | CD28 | CD7 | CD3γ |
| IL13Ra2 | CD28 | CD7 | CD3ε |
| IL13Ra2 | CD28 | CD7 | FcγRI-γ |
| IL13Ra2 | CD28 | CD7 | FcγRIII-γ |
| IL13Ra2 | CD28 | CD7 | FcεRIβ |
| IL13Ra2 | CD28 | CD7 | FcεRIγ |
| IL13Ra2 | CD28 | CD7 | DAP10 |
| IL13Ra2 | CD28 | CD7 | DAP12 |

TABLE 3-continued

Third Generation CARs

| ScFv | Co-stimulatory Signal | Co-stimulatory Signal | Signal Domain |
|---|---|---|---|
| IL13Ra2 | CD28 | CD7 | CD32 |
| IL13Ra2 | CD28 | CD7 | CD79a |
| IL13Ra2 | CD28 | CD7 | CD79b |
| IL13Ra2 | CD28 | BTNL3 | CD8 |
| IL13Ra2 | CD28 | BTNL3 | CD3ζ |
| IL13Ra2 | CD28 | BTNL3 | CD3δ |
| IL13Ra2 | CD28 | BTNL3 | CD3γ |
| IL13Ra2 | CD28 | BTNL3 | CD3ε |
| IL13Ra2 | CD28 | BTNL3 | FcγRI-γ |
| IL13Ra2 | CD28 | BTNL3 | FcγRIII-γ |
| IL13Ra2 | CD28 | BTNL3 | FcεRIβ |
| IL13Ra2 | CD28 | BTNL3 | FcεRIγ |
| IL13Ra2 | CD28 | BTNL3 | DAP10 |
| IL13Ra2 | CD28 | BTNL3 | DAP12 |
| IL13Ra2 | CD28 | BTNL3 | CD32 |
| IL13Ra2 | CD28 | BTNL3 | CD79a |
| IL13Ra2 | CD28 | BTNL3 | CD79b |
| IL13Ra2 | CD28 | NKG2D | CD8 |
| IL13Ra2 | CD28 | NKG2D | CD3ζ |
| IL13Ra2 | CD28 | NKG2D | CD3δ |
| IL13Ra2 | CD28 | NKG2D | CD3γ |
| IL13Ra2 | CD28 | NKG2D | CD3ε |
| IL13Ra2 | CD28 | NKG2D | FcγRI-γ |
| IL13Ra2 | CD28 | NKG2D | FcγRIII-γ |
| IL13Ra2 | CD28 | NKG2D | FcεRIβ |
| IL13Ra2 | CD28 | NKG2D | FcεRIγ |
| IL13Ra2 | CD28 | NKG2D | DAP10 |
| IL13Ra2 | CD28 | NKG2D | DAP12 |
| IL13Ra2 | CD28 | NKG2D | CD32 |
| IL13Ra2 | CD28 | NKG2D | CD79a |
| IL13Ra2 | CD28 | NKG2D | CD79b |
| IL13Ra2 | CD8 | CD28 | CD8 |
| IL13Ra2 | CD8 | CD28 | CD3ζ |
| IL13Ra2 | CD8 | CD28 | CD3δ |
| IL13Ra2 | CD8 | CD28 | CD3γ |
| IL13Ra2 | CD8 | CD28 | CD3ε |
| IL13Ra2 | CD8 | CD28 | FcγRI-γ |
| IL13Ra2 | CD8 | CD28 | FcγRIII-γ |
| IL13Ra2 | CD8 | CD28 | FcεRIβ |
| IL13Ra2 | CD8 | CD28 | FcεRIγ |
| IL13Ra2 | CD8 | CD28 | DAP10 |
| IL13Ra2 | CD8 | CD28 | DAP12 |
| IL13Ra2 | CD8 | CD28 | CD32 |
| IL13Ra2 | CD8 | CD28 | CD79a |
| IL13Ra2 | CD8 | CD28 | CD79b |
| IL13Ra2 | CD8 | CD8 | CD8 |
| IL13Ra2 | CD8 | CD8 | CD3ζ |
| IL13Ra2 | CD8 | CD8 | CD3δ |
| IL13Ra2 | CD8 | CD8 | CD3γ |
| IL13Ra2 | CD8 | CD8 | CD3ε |
| IL13Ra2 | CD8 | CD8 | FcγRI-γ |
| IL13Ra2 | CD8 | CD8 | FcγRIII-γ |
| IL13Ra2 | CD8 | CD8 | FcεRIβ |
| IL13Ra2 | CD8 | CD8 | FcεRIγ |
| IL13Ra2 | CD8 | CD8 | DAP10 |
| IL13Ra2 | CD8 | CD8 | DAP12 |
| IL13Ra2 | CD8 | CD8 | CD32 |
| IL13Ra2 | CD8 | CD8 | CD79a |
| IL13Ra2 | CD8 | CD8 | CD79b |
| IL13Ra2 | CD8 | CD4 | CD8 |
| IL13Ra2 | CD8 | CD4 | CD3ζ |
| IL13Ra2 | CD8 | CD4 | CD3δ |
| IL13Ra2 | CD8 | CD4 | CD3γ |
| IL13Ra2 | CD8 | CD4 | CD3ε |
| IL13Ra2 | CD8 | CD4 | FcγRI-γ |
| IL13Ra2 | CD8 | CD4 | FcγRIII-γ |
| IL13Ra2 | CD8 | CD4 | FcεRIβ |
| IL13Ra2 | CD8 | CD4 | FcεRIγ |
| IL13Ra2 | CD8 | CD4 | DAP10 |
| IL13Ra2 | CD8 | CD4 | DAP12 |
| IL13Ra2 | CD8 | CD4 | CD32 |
| IL13Ra2 | CD8 | CD4 | CD79a |
| IL13Ra2 | CD8 | CD4 | CD79b |
| IL13Ra2 | CD8 | b2c | CD8 |
| IL13Ra2 | CD8 | b2c | CD3ζ |
| IL13Ra2 | CD8 | b2c | CD3δ |
| IL13Ra2 | CD8 | b2c | CD3γ |
| IL13Ra2 | CD8 | b2c | CD3ε |
| IL13Ra2 | CD8 | b2c | FcγRI-γ |
| IL13Ra2 | CD8 | b2c | FcγRIII-γ |
| IL13Ra2 | CD8 | b2c | FcεRIβ |
| IL13Ra2 | CD8 | b2c | FcεRIγ |
| IL13Ra2 | CD8 | b2c | DAP10 |
| IL13Ra2 | CD8 | b2c | DAP12 |
| IL13Ra2 | CD8 | b2c | CD32 |
| IL13Ra2 | CD8 | b2c | CD79a |
| IL13Ra2 | CD8 | b2c | CD79b |
| IL13Ra2 | CD8 | CD137/41BB | CD8 |
| IL13Ra2 | CD8 | CD137/41BB | CD3ζ |
| IL13Ra2 | CD8 | CD137/41BB | CD3δ |
| IL13Ra2 | CD8 | CD137/41BB | CD3γ |
| IL13Ra2 | CD8 | CD137/41BB | CD3ε |
| IL13Ra2 | CD8 | CD137/41BB | FcγRI-γ |
| IL13Ra2 | CD8 | CD137/41BB | FcγRIII-γ |
| IL13Ra2 | CD8 | CD137/41BB | FcεRIβ |
| IL13Ra2 | CD8 | CD137/41BB | FcεRIγ |
| IL13Ra2 | CD8 | CD137/41BB | DAP10 |
| IL13Ra2 | CD8 | CD137/41BB | DAP12 |
| IL13Ra2 | CD8 | CD137/41BB | CD32 |
| IL13Ra2 | CD8 | CD137/41BB | CD79a |
| IL13Ra2 | CD8 | CD137/41BB | CD79b |
| IL13Ra2 | CD8 | ICOS | CD8 |
| IL13Ra2 | CD8 | ICOS | CD3ζ |
| IL13Ra2 | CD8 | ICOS | CD3δ |
| IL13Ra2 | CD8 | ICOS | CD3γ |
| IL13Ra2 | CD8 | ICOS | CD3ε |
| IL13Ra2 | CD8 | ICOS | FcγRI-γ |
| IL13Ra2 | CD8 | ICOS | FcγRIII-γ |
| IL13Ra2 | CD8 | ICOS | FcεRIβ |
| IL13Ra2 | CD8 | ICOS | FcεRIγ |
| IL13Ra2 | CD8 | ICOS | DAP10 |
| IL13Ra2 | CD8 | ICOS | DAP12 |
| IL13Ra2 | CD8 | ICOS | CD32 |
| IL13Ra2 | CD8 | ICOS | CD79a |
| IL13Ra2 | CD8 | ICOS | CD79b |
| IL13Ra2 | CD8 | CD27 | CD8 |
| IL13Ra2 | CD8 | CD27 | CD3ζ |
| IL13Ra2 | CD8 | CD27 | CD3δ |
| IL13Ra2 | CD8 | CD27 | CD3γ |
| IL13Ra2 | CD8 | CD27 | CD3ε |
| IL13Ra2 | CD8 | CD27 | FcγRI-γ |
| IL13Ra2 | CD8 | CD27 | FcγRIII-γ |
| IL13Ra2 | CD8 | CD27 | FcεRIβ |
| IL13Ra2 | CD8 | CD27 | FcεRIγ |
| IL13Ra2 | CD8 | CD27 | DAP10 |
| IL13Ra2 | CD8 | CD27 | DAP12 |
| IL13Ra2 | CD8 | CD27 | CD32 |
| IL13Ra2 | CD8 | CD27 | CD79a |
| IL13Ra2 | CD8 | CD27 | CD79b |
| IL13Ra2 | CD8 | CD28δ | CD8 |
| IL13Ra2 | CD8 | CD28δ | CD3ζ |
| IL13Ra2 | CD8 | CD28δ | CD3δ |
| IL13Ra2 | CD8 | CD28δ | CD3γ |
| IL13Ra2 | CD8 | CD28δ | CD3ε |
| IL13Ra2 | CD8 | CD28δ | FcγRI-γ |
| IL13Ra2 | CD8 | CD28δ | FcγRIII-γ |
| IL13Ra2 | CD8 | CD28δ | FcεRIβ |
| IL13Ra2 | CD8 | CD28δ | FcεRIγ |
| IL13Ra2 | CD8 | CD28δ | DAP10 |
| IL13Ra2 | CD8 | CD28δ | DAP12 |
| IL13Ra2 | CD8 | CD28δ | CD32 |
| IL13Ra2 | CD8 | CD28δ | CD79a |
| IL13Ra2 | CD8 | CD28δ | CD79b |
| IL13Ra2 | CD8 | CD80 | CD8 |
| IL13Ra2 | CD8 | CD80 | CD3ζ |
| IL13Ra2 | CD8 | CD80 | CD3δ |
| IL13Ra2 | CD8 | CD80 | CD3γ |
| IL13Ra2 | CD8 | CD80 | CD3ε |
| IL13Ra2 | CD8 | CD80 | FcγRI-γ |
| IL13Ra2 | CD8 | CD80 | FcγRIII-γ |

TABLE 3-continued

Third Generation CARs

| ScFv | Co-stimulatory Signal | Co-stimulatory Signal | Signal Domain |
|---|---|---|---|
| IL13Ra2 | CD8 | CD80 | FcεRIβ |
| IL13Ra2 | CD8 | CD80 | FcεRIγ |
| IL13Ra2 | CD8 | CD80 | DAP10 |
| IL13Ra2 | CD8 | CD80 | DAP12 |
| IL13Ra2 | CD8 | CD80 | CD32 |
| IL13Ra2 | CD8 | CD80 | CD79a |
| IL13Ra2 | CD8 | CD80 | CD79b |
| IL13Ra2 | CD8 | CD86 | CD8 |
| IL13Ra2 | CD8 | CD86 | CD3ζ |
| IL13Ra2 | CD8 | CD86 | CD3δ |
| IL13Ra2 | CD8 | CD86 | CD3γ |
| IL13Ra2 | CD8 | CD86 | CD3ε |
| IL13Ra2 | CD8 | CD86 | FcγRI-γ |
| IL13Ra2 | CD8 | CD86 | FcγRIII-γ |
| IL13Ra2 | CD8 | CD86 | FcεRIβ |
| IL13Ra2 | CD8 | CD86 | FcεRIγ |
| IL13Ra2 | CD8 | CD86 | DAP10 |
| IL13Ra2 | CD8 | CD86 | DAP12 |
| IL13Ra2 | CD8 | CD86 | CD32 |
| IL13Ra2 | CD8 | CD86 | CD79a |
| IL13Ra2 | CD8 | CD86 | CD79b |
| IL13Ra2 | CD8 | OX40 | CD8 |
| IL13Ra2 | CD8 | OX40 | CD3ζ |
| IL13Ra2 | CD8 | OX40 | CD3δ |
| IL13Ra2 | CD8 | OX40 | CD3γ |
| IL13Ra2 | CD8 | OX40 | CD3ε |
| IL13Ra2 | CD8 | OX40 | FcγRI-γ |
| IL13Ra2 | CD8 | OX40 | FcγRIII-γ |
| IL13Ra2 | CD8 | OX40 | FcεRIβ |
| IL13Ra2 | CD8 | OX40 | FcεRIγ |
| IL13Ra2 | CD8 | OX40 | DAP10 |
| IL13Ra2 | CD8 | OX40 | DAP12 |
| IL13Ra2 | CD8 | OX40 | CD32 |
| IL13Ra2 | CD8 | OX40 | CD79a |
| IL13Ra2 | CD8 | OX40 | CD79b |
| IL13Ra2 | CD8 | DAP10 | CD8 |
| IL13Ra2 | CD8 | DAP10 | CD3ζ |
| IL13Ra2 | CD8 | DAP10 | CD3δ |
| IL13Ra2 | CD8 | DAP10 | CD3γ |
| IL13Ra2 | CD8 | DAP10 | CD3ε |
| IL13Ra2 | CD8 | DAP10 | FcγRI-γ |
| IL13Ra2 | CD8 | DAP10 | FcγRIII-γ |
| IL13Ra2 | CD8 | DAP10 | FcεRIβ |
| IL13Ra2 | CD8 | DAP10 | FcεRIγ |
| IL13Ra2 | CD8 | DAP10 | DAP10 |
| IL13Ra2 | CD8 | DAP10 | DAP12 |
| IL13Ra2 | CD8 | DAP10 | CD32 |
| IL13Ra2 | CD8 | DAP10 | CD79a |
| IL13Ra2 | CD8 | DAP10 | CD79b |
| IL13Ra2 | CD8 | DAP12 | CD8 |
| IL13Ra2 | CD8 | DAP12 | CD3ζ |
| IL13Ra2 | CD8 | DAP12 | CD3δ |
| IL13Ra2 | CD8 | DAP12 | CD3γ |
| IL13Ra2 | CD8 | DAP12 | CD3ε |
| IL13Ra2 | CD8 | DAP12 | FcγRI-γ |
| IL13Ra2 | CD8 | DAP12 | FcγRIII-γ |
| IL13Ra2 | CD8 | DAP12 | FcεRIβ |
| IL13Ra2 | CD8 | DAP12 | FcεRIγ |
| IL13Ra2 | CD8 | DAP12 | DAP10 |
| IL13Ra2 | CD8 | DAP12 | DAP12 |
| IL13Ra2 | CD8 | DAP12 | CD32 |
| IL13Ra2 | CD8 | DAP12 | CD79a |
| IL13Ra2 | CD8 | DAP12 | CD79b |
| IL13Ra2 | CD8 | MyD88 | CD8 |
| IL13Ra2 | CD8 | MyD88 | CD3ζ |
| IL13Ra2 | CD8 | MyD88 | CD3δ |
| IL13Ra2 | CD8 | MyD88 | CD3γ |
| IL13Ra2 | CD8 | MyD88 | CD3ε |
| IL13Ra2 | CD8 | MyD88 | FcγRI-γ |
| IL13Ra2 | CD8 | MyD88 | FcγRIII-γ |
| IL13Ra2 | CD8 | MyD88 | FcεRIβ |
| IL13Ra2 | CD8 | MyD88 | FcεRIγ |
| IL13Ra2 | CD8 | MyD88 | DAP10 |
| IL13Ra2 | CD8 | MyD88 | DAP12 |
| IL13Ra2 | CD8 | MyD88 | CD32 |
| IL13Ra2 | CD8 | MyD88 | CD79a |
| IL13Ra2 | CD8 | MyD88 | CD79b |
| IL13Ra2 | CD8 | CD7 | CD8 |
| IL13Ra2 | CD8 | CD7 | CD3ζ |
| IL13Ra2 | CD8 | CD7 | CD3δ |
| IL13Ra2 | CD8 | CD7 | CD3γ |
| IL13Ra2 | CD8 | CD7 | CD3ε |
| IL13Ra2 | CD8 | CD7 | FcγRI-γ |
| IL13Ra2 | CD8 | CD7 | FcγRIII-γ |
| IL13Ra2 | CD8 | CD7 | FcεRIβ |
| IL13Ra2 | CD8 | CD7 | FcεRIγ |
| IL13Ra2 | CD8 | CD7 | DAP10 |
| IL13Ra2 | CD8 | CD7 | DAP12 |
| IL13Ra2 | CD8 | CD7 | CD32 |
| IL13Ra2 | CD8 | CD7 | CD79a |
| IL13Ra2 | CD8 | CD7 | CD79b |
| IL13Ra2 | CD8 | BTNL3 | CD8 |
| IL13Ra2 | CD8 | BTNL3 | CD3ζ |
| IL13Ra2 | CD8 | BTNL3 | CD3δ |
| IL13Ra2 | CD8 | BTNL3 | CD3γ |
| IL13Ra2 | CD8 | BTNL3 | CD3ε |
| IL13Ra2 | CD8 | BTNL3 | FcγRI-γ |
| IL13Ra2 | CD8 | BTNL3 | FcγRIII-γ |
| IL13Ra2 | CD8 | BTNL3 | FcεRIβ |
| IL13Ra2 | CD8 | BTNL3 | FcεRIγ |
| IL13Ra2 | CD8 | BTNL3 | DAP10 |
| IL13Ra2 | CD8 | BTNL3 | DAP12 |
| IL13Ra2 | CD8 | BTNL3 | CD32 |
| IL13Ra2 | CD8 | BTNL3 | CD79a |
| IL13Ra2 | CD8 | BTNL3 | CD79b |
| IL13Ra2 | CD8 | NKG2D | CD8 |
| IL13Ra2 | CD8 | NKG2D | CD3ζ |
| IL13Ra2 | CD8 | NKG2D | CD3δ |
| IL13Ra2 | CD8 | NKG2D | CD3γ |
| IL13Ra2 | CD8 | NKG2D | CD3ε |
| IL13Ra2 | CD8 | NKG2D | FcγRI-γ |
| IL13Ra2 | CD8 | NKG2D | FcγRIII-γ |
| IL13Ra2 | CD8 | NKG2D | FcεRIβ |
| IL13Ra2 | CD8 | NKG2D | FcεRIγ |
| IL13Ra2 | CD8 | NKG2D | DAP10 |
| IL13Ra2 | CD8 | NKG2D | DAP12 |
| IL13Ra2 | CD8 | NKG2D | CD32 |
| IL13Ra2 | CD8 | NKG2D | CD79a |
| IL13Ra2 | CD8 | NKG2D | CD79b |
| IL13Ra2 | CD4 | CD28 | CD8 |
| IL13Ra2 | CD4 | CD28 | CD3ζ |
| IL13Ra2 | CD4 | CD28 | CD3δ |
| IL13Ra2 | CD4 | CD28 | CD3γ |
| IL13Ra2 | CD4 | CD28 | CD3ε |
| IL13Ra2 | CD4 | CD28 | FcγRI-γ |
| IL13Ra2 | CD4 | CD28 | FcγRIII-γ |
| IL13Ra2 | CD4 | CD28 | FcεRIβ |
| IL13Ra2 | CD4 | CD28 | FcεRIγ |
| IL13Ra2 | CD4 | CD28 | DAP10 |
| IL13Ra2 | CD4 | CD28 | DAP12 |
| IL13Ra2 | CD4 | CD28 | CD32 |
| IL13Ra2 | CD4 | CD28 | CD79a |
| IL13Ra2 | CD4 | CD28 | CD79b |
| IL13Ra2 | CD4 | CD8 | CD8 |
| IL13Ra2 | CD4 | CD8 | CD3ζ |
| IL13Ra2 | CD4 | CD8 | CD3δ |
| IL13Ra2 | CD4 | CD8 | CD3γ |
| IL13Ra2 | CD4 | CD8 | CD3ε |
| IL13Ra2 | CD4 | CD8 | FcγRI-γ |
| IL13Ra2 | CD4 | CD8 | FcγRIII-γ |
| IL13Ra2 | CD4 | CD8 | FcεRIβ |
| IL13Ra2 | CD4 | CD8 | FcεRIγ |
| IL13Ra2 | CD4 | CD8 | DAP10 |
| IL13Ra2 | CD4 | CD8 | DAP12 |
| IL13Ra2 | CD4 | CD8 | CD32 |
| IL13Ra2 | CD4 | CD8 | CD79a |
| IL13Ra2 | CD4 | CD8 | CD79b |
| IL13Ra2 | CD4 | CD4 | CD8 |
| IL13Ra2 | CD4 | CD4 | CD3ζ |
| IL13Ra2 | CD4 | CD4 | CD3δ |

TABLE 3-continued

Third Generation CARs

| ScFv | Co-stimulatory Signal | Co-stimulatory Signal | Signal Domain |
|---|---|---|---|
| IL13Ra2 | CD4 | CD4 | CD3γ |
| IL13Ra2 | CD4 | CD4 | CD3ε |
| IL13Ra2 | CD4 | CD4 | FcγRI-γ |
| IL13Ra2 | CD4 | CD4 | FcγRIII-γ |
| IL13Ra2 | CD4 | CD4 | FcεRIβ |
| IL13Ra2 | CD4 | CD4 | FcεRIγ |
| IL13Ra2 | CD4 | CD4 | DAP10 |
| IL13Ra2 | CD4 | CD4 | DAP12 |
| IL13Ra2 | CD4 | CD4 | CD32 |
| IL13Ra2 | CD4 | CD4 | CD79a |
| IL13Ra2 | CD4 | CD4 | CD79b |
| IL13Ra2 | CD4 | b2c | CD8 |
| IL13Ra2 | CD4 | b2c | CD3ζ |
| IL13Ra2 | CD4 | b2c | CD3δ |
| IL13Ra2 | CD4 | b2c | CD3γ |
| IL13Ra2 | CD4 | b2c | CD3ε |
| IL13Ra2 | CD4 | b2c | FcγRI-γ |
| IL13Ra2 | CD4 | b2c | FcγRIII-γ |
| IL13Ra2 | CD4 | b2c | FcεRIβ |
| IL13Ra2 | CD4 | b2c | FcεRIγ |
| IL13Ra2 | CD4 | b2c | DAP10 |
| IL13Ra2 | CD4 | b2c | DAP12 |
| IL13Ra2 | CD4 | b2c | CD32 |
| IL13Ra2 | CD4 | b2c | CD79a |
| IL13Ra2 | CD4 | b2c | CD79b |
| IL13Ra2 | CD4 | CD137/41BB | CD8 |
| IL13Ra2 | CD4 | CD137/41BB | CD3ζ |
| IL13Ra2 | CD4 | CD137/41BB | CD3δ |
| IL13Ra2 | CD4 | CD137/41BB | CD3γ |
| IL13Ra2 | CD4 | CD137/41BB | CD3ε |
| IL13Ra2 | CD4 | CD137/41BB | FcγRI-γ |
| IL13Ra2 | CD4 | CD137/41BB | FcγRIII-γ |
| IL13Ra2 | CD4 | CD137/41BB | FcεRIβ |
| IL13Ra2 | CD4 | CD137/41BB | FcεRIγ |
| IL13Ra2 | CD4 | CD137/41BB | DAP10 |
| IL13Ra2 | CD4 | CD137/41BB | DAP12 |
| IL13Ra2 | CD4 | CD137/41BB | CD32 |
| IL13Ra2 | CD4 | CD137/41BB | CD79a |
| IL13Ra2 | CD4 | CD137/41BB | CD79b |
| IL13Ra2 | CD4 | ICOS | CD8 |
| IL13Ra2 | CD4 | ICOS | CD3ζ |
| IL13Ra2 | CD4 | ICOS | CD3δ |
| IL13Ra2 | CD4 | ICOS | CD3γ |
| IL13Ra2 | CD4 | ICOS | CD3ε |
| IL13Ra2 | CD4 | ICOS | FcγRI-γ |
| IL13Ra2 | CD4 | ICOS | FcγRIII-γ |
| IL13Ra2 | CD4 | ICOS | FcεRIβ |
| IL13Ra2 | CD4 | ICOS | FcεRIγ |
| IL13Ra2 | CD4 | ICOS | DAP10 |
| IL13Ra2 | CD4 | ICOS | DAP12 |
| IL13Ra2 | CD4 | ICOS | CD32 |
| IL13Ra2 | CD4 | ICOS | CD79a |
| IL13Ra2 | CD4 | ICOS | CD79b |
| IL13Ra2 | CD4 | CD27 | CD8 |
| IL13Ra2 | CD4 | CD27 | CD3ζ |
| IL13Ra2 | CD4 | CD27 | CD3δ |
| IL13Ra2 | CD4 | CD27 | CD3γ |
| IL13Ra2 | CD4 | CD27 | CD3ε |
| IL13Ra2 | CD4 | CD27 | FcγRI-γ |
| IL13Ra2 | CD4 | CD27 | FcγRIII-γ |
| IL13Ra2 | CD4 | CD27 | FcεRIβ |
| IL13Ra2 | CD4 | CD27 | FcεRIγ |
| IL13Ra2 | CD4 | CD27 | DAP10 |
| IL13Ra2 | CD4 | CD27 | DAP12 |
| IL13Ra2 | CD4 | CD27 | CD32 |
| IL13Ra2 | CD4 | CD27 | CD79a |
| IL13Ra2 | CD4 | CD27 | CD79b |
| IL13Ra2 | CD4 | CD28δ | CD8 |
| IL13Ra2 | CD4 | CD28δ | CD3ζ |
| IL13Ra2 | CD4 | CD28δ | CD3δ |
| IL13Ra2 | CD4 | CD28δ | CD3γ |
| IL13Ra2 | CD4 | CD28δ | CD3ε |
| IL13Ra2 | CD4 | CD28δ | FcγRI-γ |
| IL13Ra2 | CD4 | CD28δ | FcγRIII-γ |
| IL13Ra2 | CD4 | CD28δ | FcεRIβ |
| IL13Ra2 | CD4 | CD28δ | FcεRIγ |
| IL13Ra2 | CD4 | CD28δ | DAP10 |
| IL13Ra2 | CD4 | CD28δ | DAP12 |
| IL13Ra2 | CD4 | CD28δ | CD32 |
| IL13Ra2 | CD4 | CD28δ | CD79a |
| IL13Ra2 | CD4 | CD28δ | CD79b |
| IL13Ra2 | CD4 | CD80 | CD8 |
| IL13Ra2 | CD4 | CD80 | CD3ζ |
| IL13Ra2 | CD4 | CD80 | CD3δ |
| IL13Ra2 | CD4 | CD80 | CD3γ |
| IL13Ra2 | CD4 | CD80 | CD3ε |
| IL13Ra2 | CD4 | CD80 | FcγRI-γ |
| IL13Ra2 | CD4 | CD80 | FcγRIII-γ |
| IL13Ra2 | CD4 | CD80 | FcεRIβ |
| IL13Ra2 | CD4 | CD80 | FcεRIγ |
| IL13Ra2 | CD4 | CD80 | DAP10 |
| IL13Ra2 | CD4 | CD80 | DAP12 |
| IL13Ra2 | CD4 | CD80 | CD32 |
| IL13Ra2 | CD4 | CD80 | CD79a |
| IL13Ra2 | CD4 | CD80 | CD79b |
| IL13Ra2 | CD4 | CD86 | CD8 |
| IL13Ra2 | CD4 | CD86 | CD3ζ |
| IL13Ra2 | CD4 | CD86 | CD3δ |
| IL13Ra2 | CD4 | CD86 | CD3γ |
| IL13Ra2 | CD4 | CD86 | CD3ε |
| IL13Ra2 | CD4 | CD86 | FcγRI-γ |
| IL13Ra2 | CD4 | CD86 | FcγRIII-γ |
| IL13Ra2 | CD4 | CD86 | FcεRIβ |
| IL13Ra2 | CD4 | CD86 | FcεRIγ |
| IL13Ra2 | CD4 | CD86 | DAP10 |
| IL13Ra2 | CD4 | CD86 | DAP12 |
| IL13Ra2 | CD4 | CD86 | CD32 |
| IL13Ra2 | CD4 | CD86 | CD79a |
| IL13Ra2 | CD4 | CD86 | CD79b |
| IL13Ra2 | CD4 | OX40 | CD8 |
| IL13Ra2 | CD4 | OX40 | CD3ζ |
| IL13Ra2 | CD4 | OX40 | CD3δ |
| IL13Ra2 | CD4 | OX40 | CD3γ |
| IL13Ra2 | CD4 | OX40 | CD3ε |
| IL13Ra2 | CD4 | OX40 | FcγRI-γ |
| IL13Ra2 | CD4 | OX40 | FcγRIII-γ |
| IL13Ra2 | CD4 | OX40 | FcεRIβ |
| IL13Ra2 | CD4 | OX40 | FcεRIγ |
| IL13Ra2 | CD4 | OX40 | DAP10 |
| IL13Ra2 | CD4 | OX40 | DAP12 |
| IL13Ra2 | CD4 | OX40 | CD32 |
| IL13Ra2 | CD4 | OX40 | CD79a |
| IL13Ra2 | CD4 | OX40 | CD79b |
| IL13Ra2 | CD4 | DAP10 | CD8 |
| IL13Ra2 | CD4 | DAP10 | CD3ζ |
| IL13Ra2 | CD4 | DAP10 | CD3δ |
| IL13Ra2 | CD4 | DAP10 | CD3γ |
| IL13Ra2 | CD4 | DAP10 | CD3ε |
| IL13Ra2 | CD4 | DAP10 | FcγRI-γ |
| IL13Ra2 | CD4 | DAP10 | FcγRIII-γ |
| IL13Ra2 | CD4 | DAP10 | FcεRIβ |
| IL13Ra2 | CD4 | DAP10 | FcεRIγ |
| IL13Ra2 | CD4 | DAP10 | DAP10 |
| IL13Ra2 | CD4 | DAP10 | DAP12 |
| IL13Ra2 | CD4 | DAP10 | CD32 |
| IL13Ra2 | CD4 | DAP10 | CD79a |
| IL13Ra2 | CD4 | DAP10 | CD79b |
| IL13Ra2 | CD4 | DAP12 | CD8 |
| IL13Ra2 | CD4 | DAP12 | CD3ζ |
| IL13Ra2 | CD4 | DAP12 | CD3δ |
| IL13Ra2 | CD4 | DAP12 | CD3γ |
| IL13Ra2 | CD4 | DAP12 | CD3ε |
| IL13Ra2 | CD4 | DAP12 | FcγRI-γ |
| IL13Ra2 | CD4 | DAP12 | FcγRIII-γ |
| IL13Ra2 | CD4 | DAP12 | FcεRIβ |
| IL13Ra2 | CD4 | DAP12 | FcεRIγ |
| IL13Ra2 | CD4 | DAP12 | DAP10 |
| IL13Ra2 | CD4 | DAP12 | DAP12 |
| IL13Ra2 | CD4 | DAP12 | CD32 |
| IL13Ra2 | CD4 | DAP12 | CD79a |

TABLE 3-continued

| Third Generation CARs | | | |
|---|---|---|---|
| ScFv | Co-stimulatory Signal | Co-stimulatory Signal | Signal Domain |
| IL13Ra2 | CD4 | DAP12 | CD79b |
| IL13Ra2 | CD4 | MyD88 | CD8 |
| IL13Ra2 | CD4 | MyD88 | CD3ζ |
| IL13Ra2 | CD4 | MyD88 | CD3δ |
| IL13Ra2 | CD4 | MyD88 | CD3γ |
| IL13Ra2 | CD4 | MyD88 | CD3ε |
| IL13Ra2 | CD4 | MyD88 | FcγRI-γ |
| IL13Ra2 | CD4 | MyD88 | FcγRIII-γ |
| IL13Ra2 | CD4 | MyD88 | FcεRIβ |
| IL13Ra2 | CD4 | MyD88 | FcεRIγ |
| IL13Ra2 | CD4 | MyD88 | DAP10 |
| IL13Ra2 | CD4 | MyD88 | DAP12 |
| IL13Ra2 | CD4 | MyD88 | CD32 |
| IL13Ra2 | CD4 | MyD88 | CD79a |
| IL13Ra2 | CD4 | MyD88 | CD79b |
| IL13Ra2 | CD4 | CD7 | CD8 |
| IL13Ra2 | CD4 | CD7 | CD3ζ |
| IL13Ra2 | CD4 | CD7 | CD3δ |
| IL13Ra2 | CD4 | CD7 | CD3γ |
| IL13Ra2 | CD4 | CD7 | CD3ε |
| IL13Ra2 | CD4 | CD7 | FcγRI-γ |
| IL13Ra2 | CD4 | CD7 | FcγRIII-γ |
| IL13Ra2 | CD4 | CD7 | FcεRIβ |
| IL13Ra2 | CD4 | CD7 | FcεRIγ |
| IL13Ra2 | CD4 | CD7 | DAP10 |
| IL13Ra2 | CD4 | CD7 | DAP12 |
| IL13Ra2 | CD4 | CD7 | CD32 |
| IL13Ra2 | CD4 | CD7 | CD79a |
| IL13Ra2 | CD4 | CD7 | CD79b |
| IL13Ra2 | CD4 | BTNL3 | CD8 |
| IL13Ra2 | CD4 | BTNL3 | CD3ζ |
| IL13Ra2 | CD4 | BTNL3 | CD3δ |
| IL13Ra2 | CD4 | BTNL3 | CD3γ |
| IL13Ra2 | CD4 | BTNL3 | CD3ε |
| IL13Ra2 | CD4 | BTNL3 | FcγRI-γ |
| IL13Ra2 | CD4 | BTNL3 | FcγRIII-γ |
| IL13Ra2 | CD4 | BTNL3 | FcεRIβ |
| IL13Ra2 | CD4 | BTNL3 | FcεRIγ |
| IL13Ra2 | CD4 | BTNL3 | DAP10 |
| IL13Ra2 | CD4 | BTNL3 | DAP12 |
| IL13Ra2 | CD4 | BTNL3 | CD32 |
| IL13Ra2 | CD4 | BTNL3 | CD79a |
| IL13Ra2 | CD4 | BTNL3 | CD79b |
| IL13Ra2 | CD4 | NKG2D | CD8 |
| IL13Ra2 | CD4 | NKG2D | CD3ζ |
| IL13Ra2 | CD4 | NKG2D | CD3δ |
| IL13Ra2 | CD4 | NKG2D | CD3γ |
| IL13Ra2 | CD4 | NKG2D | CD3ε |
| IL13Ra2 | CD4 | NKG2D | FcγRI-γ |
| IL13Ra2 | CD4 | NKG2D | FcγRIII-γ |
| IL13Ra2 | CD4 | NKG2D | FcεRIβ |
| IL13Ra2 | CD4 | NKG2D | FcεRIγ |
| IL13Ra2 | CD4 | NKG2D | DAP10 |
| IL13Ra2 | CD4 | NKG2D | DAP12 |
| IL13Ra2 | CD4 | NKG2D | CD32 |
| IL13Ra2 | CD4 | NKG2D | CD79a |
| IL13Ra2 | CD4 | NKG2D | CD79b |
| IL13Ra2 | b2c | CD28 | CD8 |
| IL13Ra2 | b2c | CD28 | CD3ζ |
| IL13Ra2 | b2c | CD28 | CD3δ |
| IL13Ra2 | b2c | CD28 | CD3γ |
| IL13Ra2 | b2c | CD28 | CD3ε |
| IL13Ra2 | b2c | CD28 | FcγRI-γ |
| IL13Ra2 | b2c | CD28 | FcγRIII-γ |
| IL13Ra2 | b2c | CD28 | FcεRIβ |
| IL13Ra2 | b2c | CD28 | FcεRIγ |
| IL13Ra2 | b2c | CD28 | DAP10 |
| IL13Ra2 | b2c | CD28 | DAP12 |
| IL13Ra2 | b2c | CD28 | CD32 |
| IL13Ra2 | b2c | CD28 | CD79b |
| IL13Ra2 | b2c | CD8 | CD8 |
| IL13Ra2 | b2c | CD8 | CD3ζ |
| IL13Ra2 | b2c | CD8 | CD3δ |
| IL13Ra2 | b2c | CD8 | CD3γ |
| IL13Ra2 | b2c | CD8 | CD3ε |
| IL13Ra2 | b2c | CD8 | FcγRI-γ |
| IL13Ra2 | b2c | CD8 | FcγRIII-γ |
| IL13Ra2 | b2c | CD8 | FcεRIβ |
| IL13Ra2 | b2c | CD8 | FcεRIγ |
| IL13Ra2 | b2c | CD8 | DAP10 |
| IL13Ra2 | b2c | CD8 | DAP12 |
| IL13Ra2 | b2c | CD8 | CD32 |
| IL13Ra2 | b2c | CD8 | CD79a |
| IL13Ra2 | b2c | CD8 | CD79b |
| IL13Ra2 | b2c | CD4 | CD8 |
| IL13Ra2 | b2c | CD4 | CD3ζ |
| IL13Ra2 | b2c | CD4 | CD3δ |
| IL13Ra2 | b2c | CD4 | CD3γ |
| IL13Ra2 | b2c | CD4 | CD3ε |
| IL13Ra2 | b2c | CD4 | FcγRI-γ |
| IL13Ra2 | b2c | CD4 | FcγRIII-γ |
| IL13Ra2 | b2c | CD4 | FcεRIβ |
| IL13Ra2 | b2c | CD4 | FcεRIγ |
| IL13Ra2 | b2c | CD4 | DAP10 |
| IL13Ra2 | b2c | CD4 | DAP12 |
| IL13Ra2 | b2c | CD4 | CD32 |
| IL13Ra2 | b2c | CD4 | CD79a |
| IL13Ra2 | b2c | CD4 | CD79b |
| IL13Ra2 | b2c | b2c | CD8 |
| IL13Ra2 | b2c | b2c | CD3ζ |
| IL13Ra2 | b2c | b2c | CD3δ |
| IL13Ra2 | b2c | b2c | CD3γ |
| IL13Ra2 | b2c | b2c | CD3ε |
| IL13Ra2 | b2c | b2c | FcγRI-γ |
| IL13Ra2 | b2c | b2c | FcγRIII-γ |
| IL13Ra2 | b2c | b2c | FcεRIβ |
| IL13Ra2 | b2c | b2c | FcεRIγ |
| IL13Ra2 | b2c | b2c | DAP10 |
| IL13Ra2 | b2c | b2c | DAP12 |
| IL13Ra2 | b2c | b2c | CD32 |
| IL13Ra2 | b2c | b2c | CD79a |
| IL13Ra2 | b2c | b2c | CD79b |
| IL13Ra2 | b2c | CD137/41BB | CD8 |
| IL13Ra2 | b2c | CD137/41BB | CD3ζ |
| IL13Ra2 | b2c | CD137/41BB | CD3δ |
| IL13Ra2 | b2c | CD137/41BB | CD3γ |
| IL13Ra2 | b2c | CD137/41BB | CD3ε |
| IL13Ra2 | b2c | CD137/41BB | FcγRI-γ |
| IL13Ra2 | b2c | CD137/41BB | FcγRIII-γ |
| IL13Ra2 | b2c | CD137/41BB | FcεRIβ |
| IL13Ra2 | b2c | CD137/41BB | FcεRIγ |
| IL13Ra2 | b2c | CD137/41BB | DAP10 |
| IL13Ra2 | b2c | CD137/41BB | DAP12 |
| IL13Ra2 | b2c | CD137/41BB | CD32 |
| IL13Ra2 | b2c | CD137/41BB | CD79a |
| IL13Ra2 | b2c | CD137/41BB | CD79b |
| IL13Ra2 | b2c | ICOS | CD8 |
| IL13Ra2 | b2c | ICOS | CD3ζ |
| IL13Ra2 | b2c | ICOS | CD3δ |
| IL13Ra2 | b2c | ICOS | CD3γ |
| IL13Ra2 | b2c | ICOS | CD3ε |
| IL13Ra2 | b2c | ICOS | FcγRI-γ |
| IL13Ra2 | b2c | ICOS | FcγRIII-γ |
| IL13Ra2 | b2c | ICOS | FcεRIβ |
| IL13Ra2 | b2c | ICOS | FcεRIγ |
| IL13Ra2 | b2c | ICOS | DAP10 |
| IL13Ra2 | b2c | ICOS | DAP12 |
| IL13Ra2 | b2c | ICOS | CD32 |
| IL13Ra2 | b2c | ICOS | CD79a |
| IL13Ra2 | b2c | ICOS | CD79b |
| IL13Ra2 | b2c | CD27 | CD8 |
| IL13Ra2 | b2c | CD27 | CD3ζ |
| IL13Ra2 | b2c | CD27 | CD3δ |
| IL13Ra2 | b2c | CD27 | CD3γ |
| IL13Ra2 | b2c | CD27 | CD3ε |
| IL13Ra2 | b2c | CD27 | FcγRI-γ |
| IL13Ra2 | b2c | CD27 | FcγRIII-γ |
| IL13Ra2 | b2c | CD27 | FcεRIβ |
| IL13Ra2 | b2c | CD27 | FcεRIγ |

TABLE 3-continued

Third Generation CARs

| ScFv | Co-stimulatory Signal | Co-stimulatory Signal | Signal Domain |
|---|---|---|---|
| IL13Ra2 | b2c | CD27 | DAP10 |
| IL13Ra2 | b2c | CD27 | DAP12 |
| IL13Ra2 | b2c | CD27 | CD32 |
| IL13Ra2 | b2c | CD27 | CD79a |
| IL13Ra2 | b2c | CD27 | CD79b |
| IL13Ra2 | b2c | CD28δ | CD8 |
| IL13Ra2 | b2c | CD28δ | CD3ζ |
| IL13Ra2 | b2c | CD28δ | CD3δ |
| IL13Ra2 | b2c | CD28δ | CD3γ |
| IL13Ra2 | b2c | CD28δ | CD3ε |
| IL13Ra2 | b2c | CD28δ | FcγRI-γ |
| IL13Ra2 | b2c | CD28δ | FcγRIII-γ |
| IL13Ra2 | b2c | CD28δ | FcεRIβ |
| IL13Ra2 | b2c | CD28δ | FcεRIγ |
| IL13Ra2 | b2c | CD28δ | DAP10 |
| IL13Ra2 | b2c | CD28δ | DAP12 |
| IL13Ra2 | b2c | CD28δ | CD32 |
| IL13Ra2 | b2c | CD28δ | CD79a |
| IL13Ra2 | b2c | CD28δ | CD79b |
| IL13Ra2 | b2c | CD80 | CD8 |
| IL13Ra2 | b2c | CD80 | CD3ζ |
| IL13Ra2 | b2c | CD80 | CD3δ |
| IL13Ra2 | b2c | CD80 | CD3γ |
| IL13Ra2 | b2c | CD80 | CD3ε |
| IL13Ra2 | b2c | CD80 | FcγRI-γ |
| IL13Ra2 | b2c | CD80 | FcγRIII-γ |
| IL13Ra2 | b2c | CD80 | FcεRIβ |
| IL13Ra2 | b2c | CD80 | FcεRIγ |
| IL13Ra2 | b2c | CD80 | DAP10 |
| IL13Ra2 | b2c | CD80 | DAP12 |
| IL13Ra2 | b2c | CD80 | CD32 |
| IL13Ra2 | b2c | CD80 | CD79a |
| IL13Ra2 | b2c | CD80 | CD79b |
| IL13Ra2 | b2c | CD86 | CD8 |
| IL13Ra2 | b2c | CD86 | CD3ζ |
| IL13Ra2 | b2c | CD86 | CD3δ |
| IL13Ra2 | b2c | CD86 | CD3γ |
| IL13Ra2 | b2c | CD86 | CD3ε |
| IL13Ra2 | b2c | CD86 | FcγRI-γ |
| IL13Ra2 | b2c | CD86 | FcγRIII-γ |
| IL13Ra2 | b2c | CD86 | FcεRIβ |
| IL13Ra2 | b2c | CD86 | FcεRIγ |
| IL13Ra2 | b2c | CD86 | DAP10 |
| IL13Ra2 | b2c | CD86 | DAP12 |
| IL13Ra2 | b2c | CD86 | CD32 |
| IL13Ra2 | b2c | CD86 | CD79a |
| IL13Ra2 | b2c | CD86 | CD79b |
| IL13Ra2 | b2c | OX40 | CD8 |
| IL13Ra2 | b2c | OX40 | CD3ζ |
| IL13Ra2 | b2c | OX40 | CD3δ |
| IL13Ra2 | b2c | OX40 | CD3γ |
| IL13Ra2 | b2c | OX40 | CD3ε |
| IL13Ra2 | b2c | OX40 | FcγRI-γ |
| IL13Ra2 | b2c | OX40 | FcγRIII-γ |
| IL13Ra2 | b2c | OX40 | FcεRIβ |
| IL13Ra2 | b2c | OX40 | FcεRIγ |
| IL13Ra2 | b2c | OX40 | DAP10 |
| IL13Ra2 | b2c | OX40 | DAP12 |
| IL13Ra2 | b2c | OX40 | CD32 |
| IL13Ra2 | b2c | OX40 | CD79a |
| IL13Ra2 | b2c | OX40 | CD79b |
| IL13Ra2 | b2c | DAP10 | CD8 |
| IL13Ra2 | b2c | DAP10 | CD3ζ |
| IL13Ra2 | b2c | DAP10 | CD3δ |
| IL13Ra2 | b2c | DAP10 | CD3γ |
| IL13Ra2 | b2c | DAP10 | CD3ε |
| IL13Ra2 | b2c | DAP10 | FcγRI-γ |
| IL13Ra2 | b2c | DAP10 | FcγRIII-γ |
| IL13Ra2 | b2c | DAP10 | FcεRIβ |
| IL13Ra2 | b2c | DAP10 | FcεRIγ |
| IL13Ra2 | b2c | DAP10 | DAP10 |
| IL13Ra2 | b2c | DAP10 | DAP12 |
| IL13Ra2 | b2c | DAP10 | CD32 |
| IL13Ra2 | b2c | DAP10 | CD79a |
| IL13Ra2 | b2c | DAP10 | CD79b |
| IL13Ra2 | b2c | DAP12 | CD8 |
| IL13Ra2 | b2c | DAP12 | CD3ζ |
| IL13Ra2 | b2c | DAP12 | CD3δ |
| IL13Ra2 | b2c | DAP12 | CD3γ |
| IL13Ra2 | b2c | DAP12 | CD3ε |
| IL13Ra2 | b2c | DAP12 | FcγRI-γ |
| IL13Ra2 | b2c | DAP12 | FcγRIII-γ |
| IL13Ra2 | b2c | DAP12 | FcεRIβ |
| IL13Ra2 | b2c | DAP12 | FcεRIγ |
| IL13Ra2 | b2c | DAP12 | DAP10 |
| IL13Ra2 | b2c | DAP12 | DAP12 |
| IL13Ra2 | b2c | DAP12 | CD32 |
| IL13Ra2 | b2c | DAP12 | CD79a |
| IL13Ra2 | b2c | DAP12 | CD79b |
| IL13Ra2 | b2c | MyD88 | CD8 |
| IL13Ra2 | b2c | MyD88 | CD3ζ |
| IL13Ra2 | b2c | MyD88 | CD3δ |
| IL13Ra2 | b2c | MyD88 | CD3γ |
| IL13Ra2 | b2c | MyD88 | CD3ε |
| IL13Ra2 | b2c | MyD88 | FcγRI-γ |
| IL13Ra2 | b2c | MyD88 | FcγRIII-γ |
| IL13Ra2 | b2c | MyD88 | FcεRIβ |
| IL13Ra2 | b2c | MyD88 | FcεRIγ |
| IL13Ra2 | b2c | MyD88 | DAP10 |
| IL13Ra2 | b2c | MyD88 | DAP12 |
| IL13Ra2 | b2c | MyD88 | CD32 |
| IL13Ra2 | b2c | MyD88 | CD79a |
| IL13Ra2 | b2c | MyD88 | CD79b |
| IL13Ra2 | b2c | CD7 | CD8 |
| IL13Ra2 | b2c | CD7 | CD3ζ |
| IL13Ra2 | b2c | CD7 | CD3δ |
| IL13Ra2 | b2c | CD7 | CD3γ |
| IL13Ra2 | b2c | CD7 | CD3ε |
| IL13Ra2 | b2c | CD7 | FcγRI-γ |
| IL13Ra2 | b2c | CD7 | FcγRIII-γ |
| IL13Ra2 | b2c | CD7 | FcεRIβ |
| IL13Ra2 | b2c | CD7 | FcεRIγ |
| IL13Ra2 | b2c | CD7 | DAP10 |
| IL13Ra2 | b2c | CD7 | DAP12 |
| IL13Ra2 | b2c | CD7 | CD32 |
| IL13Ra2 | b2c | CD7 | CD79a |
| IL13Ra2 | b2c | CD7 | CD79b |
| IL13Ra2 | b2c | BTNL3 | CD8 |
| IL13Ra2 | b2c | BTNL3 | CD3ζ |
| IL13Ra2 | b2c | BTNL3 | CD3δ |
| IL13Ra2 | b2c | BTNL3 | CD3γ |
| IL13Ra2 | b2c | BTNL3 | CD3ε |
| IL13Ra2 | b2c | BTNL3 | FcγRI-γ |
| IL13Ra2 | b2c | BTNL3 | FcγRIII-γ |
| IL13Ra2 | b2c | BTNL3 | FcεRIβ |
| IL13Ra2 | b2c | BTNL3 | FcεRIγ |
| IL13Ra2 | b2c | BTNL3 | DAP10 |
| IL13Ra2 | b2c | BTNL3 | DAP12 |
| IL13Ra2 | b2c | BTNL3 | CD32 |
| IL13Ra2 | b2c | BTNL3 | CD79a |
| IL13Ra2 | b2c | BTNL3 | CD79b |
| IL13Ra2 | b2c | NKG2D | CD8 |
| IL13Ra2 | b2c | NKG2D | CD3ζ |
| IL13Ra2 | b2c | NKG2D | CD3δ |
| IL13Ra2 | b2c | NKG2D | CD3γ |
| IL13Ra2 | b2c | NKG2D | CD3ε |
| IL13Ra2 | b2c | NKG2D | FcγRI-γ |
| IL13Ra2 | b2c | NKG2D | FcγRIII-γ |
| IL13Ra2 | b2c | NKG2D | FcεRIβ |
| IL13Ra2 | b2c | NKG2D | FcεRIγ |
| IL13Ra2 | b2c | NKG2D | DAP10 |
| IL13Ra2 | b2c | NKG2D | DAP12 |
| IL13Ra2 | b2c | NKG2D | CD32 |
| IL13Ra2 | b2c | NKG2D | CD79a |
| IL13Ra2 | b2c | NKG2D | CD79b |
| IL13Ra2 | CD137/41BB | CD28 | CD8 |
| IL13Ra2 | CD137/41BB | CD28 | CD3ζ |
| IL13Ra2 | CD137/41BB | CD28 | CD3δ |
| IL13Ra2 | CD137/41BB | CD28 | CD3γ |
| IL13Ra2 | CD137/41BB | CD28 | CD3ε |

TABLE 3-continued

Third Generation CARs

| ScFv | Co-stimulatory Signal | Co-stimulatory Signal | Signal Domain |
|---|---|---|---|
| IL13Ra2 | CD137/41BB | CD28 | FcγRI-γ |
| IL13Ra2 | CD137/41BB | CD28 | FcγRIII-γ |
| IL13Ra2 | CD137/41BB | CD28 | FcεRIβ |
| IL13Ra2 | CD137/41BB | CD28 | FcεRIγ |
| IL13Ra2 | CD137/41BB | CD28 | DAP10 |
| IL13Ra2 | CD137/41BB | CD28 | DAP12 |
| IL13Ra2 | CD137/41BB | CD28 | CD32 |
| IL13Ra2 | CD137/41BB | CD28 | CD79a |
| IL13Ra2 | CD137/41BB | CD28 | CD79b |
| IL13Ra2 | CD137/41BB | CD8 | CD8 |
| IL13Ra2 | CD137/41BB | CD8 | CD3ζ |
| IL13Ra2 | CD137/41BB | CD8 | CD3δ |
| IL13Ra2 | CD137/41BB | CD8 | CD3γ |
| IL13Ra2 | CD137/41BB | CD8 | CD3ε |
| IL13Ra2 | CD137/41BB | CD8 | FcγRI-γ |
| IL13Ra2 | CD137/41BB | CD8 | FcγRIII-γ |
| IL13Ra2 | CD137/41BB | CD8 | FcεRIβ |
| IL13Ra2 | CD137/41BB | CD8 | FcεRIγ |
| IL13Ra2 | CD137/41BB | CD8 | DAP10 |
| IL13Ra2 | CD137/41BB | CD8 | DAP12 |
| IL13Ra2 | CD137/41BB | CD8 | CD32 |
| IL13Ra2 | CD137/41BB | CD8 | CD79a |
| IL13Ra2 | CD137/41BB | CD8 | CD79b |
| IL13Ra2 | CD137/41BB | CD4 | CD8 |
| IL13Ra2 | CD137/41BB | CD4 | CD3ζ |
| IL13Ra2 | CD137/41BB | CD4 | CD3δ |
| IL13Ra2 | CD137/41BB | CD4 | CD3γ |
| IL13Ra2 | CD137/41BB | CD4 | CD3ε |
| IL13Ra2 | CD137/41BB | CD4 | FcγRI-γ |
| IL13Ra2 | CD137/41BB | CD4 | FcγRIII-γ |
| IL13Ra2 | CD137/41BB | CD4 | FcεRIβ |
| IL13Ra2 | CD137/41BB | CD4 | FcεRIγ |
| IL13Ra2 | CD137/41BB | CD4 | DAP10 |
| IL13Ra2 | CD137/41BB | CD4 | DAP12 |
| IL13Ra2 | CD137/41BB | CD4 | CD32 |
| IL13Ra2 | CD137/41BB | CD4 | CD79a |
| IL13Ra2 | CD137/41BB | CD4 | CD79b |
| IL13Ra2 | CD137/41BB | b2c | CD8 |
| IL13Ra2 | CD137/41BB | b2c | CD3ζ |
| IL13Ra2 | CD137/41BB | b2c | CD3δ |
| IL13Ra2 | CD137/41BB | b2c | CD3γ |
| IL13Ra2 | CD137/41BB | b2c | CD3ε |
| IL13Ra2 | CD137/41BB | b2c | FcγRI-γ |
| IL13Ra2 | CD137/41BB | b2c | FcγRIII-γ |
| IL13Ra2 | CD137/41BB | b2c | FcεRIβ |
| IL13Ra2 | CD137/41BB | b2c | FcεRIγ |
| IL13Ra2 | CD137/41BB | b2c | DAP10 |
| IL13Ra2 | CD137/41BB | b2c | DAP12 |
| IL13Ra2 | CD137/41BB | b2c | CD32 |
| IL13Ra2 | CD137/41BB | b2c | CD79a |
| IL13Ra2 | CD137/41BB | b2c | CD79b |
| IL13Ra2 | CD137/41BB | CD137/41BB | CD8 |
| IL13Ra2 | CD137/41BB | CD137/41BB | CD3ζ |
| IL13Ra2 | CD137/41BB | CD137/41BB | CD3δ |
| IL13Ra2 | CD137/41BB | CD137/41BB | CD3γ |
| IL13Ra2 | CD137/41BB | CD137/41BB | CD3ε |
| IL13Ra2 | CD137/41BB | CD137/41BB | FcγRI-γ |
| IL13Ra2 | CD137/41BB | CD137/41BB | FcγRIII-γ |
| IL13Ra2 | CD137/41BB | CD137/41BB | FcεRIβ |
| IL13Ra2 | CD137/41BB | CD137/41BB | FcεRIγ |
| IL13Ra2 | CD137/41BB | CD137/41BB | DAP10 |
| IL13Ra2 | CD137/41BB | CD137/41BB | DAP12 |
| IL13Ra2 | CD137/41BB | CD137/41BB | CD32 |
| IL13Ra2 | CD137/41BB | CD137/41BB | CD79a |
| IL13Ra2 | CD137/41BB | CD137/41BB | CD79b |
| IL13Ra2 | CD137/41BB | ICOS | CD8 |
| IL13Ra2 | CD137/41BB | ICOS | CD3ζ |
| IL13Ra2 | CD137/41BB | ICOS | CD3δ |
| IL13Ra2 | CD137/41BB | ICOS | CD3γ |
| IL13Ra2 | CD137/41BB | ICOS | CD3ε |
| IL13Ra2 | CD137/41BB | ICOS | FcγRI-γ |
| IL13Ra2 | CD137/41BB | ICOS | FcγRIII-γ |
| IL13Ra2 | CD137/41BB | ICOS | FcεRIβ |
| IL13Ra2 | CD137/41BB | ICOS | FcεRIγ |
| IL13Ra2 | CD137/41BB | ICOS | DAP10 |
| IL13Ra2 | CD137/41BB | ICOS | DAP12 |
| IL13Ra2 | CD137/41BB | ICOS | CD32 |
| IL13Ra2 | CD137/41BB | ICOS | CD79a |
| IL13Ra2 | CD137/41BB | ICOS | CD79b |
| IL13Ra2 | CD137/41BB | CD27 | CD8 |
| IL13Ra2 | CD137/41BB | CD27 | CD3ζ |
| IL13Ra2 | CD137/41BB | CD27 | CD3δ |
| IL13Ra2 | CD137/41BB | CD27 | CD3γ |
| IL13Ra2 | CD137/41BB | CD27 | CD3ε |
| IL13Ra2 | CD137/41BB | CD27 | FcγRI-γ |
| IL13Ra2 | CD137/41BB | CD27 | FcγRIII-γ |
| IL13Ra2 | CD137/41BB | CD27 | FcεRIβ |
| IL13Ra2 | CD137/41BB | CD27 | FcεRIγ |
| IL13Ra2 | CD137/41BB | CD27 | DAP10 |
| IL13Ra2 | CD137/41BB | CD27 | DAP12 |
| IL13Ra2 | CD137/41BB | CD27 | CD32 |
| IL13Ra2 | CD137/41BB | CD27 | CD79a |
| IL13Ra2 | CD137/41BB | CD27 | CD79b |
| IL13Ra2 | CD137/41BB | CD28δ | CD8 |
| IL13Ra2 | CD137/41BB | CD28δ | CD3ζ |
| IL13Ra2 | CD137/41BB | CD28δ | CD3δ |
| IL13Ra2 | CD137/41BB | CD28δ | CD3γ |
| IL13Ra2 | CD137/41BB | CD28δ | CD3ε |
| IL13Ra2 | CD137/41BB | CD28δ | FcγRI-γ |
| IL13Ra2 | CD137/41BB | CD28δ | FcγRIII-γ |
| IL13Ra2 | CD137/41BB | CD28δ | FcεRIβ |
| IL13Ra2 | CD137/41BB | CD28δ | FcεRIγ |
| IL13Ra2 | CD137/41BB | CD28δ | DAP10 |
| IL13Ra2 | CD137/41BB | CD28δ | DAP12 |
| IL13Ra2 | CD137/41BB | CD28δ | CD32 |
| IL13Ra2 | CD137/41BB | CD28δ | CD79a |
| IL13Ra2 | CD137/41BB | CD28δ | CD79b |
| IL13Ra2 | CD137/41BB | CD80 | CD8 |
| IL13Ra2 | CD137/41BB | CD80 | CD3ζ |
| IL13Ra2 | CD137/41BB | CD80 | CD3δ |
| IL13Ra2 | CD137/41BB | CD80 | CD3γ |
| IL13Ra2 | CD137/41BB | CD80 | CD3ε |
| IL13Ra2 | CD137/41BB | CD80 | FcγRI-γ |
| IL13Ra2 | CD137/41BB | CD80 | FcγRIII-γ |
| IL13Ra2 | CD137/41BB | CD80 | FcεRIβ |
| IL13Ra2 | CD137/41BB | CD80 | FcεRIγ |
| IL13Ra2 | CD137/41BB | CD80 | DAP10 |
| IL13Ra2 | CD137/41BB | CD80 | DAP12 |
| IL13Ra2 | CD137/41BB | CD80 | CD32 |
| IL13Ra2 | CD137/41BB | CD80 | CD79a |
| IL13Ra2 | CD137/41BB | CD80 | CD79b |
| IL13Ra2 | CD137/41BB | CD86 | CD8 |
| IL13Ra2 | CD137/41BB | CD86 | CD3ζ |
| IL13Ra2 | CD137/41BB | CD86 | CD3δ |
| IL13Ra2 | CD137/41BB | CD86 | CD3γ |
| IL13Ra2 | CD137/41BB | CD86 | CD3ε |
| IL13Ra2 | CD137/41BB | CD86 | FcγRI-γ |
| IL13Ra2 | CD137/41BB | CD86 | FcγRIII-γ |
| IL13Ra2 | CD137/41BB | CD86 | FcεRIβ |
| IL13Ra2 | CD137/41BB | CD86 | FcεRIγ |
| IL13Ra2 | CD137/41BB | CD86 | DAP10 |
| IL13Ra2 | CD137/41BB | CD86 | DAP12 |
| IL13Ra2 | CD137/41BB | CD86 | CD32 |
| IL13Ra2 | CD137/41BB | CD86 | CD79a |
| IL13Ra2 | CD137/41BB | CD86 | CD79b |
| IL13Ra2 | CD137/41BB | OX40 | CD8 |
| IL13Ra2 | CD137/41BB | OX40 | CD3ζ |
| IL13Ra2 | CD137/41BB | OX40 | CD3δ |
| IL13Ra2 | CD137/41BB | OX40 | CD3γ |
| IL13Ra2 | CD137/41BB | OX40 | CD3ε |
| IL13Ra2 | CD137/41BB | OX40 | FcγRI-γ |
| IL13Ra2 | CD137/41BB | OX40 | FcγRIII-γ |
| IL13Ra2 | CD137/41BB | OX40 | FcεRIβ |
| IL13Ra2 | CD137/41BB | OX40 | FcεRIγ |
| IL13Ra2 | CD137/41BB | OX40 | DAP10 |
| IL13Ra2 | CD137/41BB | OX40 | DAP12 |
| IL13Ra2 | CD137/41BB | OX40 | CD32 |
| IL13Ra2 | CD137/41BB | OX40 | CD79a |
| IL13Ra2 | CD137/41BB | OX40 | CD79b |
| IL13Ra2 | CD137/41BB | DAP10 | CD8 |

TABLE 3-continued

Third Generation CARs

| ScFv | Co-stimulatory Signal | Co-stimulatory Signal | Signal Domain |
|---|---|---|---|
| IL13Ra2 | CD137/41BB | DAP10 | CD3ζ |
| IL13Ra2 | CD137/41BB | DAP10 | CD3δ |
| IL13Ra2 | CD137/41BB | DAP10 | CD3γ |
| IL13Ra2 | CD137/41BB | DAP10 | CD3ε |
| IL13Ra2 | CD137/41BB | DAP10 | FcγRI-γ |
| IL13Ra2 | CD137/41BB | DAP10 | FcγRIII-γ |
| IL13Ra2 | CD137/41BB | DAP10 | FcεRIβ |
| IL13Ra2 | CD137/41BB | DAP10 | FcεRIγ |
| IL13Ra2 | CD137/41BB | DAP10 | DAP10 |
| IL13Ra2 | CD137/41BB | DAP10 | DAP12 |
| IL13Ra2 | CD137/41BB | DAP10 | CD32 |
| IL13Ra2 | CD137/41BB | DAP10 | CD79a |
| IL13Ra2 | CD137/41BB | DAP10 | CD79b |
| IL13Ra2 | CD137/41BB | DAP12 | CD8 |
| IL13Ra2 | CD137/41BB | DAP12 | CD3ζ |
| IL13Ra2 | CD137/41BB | DAP12 | CD3δ |
| IL13Ra2 | CD137/41BB | DAP12 | CD3γ |
| IL13Ra2 | CD137/41BB | DAP12 | CD3ε |
| IL13Ra2 | CD137/41BB | DAP12 | FcγRI-γ |
| IL13Ra2 | CD137/41BB | DAP12 | FcγRIII-γ |
| IL13Ra2 | CD137/41BB | DAP12 | FcεRIβ |
| IL13Ra2 | CD137/41BB | DAP12 | FcεRIγ |
| IL13Ra2 | CD137/41BB | DAP12 | DAP10 |
| IL13Ra2 | CD137/41BB | DAP12 | DAP12 |
| IL13Ra2 | CD137/41BB | DAP12 | CD32 |
| IL13Ra2 | CD137/41BB | DAP12 | CD79a |
| IL13Ra2 | CD137/41BB | DAP12 | CD79b |
| IL13Ra2 | CD137/41BB | MyD88 | CD8 |
| IL13Ra2 | CD137/41BB | MyD88 | CD3ζ |
| IL13Ra2 | CD137/41BB | MyD88 | CD3δ |
| IL13Ra2 | CD137/41BB | MyD88 | CD3γ |
| IL13Ra2 | CD137/41BB | MyD88 | CD3ε |
| IL13Ra2 | CD137/41BB | MyD88 | FcγRI-γ |
| IL13Ra2 | CD137/41BB | MyD88 | FcγRIII-γ |
| IL13Ra2 | CD137/41BB | MyD88 | FcεRIβ |
| IL13Ra2 | CD137/41BB | MyD88 | FcεRIγ |
| IL13Ra2 | CD137/41BB | MyD88 | DAP10 |
| IL13Ra2 | CD137/41BB | MyD88 | DAP12 |
| IL13Ra2 | CD137/41BB | MyD88 | CD32 |
| IL13Ra2 | CD137/41BB | MyD88 | CD79a |
| IL13Ra2 | CD137/41BB | MyD88 | CD79b |
| IL13Ra2 | CD137/41BB | CD7 | CD8 |
| IL13Ra2 | CD137/41BB | CD7 | CD3ζ |
| IL13Ra2 | CD137/41BB | CD7 | CD3δ |
| IL13Ra2 | CD137/41BB | CD7 | CD3γ |
| IL13Ra2 | CD137/41BB | CD7 | CD3ε |
| IL13Ra2 | CD137/41BB | CD7 | FcγRI-γ |
| IL13Ra2 | CD137/41BB | CD7 | FcγRIII-γ |
| IL13Ra2 | CD137/41BB | CD7 | FcεRIβ |
| IL13Ra2 | CD137/41BB | CD7 | FcεRIγ |
| IL13Ra2 | CD137/41BB | CD7 | DAP10 |
| IL13Ra2 | CD137/41BB | CD7 | DAP12 |
| IL13Ra2 | CD137/41BB | CD7 | CD32 |
| IL13Ra2 | CD137/41BB | CD7 | CD79a |
| IL13Ra2 | CD137/41BB | CD7 | CD79b |
| IL13Ra2 | CD137/41BB | BTNL3 | CD8 |
| IL13Ra2 | CD137/41BB | BTNL3 | CD3ζ |
| IL13Ra2 | CD137/41BB | BTNL3 | CD3δ |
| IL13Ra2 | CD137/41BB | BTNL3 | CD3γ |
| IL13Ra2 | CD137/41BB | BTNL3 | CD3ε |
| IL13Ra2 | CD137/41BB | BTNL3 | FcγRI-γ |
| IL13Ra2 | CD137/41BB | BTNL3 | FcγRIII-γ |
| IL13Ra2 | CD137/41BB | BTNL3 | FcεRIβ |
| IL13Ra2 | CD137/41BB | BTNL3 | FcεRIγ |
| IL13Ra2 | CD137/41BB | BTNL3 | DAP10 |
| IL13Ra2 | CD137/41BB | BTNL3 | DAP12 |
| IL13Ra2 | CD137/41BB | BTNL3 | CD32 |
| IL13Ra2 | CD137/41BB | BTNL3 | CD79a |
| IL13Ra2 | CD137/41BB | BTNL3 | CD79b |
| IL13Ra2 | CD137/41BB | NKG2D | CD8 |
| IL13Ra2 | CD137/41BB | NKG2D | CD3ζ |
| IL13Ra2 | CD137/41BB | NKG2D | CD3δ |
| IL13Ra2 | CD137/41BB | NKG2D | CD3γ |
| IL13Ra2 | CD137/41BB | NKG2D | CD3ε |
| IL13Ra2 | CD137/41BB | NKG2D | FcγRI-γ |
| IL13Ra2 | CD137/41BB | NKG2D | FcγRIII-γ |
| IL13Ra2 | CD137/41BB | NKG2D | FcεRIβ |
| IL13Ra2 | CD137/41BB | NKG2D | FcεRIγ |
| IL13Ra2 | CD137/41BB | NKG2D | DAP10 |
| IL13Ra2 | CD137/41BB | NKG2D | DAP12 |
| IL13Ra2 | CD137/41BB | NKG2D | CD32 |
| IL13Ra2 | CD137/41BB | NKG2D | CD79a |
| IL13Ra2 | CD137/41BB | NKG2D | CD79b |
| IL13Ra2 | ICOS | CD28 | CD8 |
| IL13Ra2 | ICOS | CD28 | CD3ζ |
| IL13Ra2 | ICOS | CD28 | CD3δ |
| IL13Ra2 | ICOS | CD28 | CD3γ |
| IL13Ra2 | ICOS | CD28 | CD3ε |
| IL13Ra2 | ICOS | CD28 | FcγRI-γ |
| IL13Ra2 | ICOS | CD28 | FcγRIII-γ |
| IL13Ra2 | ICOS | CD28 | FcεRIβ |
| IL13Ra2 | ICOS | CD28 | FcεRIγ |
| IL13Ra2 | ICOS | CD28 | DAP10 |
| IL13Ra2 | ICOS | CD28 | DAP12 |
| IL13Ra2 | ICOS | CD28 | CD32 |
| IL13Ra2 | ICOS | CD28 | CD79a |
| IL13Ra2 | ICOS | CD28 | CD79b |
| IL13Ra2 | ICOS | CD8 | CD8 |
| IL13Ra2 | ICOS | CD8 | CD3ζ |
| IL13Ra2 | ICOS | CD8 | CD3δ |
| IL13Ra2 | ICOS | CD8 | CD3γ |
| IL13Ra2 | ICOS | CD8 | CD3ε |
| IL13Ra2 | ICOS | CD8 | FcγRI-γ |
| IL13Ra2 | ICOS | CD8 | FcγRIII-γ |
| IL13Ra2 | ICOS | CD8 | FcεRIβ |
| IL13Ra2 | ICOS | CD8 | FcεRIγ |
| IL13Ra2 | ICOS | CD8 | DAP10 |
| IL13Ra2 | ICOS | CD8 | DAP12 |
| IL13Ra2 | ICOS | CD8 | CD32 |
| IL13Ra2 | ICOS | CD8 | CD79a |
| IL13Ra2 | ICOS | CD8 | CD79b |
| IL13Ra2 | ICOS | CD4 | CD8 |
| IL13Ra2 | ICOS | CD4 | CD3ζ |
| IL13Ra2 | ICOS | CD4 | CD3δ |
| IL13Ra2 | ICOS | CD4 | CD3γ |
| IL13Ra2 | ICOS | CD4 | CD3ε |
| IL13Ra2 | ICOS | CD4 | FcγRI-γ |
| IL13Ra2 | ICOS | CD4 | FcγRIII-γ |
| IL13Ra2 | ICOS | CD4 | FcεRIβ |
| IL13Ra2 | ICOS | CD4 | FcεRIγ |
| IL13Ra2 | ICOS | CD4 | DAP10 |
| IL13Ra2 | ICOS | CD4 | DAP12 |
| IL13Ra2 | ICOS | CD4 | CD32 |
| IL13Ra2 | ICOS | CD4 | CD79a |
| IL13Ra2 | ICOS | CD4 | CD79b |
| IL13Ra2 | ICOS | b2c | CD8 |
| IL13Ra2 | ICOS | b2c | CD3ζ |
| IL13Ra2 | ICOS | b2c | CD3δ |
| IL13Ra2 | ICOS | b2c | CD3γ |
| IL13Ra2 | ICOS | b2c | CD3ε |
| IL13Ra2 | ICOS | b2c | FcγRI-γ |
| IL13Ra2 | ICOS | b2c | FcγRIII-γ |
| IL13Ra2 | ICOS | b2c | FcεRIβ |
| IL13Ra2 | ICOS | b2c | FcεRIγ |
| IL13Ra2 | ICOS | b2c | DAP10 |
| IL13Ra2 | ICOS | b2c | DAP12 |
| IL13Ra2 | ICOS | b2c | CD32 |
| IL13Ra2 | ICOS | b2c | CD79a |
| IL13Ra2 | ICOS | b2c | CD79b |
| IL13Ra2 | ICOS | CD137/41BB | CD8 |
| IL13Ra2 | ICOS | CD137/41BB | CD3ζ |
| IL13Ra2 | ICOS | CD137/41BB | CD3δ |
| IL13Ra2 | ICOS | CD137/41BB | CD3γ |
| IL13Ra2 | ICOS | CD137/41BB | CD3ε |
| IL13Ra2 | ICOS | CD137/41BB | FcγRI-γ |
| IL13Ra2 | ICOS | CD137/41BB | FcγRIII-γ |
| IL13Ra2 | ICOS | CD137/41BB | FcεRIβ |
| IL13Ra2 | ICOS | CD137/41BB | FcεRIγ |
| IL13Ra2 | ICOS | CD137/41BB | DAP10 |
| IL13Ra2 | ICOS | CD137/41BB | DAP12 |

TABLE 3-continued

Third Generation CARs

| ScFv | Co-stimulatory Signal | Co-stimulatory Signal | Signal Domain |
|---|---|---|---|
| IL13Ra2 | ICOS | CD137/41BB | CD32 |
| IL13Ra2 | ICOS | CD137/41BB | CD79a |
| IL13Ra2 | ICOS | CD137/41BB | CD79b |
| IL13Ra2 | ICOS | ICOS | CD8 |
| IL13Ra2 | ICOS | ICOS | CD3ζ |
| IL13Ra2 | ICOS | ICOS | CD3δ |
| IL13Ra2 | ICOS | ICOS | CD3γ |
| IL13Ra2 | ICOS | ICOS | CD3ε |
| IL13Ra2 | ICOS | ICOS | FcγRI-γ |
| IL13Ra2 | ICOS | ICOS | FcγRIII-γ |
| IL13Ra2 | ICOS | ICOS | FcεRIβ |
| IL13Ra2 | ICOS | ICOS | FcεRIγ |
| IL13Ra2 | ICOS | ICOS | DAP10 |
| IL13Ra2 | ICOS | ICOS | DAP12 |
| IL13Ra2 | ICOS | ICOS | CD32 |
| IL13Ra2 | ICOS | ICOS | CD79a |
| IL13Ra2 | ICOS | ICOS | CD79b |
| IL13Ra2 | ICOS | CD27 | CD8 |
| IL13Ra2 | ICOS | CD27 | CD3ζ |
| IL13Ra2 | ICOS | CD27 | CD3δ |
| IL13Ra2 | ICOS | CD27 | CD3γ |
| IL13Ra2 | ICOS | CD27 | CD3ε |
| IL13Ra2 | ICOS | CD27 | FcγRI-γ |
| IL13Ra2 | ICOS | CD27 | FcγRIII-γ |
| IL13Ra2 | ICOS | CD27 | FcεRIβ |
| IL13Ra2 | ICOS | CD27 | FcεRIγ |
| IL13Ra2 | ICOS | CD27 | DAP10 |
| IL13Ra2 | ICOS | CD27 | DAP12 |
| IL13Ra2 | ICOS | CD27 | CD32 |
| IL13Ra2 | ICOS | CD27 | CD79a |
| IL13Ra2 | ICOS | CD27 | CD79b |
| IL13Ra2 | ICOS | CD28δ | CD8 |
| IL13Ra2 | ICOS | CD28δ | CD3ζ |
| IL13Ra2 | ICOS | CD28δ | CD3δ |
| IL13Ra2 | ICOS | CD28δ | CD3γ |
| IL13Ra2 | ICOS | CD28δ | CD3ε |
| IL13Ra2 | ICOS | CD28δ | FcγRI-γ |
| IL13Ra2 | ICOS | CD28δ | FcγRIII-γ |
| IL13Ra2 | ICOS | CD28δ | FcεRIβ |
| IL13Ra2 | ICOS | CD28δ | FcεRIγ |
| IL13Ra2 | ICOS | CD28δ | DAP10 |
| IL13Ra2 | ICOS | CD28δ | DAP12 |
| IL13Ra2 | ICOS | CD28δ | CD32 |
| IL13Ra2 | ICOS | CD28δ | CD79a |
| IL13Ra2 | ICOS | CD28δ | CD79b |
| IL13Ra2 | ICOS | CD80 | CD8 |
| IL13Ra2 | ICOS | CD80 | CD3ζ |
| IL13Ra2 | ICOS | CD80 | CD3δ |
| IL13Ra2 | ICOS | CD80 | CD3γ |
| IL13Ra2 | ICOS | CD80 | CD3ε |
| IL13Ra2 | ICOS | CD80 | FcγRI-γ |
| IL13Ra2 | ICOS | CD80 | FcγRIII-γ |
| IL13Ra2 | ICOS | CD80 | FcεRIβ |
| IL13Ra2 | ICOS | CD80 | FcεRIγ |
| IL13Ra2 | ICOS | CD80 | DAP10 |
| IL13Ra2 | ICOS | CD80 | DAP12 |
| IL13Ra2 | ICOS | CD80 | CD32 |
| IL13Ra2 | ICOS | CD80 | CD79a |
| IL13Ra2 | ICOS | CD80 | CD79b |
| IL13Ra2 | ICOS | CD86 | CD8 |
| IL13Ra2 | ICOS | CD86 | CD3ζ |
| IL13Ra2 | ICOS | CD86 | CD3δ |
| IL13Ra2 | ICOS | CD86 | CD3γ |
| IL13Ra2 | ICOS | CD86 | CD3ε |
| IL13Ra2 | ICOS | CD86 | FcγRI-γ |
| IL13Ra2 | ICOS | CD86 | FcγRIII-γ |
| IL13Ra2 | ICOS | CD86 | FcεRIβ |
| IL13Ra2 | ICOS | CD86 | FcεRIγ |
| IL13Ra2 | ICOS | CD86 | DAP10 |
| IL13Ra2 | ICOS | CD86 | DAP12 |
| IL13Ra2 | ICOS | CD86 | CD32 |
| IL13Ra2 | ICOS | CD86 | CD79a |
| IL13Ra2 | ICOS | CD86 | CD79b |
| IL13Ra2 | ICOS | OX40 | CD8 |
| IL13Ra2 | ICOS | OX40 | CD3ζ |
| IL13Ra2 | ICOS | OX40 | CD3δ |
| IL13Ra2 | ICOS | OX40 | CD3γ |
| IL13Ra2 | ICOS | OX40 | CD3ε |
| IL13Ra2 | ICOS | OX40 | FcγRI-γ |
| IL13Ra2 | ICOS | OX40 | FcγRIII-γ |
| IL13Ra2 | ICOS | OX40 | FcεRIβ |
| IL13Ra2 | ICOS | OX40 | FcεRIγ |
| IL13Ra2 | ICOS | OX40 | DAP10 |
| IL13Ra2 | ICOS | OX40 | DAP12 |
| IL13Ra2 | ICOS | OX40 | CD32 |
| IL13Ra2 | ICOS | OX40 | CD79a |
| IL13Ra2 | ICOS | OX40 | CD79b |
| IL13Ra2 | ICOS | DAP10 | CD8 |
| IL13Ra2 | ICOS | DAP10 | CD3ζ |
| IL13Ra2 | ICOS | DAP10 | CD3δ |
| IL13Ra2 | ICOS | DAP10 | CD3γ |
| IL13Ra2 | ICOS | DAP10 | CD3ε |
| IL13Ra2 | ICOS | DAP10 | FcγRI-γ |
| IL13Ra2 | ICOS | DAP10 | FcγRIII-γ |
| IL13Ra2 | ICOS | DAP10 | FcεRIβ |
| IL13Ra2 | ICOS | DAP10 | FcεRIγ |
| IL13Ra2 | ICOS | DAP10 | DAP10 |
| IL13Ra2 | ICOS | DAP10 | DAP12 |
| IL13Ra2 | ICOS | DAP10 | CD32 |
| IL13Ra2 | ICOS | DAP10 | CD79a |
| IL13Ra2 | ICOS | DAP10 | CD79b |
| IL13Ra2 | ICOS | DAP12 | CD8 |
| IL13Ra2 | ICOS | DAP12 | CD3ζ |
| IL13Ra2 | ICOS | DAP12 | CD3δ |
| IL13Ra2 | ICOS | DAP12 | CD3γ |
| IL13Ra2 | ICOS | DAP12 | CD3ε |
| IL13Ra2 | ICOS | DAP12 | FcγRI-γ |
| IL13Ra2 | ICOS | DAP12 | FcγRIII-γ |
| IL13Ra2 | ICOS | DAP12 | FcεRIβ |
| IL13Ra2 | ICOS | DAP12 | FcεRIγ |
| IL13Ra2 | ICOS | DAP12 | DAP10 |
| IL13Ra2 | ICOS | DAP12 | DAP12 |
| IL13Ra2 | ICOS | DAP12 | CD32 |
| IL13Ra2 | ICOS | DAP12 | CD79a |
| IL13Ra2 | ICOS | DAP12 | CD79b |
| IL13Ra2 | ICOS | MyD88 | CD8 |
| IL13Ra2 | ICOS | MyD88 | CD3ζ |
| IL13Ra2 | ICOS | MyD88 | CD3δ |
| IL13Ra2 | ICOS | MyD88 | CD3γ |
| IL13Ra2 | ICOS | MyD88 | CD3ε |
| IL13Ra2 | ICOS | MyD88 | FcγRI-γ |
| IL13Ra2 | ICOS | MyD88 | FcγRIII-γ |
| IL13Ra2 | ICOS | MyD88 | FcεRIβ |
| IL13Ra2 | ICOS | MyD88 | FcεRIγ |
| IL13Ra2 | ICOS | MyD88 | DAP10 |
| IL13Ra2 | ICOS | MyD88 | DAP12 |
| IL13Ra2 | ICOS | MyD88 | CD32 |
| IL13Ra2 | ICOS | MyD88 | CD79a |
| IL13Ra2 | ICOS | MyD88 | CD79b |
| IL13Ra2 | ICOS | CD7 | CD8 |
| IL13Ra2 | ICOS | CD7 | CD3ζ |
| IL13Ra2 | ICOS | CD7 | CD3δ |
| IL13Ra2 | ICOS | CD7 | CD3γ |
| IL13Ra2 | ICOS | CD7 | CD3ε |
| IL13Ra2 | ICOS | CD7 | FcγRI-γ |
| IL13Ra2 | ICOS | CD7 | FcγRIII-γ |
| IL13Ra2 | ICOS | CD7 | FcεRIβ |
| IL13Ra2 | ICOS | CD7 | FcεRIγ |
| IL13Ra2 | ICOS | CD7 | DAP10 |
| IL13Ra2 | ICOS | CD7 | DAP12 |
| IL13Ra2 | ICOS | CD7 | CD32 |
| IL13Ra2 | ICOS | CD7 | CD79a |
| IL13Ra2 | ICOS | CD7 | CD79b |
| IL13Ra2 | ICOS | BTNL3 | CD8 |
| IL13Ra2 | ICOS | BTNL3 | CD3ζ |
| IL13Ra2 | ICOS | BTNL3 | CD3δ |
| IL13Ra2 | ICOS | BTNL3 | CD3γ |
| IL13Ra2 | ICOS | BTNL3 | CD3ε |
| IL13Ra2 | ICOS | BTNL3 | FcγRI-γ |
| IL13Ra2 | ICOS | BTNL3 | FcγRIII-γ |

TABLE 3-continued

Third Generation CARs

| ScFv | Co-stimulatory Signal | Co-stimulatory Signal | Signal Domain |
|---|---|---|---|
| IL13Ra2 | ICOS | BTNL3 | FcεRIβ |
| IL13Ra2 | ICOS | BTNL3 | FcεRIγ |
| IL13Ra2 | ICOS | BTNL3 | DAP10 |
| IL13Ra2 | ICOS | BTNL3 | DAP12 |
| IL13Ra2 | ICOS | BTNL3 | CD32 |
| IL13Ra2 | ICOS | BTNL3 | CD79a |
| IL13Ra2 | ICOS | BTNL3 | CD79b |
| IL13Ra2 | ICOS | NKG2D | CD8 |
| IL13Ra2 | ICOS | NKG2D | CD3ζ |
| IL13Ra2 | ICOS | NKG2D | CD3δ |
| IL13Ra2 | ICOS | NKG2D | CD3γ |
| IL13Ra2 | ICOS | NKG2D | CD3ε |
| IL13Ra2 | ICOS | NKG2D | FcγRI-γ |
| IL13Ra2 | ICOS | NKG2D | FcγRIII-γ |
| IL13Ra2 | ICOS | NKG2D | FcεRIβ |
| IL13Ra2 | ICOS | NKG2D | FcεRIγ |
| IL13Ra2 | ICOS | NKG2D | DAP10 |
| IL13Ra2 | ICOS | NKG2D | DAP12 |
| IL13Ra2 | ICOS | NKG2D | CD32 |
| IL13Ra2 | ICOS | NKG2D | CD79a |
| IL13Ra2 | ICOS | NKG2D | CD79b |
| IL13Ra2 | CD27 | CD28 | CD8 |
| IL13Ra2 | CD27 | CD28 | CD3ζ |
| IL13Ra2 | CD27 | CD28 | CD3δ |
| IL13Ra2 | CD27 | CD28 | CD3γ |
| IL13Ra2 | CD27 | CD28 | CD3ε |
| IL13Ra2 | CD27 | CD28 | FcγRI-γ |
| IL13Ra2 | CD27 | CD28 | FcγRIII-γ |
| IL13Ra2 | CD27 | CD28 | FcεRIβ |
| IL13Ra2 | CD27 | CD28 | FcεRIγ |
| IL13Ra2 | CD27 | CD28 | DAP10 |
| IL13Ra2 | CD27 | CD28 | DAP12 |
| IL13Ra2 | CD27 | CD28 | CD32 |
| IL13Ra2 | CD27 | CD28 | CD79a |
| IL13Ra2 | CD27 | CD28 | CD79b |
| IL13Ra2 | CD27 | CD8 | CD8 |
| IL13Ra2 | CD27 | CD8 | CD3ζ |
| IL13Ra2 | CD27 | CD8 | CD3δ |
| IL13Ra2 | CD27 | CD8 | CD3γ |
| IL13Ra2 | CD27 | CD8 | CD3ε |
| IL13Ra2 | CD27 | CD8 | FcγRI-γ |
| IL13Ra2 | CD27 | CD8 | FcγRIII-γ |
| IL13Ra2 | CD27 | CD8 | FcεRIβ |
| IL13Ra2 | CD27 | CD8 | FcεRIγ |
| IL13Ra2 | CD27 | CD8 | DAP10 |
| IL13Ra2 | CD27 | CD8 | DAP12 |
| IL13Ra2 | CD27 | CD8 | CD32 |
| IL13Ra2 | CD27 | CD8 | CD79a |
| IL13Ra2 | CD27 | CD8 | CD79b |
| IL13Ra2 | CD27 | CD4 | CD8 |
| IL13Ra2 | CD27 | CD4 | CD3ζ |
| IL13Ra2 | CD27 | CD4 | CD3δ |
| IL13Ra2 | CD27 | CD4 | CD3γ |
| IL13Ra2 | CD27 | CD4 | CD3ε |
| IL13Ra2 | CD27 | CD4 | FcγRI-γ |
| IL13Ra2 | CD27 | CD4 | FcγRIII-γ |
| IL13Ra2 | CD27 | CD4 | FcεRIβ |
| IL13Ra2 | CD27 | CD4 | FcεRIγ |
| IL13Ra2 | CD27 | CD4 | DAP10 |
| IL13Ra2 | CD27 | CD4 | DAP12 |
| IL13Ra2 | CD27 | CD4 | CD32 |
| IL13Ra2 | CD27 | CD4 | CD79a |
| IL13Ra2 | CD27 | CD4 | CD79b |
| IL13Ra2 | CD27 | b2c | CD8 |
| IL13Ra2 | CD27 | b2c | CD3ζ |
| IL13Ra2 | CD27 | b2c | CD3δ |
| IL13Ra2 | CD27 | b2c | CD3γ |
| IL13Ra2 | CD27 | b2c | CD3ε |
| IL13Ra2 | CD27 | b2c | FcγRI-γ |
| IL13Ra2 | CD27 | b2c | FcγRIII-γ |
| IL13Ra2 | CD27 | b2c | FcεRIβ |
| IL13Ra2 | CD27 | b2c | FcεRIγ |
| IL13Ra2 | CD27 | b2c | DAP10 |
| IL13Ra2 | CD27 | b2c | DAP12 |
| IL13Ra2 | CD27 | b2c | CD32 |
| IL13Ra2 | CD27 | b2c | CD79a |
| IL13Ra2 | CD27 | b2c | CD79b |
| IL13Ra2 | CD27 | CD137/41BB | CD8 |
| IL13Ra2 | CD27 | CD137/41BB | CD3ζ |
| IL13Ra2 | CD27 | CD137/41BB | CD3δ |
| IL13Ra2 | CD27 | CD137/41BB | CD3γ |
| IL13Ra2 | CD27 | CD137/41BB | CD3ε |
| IL13Ra2 | CD27 | CD137/41BB | FcγRI-γ |
| IL13Ra2 | CD27 | CD137/41BB | FcγRIII-γ |
| IL13Ra2 | CD27 | CD137/41BB | FcεRIβ |
| IL13Ra2 | CD27 | CD137/41BB | FcεRIγ |
| IL13Ra2 | CD27 | CD137/41BB | DAP10 |
| IL13Ra2 | CD27 | CD137/41BB | DAP12 |
| IL13Ra2 | CD27 | CD137/41BB | CD32 |
| IL13Ra2 | CD27 | CD137/41BB | CD79a |
| IL13Ra2 | CD27 | CD137/41BB | CD79b |
| IL13Ra2 | CD27 | ICOS | CD8 |
| IL13Ra2 | CD27 | ICOS | CD3ζ |
| IL13Ra2 | CD27 | ICOS | CD3δ |
| IL13Ra2 | CD27 | ICOS | CD3γ |
| IL13Ra2 | CD27 | ICOS | CD3ε |
| IL13Ra2 | CD27 | ICOS | FcγRI-γ |
| IL13Ra2 | CD27 | ICOS | FcγRIII-γ |
| IL13Ra2 | CD27 | ICOS | FcεRIβ |
| IL13Ra2 | CD27 | ICOS | FcεRIγ |
| IL13Ra2 | CD27 | ICOS | DAP10 |
| IL13Ra2 | CD27 | ICOS | DAP12 |
| IL13Ra2 | CD27 | ICOS | CD32 |
| IL13Ra2 | CD27 | ICOS | CD79a |
| IL13Ra2 | CD27 | ICOS | CD79b |
| IL13Ra2 | CD27 | CD27 | CD8 |
| IL13Ra2 | CD27 | CD27 | CD3ζ |
| IL13Ra2 | CD27 | CD27 | CD3δ |
| IL13Ra2 | CD27 | CD27 | CD3γ |
| IL13Ra2 | CD27 | CD27 | CD3ε |
| IL13Ra2 | CD27 | CD27 | FcγRI-γ |
| IL13Ra2 | CD27 | CD27 | FcγRIII-γ |
| IL13Ra2 | CD27 | CD27 | FcεRIβ |
| IL13Ra2 | CD27 | CD27 | FcεRIγ |
| IL13Ra2 | CD27 | CD27 | DAP10 |
| IL13Ra2 | CD27 | CD27 | DAP12 |
| IL13Ra2 | CD27 | CD27 | CD32 |
| IL13Ra2 | CD27 | CD27 | CD79a |
| IL13Ra2 | CD27 | CD27 | CD79b |
| IL13Ra2 | CD27 | CD28δ | CD8 |
| IL13Ra2 | CD27 | CD28δ | CD3ζ |
| IL13Ra2 | CD27 | CD28δ | CD3δ |
| IL13Ra2 | CD27 | CD28δ | CD3γ |
| IL13Ra2 | CD27 | CD28δ | CD3ε |
| IL13Ra2 | CD27 | CD28δ | FcγRI-γ |
| IL13Ra2 | CD27 | CD28δ | FcγRIII-γ |
| IL13Ra2 | CD27 | CD28δ | FcεRIβ |
| IL13Ra2 | CD27 | CD28δ | FcεRIγ |
| IL13Ra2 | CD27 | CD28δ | DAP10 |
| IL13Ra2 | CD27 | CD28δ | DAP12 |
| IL13Ra2 | CD27 | CD28δ | CD32 |
| IL13Ra2 | CD27 | CD28δ | CD79a |
| IL13Ra2 | CD27 | CD28δ | CD79b |
| IL13Ra2 | CD27 | CD80 | CD8 |
| IL13Ra2 | CD27 | CD80 | CD3ζ |
| IL13Ra2 | CD27 | CD80 | CD3δ |
| IL13Ra2 | CD27 | CD80 | CD3γ |
| IL13Ra2 | CD27 | CD80 | CD3ε |
| IL13Ra2 | CD27 | CD80 | FcγRI-γ |
| IL13Ra2 | CD27 | CD80 | FcγRIII-γ |
| IL13Ra2 | CD27 | CD80 | FcεRIβ |
| IL13Ra2 | CD27 | CD80 | FcεRIγ |
| IL13Ra2 | CD27 | CD80 | DAP10 |
| IL13Ra2 | CD27 | CD80 | DAP12 |
| IL13Ra2 | CD27 | CD80 | CD32 |
| IL13Ra2 | CD27 | CD80 | CD79a |
| IL13Ra2 | CD27 | CD80 | CD79b |
| IL13Ra2 | CD27 | CD86 | CD8 |
| IL13Ra2 | CD27 | CD86 | CD3ζ |
| IL13Ra2 | CD27 | CD86 | CD3δ |

TABLE 3-continued

Third Generation CARs

| ScFv | Co-stimulatory Signal | Co-stimulatory Signal | Signal Domain |
|---|---|---|---|
| IL13Ra2 | CD27 | CD86 | CD3γ |
| IL13Ra2 | CD27 | CD86 | CD3ε |
| IL13Ra2 | CD27 | CD86 | FcγRI-γ |
| IL13Ra2 | CD27 | CD86 | FcγRIII-γ |
| IL13Ra2 | CD27 | CD86 | FcεRIβ |
| IL13Ra2 | CD27 | CD86 | FcεRIγ |
| IL13Ra2 | CD27 | CD86 | DAP10 |
| IL13Ra2 | CD27 | CD86 | DAP12 |
| IL13Ra2 | CD27 | CD86 | CD32 |
| IL13Ra2 | CD27 | CD86 | CD79a |
| IL13Ra2 | CD27 | CD86 | CD79b |
| IL13Ra2 | CD27 | OX40 | CD8 |
| IL13Ra2 | CD27 | OX40 | CD3ζ |
| IL13Ra2 | CD27 | OX40 | CD3δ |
| IL13Ra2 | CD27 | OX40 | CD3γ |
| IL13Ra2 | CD27 | OX40 | CD3ε |
| IL13Ra2 | CD27 | OX40 | FcγRI-γ |
| IL13Ra2 | CD27 | OX40 | FcγRIII-γ |
| IL13Ra2 | CD27 | OX40 | FcεRIβ |
| IL13Ra2 | CD27 | OX40 | FcεRIγ |
| IL13Ra2 | CD27 | OX40 | DAP10 |
| IL13Ra2 | CD27 | OX40 | DAP12 |
| IL13Ra2 | CD27 | OX40 | CD32 |
| IL13Ra2 | CD27 | OX40 | CD79a |
| IL13Ra2 | CD27 | OX40 | CD79b |
| IL13Ra2 | CD27 | DAP10 | CD8 |
| IL13Ra2 | CD27 | DAP10 | CD3ζ |
| IL13Ra2 | CD27 | DAP10 | CD3δ |
| IL13Ra2 | CD27 | DAP10 | CD3γ |
| IL13Ra2 | CD27 | DAP10 | CD3ε |
| IL13Ra2 | CD27 | DAP10 | FcγRI-γ |
| IL13Ra2 | CD27 | DAP10 | FcγRIII-γ |
| IL13Ra2 | CD27 | DAP10 | FcεRIβ |
| IL13Ra2 | CD27 | DAP10 | FcεRIγ |
| IL13Ra2 | CD27 | DAP10 | DAP10 |
| IL13Ra2 | CD27 | DAP10 | DAP12 |
| IL13Ra2 | CD27 | DAP10 | CD32 |
| IL13Ra2 | CD27 | DAP10 | CD79a |
| IL13Ra2 | CD27 | DAP10 | CD79b |
| IL13Ra2 | CD27 | DAP12 | CD8 |
| IL13Ra2 | CD27 | DAP12 | CD3ζ |
| IL13Ra2 | CD27 | DAP12 | CD3δ |
| IL13Ra2 | CD27 | DAP12 | CD3γ |
| IL13Ra2 | CD27 | DAP12 | CD3ε |
| IL13Ra2 | CD27 | DAP12 | FcγRI-γ |
| IL13Ra2 | CD27 | DAP12 | FcγRIII-γ |
| IL13Ra2 | CD27 | DAP12 | FcεRIβ |
| IL13Ra2 | CD27 | DAP12 | FcεRIγ |
| IL13Ra2 | CD27 | DAP12 | DAP10 |
| IL13Ra2 | CD27 | DAP12 | DAP12 |
| IL13Ra2 | CD27 | DAP12 | CD32 |
| IL13Ra2 | CD27 | DAP12 | CD79a |
| IL13Ra2 | CD27 | DAP12 | CD79b |
| IL13Ra2 | CD27 | MyD88 | CD8 |
| IL13Ra2 | CD27 | MyD88 | CD3ζ |
| IL13Ra2 | CD27 | MyD88 | CD3δ |
| IL13Ra2 | CD27 | MyD88 | CD3γ |
| IL13Ra2 | CD27 | MyD88 | CD3ε |
| IL13Ra2 | CD27 | MyD88 | FcγRI-γ |
| IL13Ra2 | CD27 | MyD88 | FcγRIII-γ |
| IL13Ra2 | CD27 | MyD88 | FcεRIβ |
| IL13Ra2 | CD27 | MyD88 | FcεRIγ |
| IL13Ra2 | CD27 | MyD88 | DAP10 |
| IL13Ra2 | CD27 | MyD88 | DAP12 |
| IL13Ra2 | CD27 | MyD88 | CD32 |
| IL13Ra2 | CD27 | MyD88 | CD79a |
| IL13Ra2 | CD27 | MyD88 | CD79b |
| IL13Ra2 | CD27 | CD7 | CD8 |
| IL13Ra2 | CD27 | CD7 | CD3ζ |
| IL13Ra2 | CD27 | CD7 | CD3δ |
| IL13Ra2 | CD27 | CD7 | CD3γ |
| IL13Ra2 | CD27 | CD7 | CD3ε |
| IL13Ra2 | CD27 | CD7 | FcγRI-γ |
| IL13Ra2 | CD27 | CD7 | FcγRIII-γ |
| IL13Ra2 | CD27 | CD7 | FcεRIβ |
| IL13Ra2 | CD27 | CD7 | FcεRIγ |
| IL13Ra2 | CD27 | CD7 | DAP10 |
| IL13Ra2 | CD27 | CD7 | DAP12 |
| IL13Ra2 | CD27 | CD7 | CD32 |
| IL13Ra2 | CD27 | CD7 | CD79a |
| IL13Ra2 | CD27 | CD7 | CD79b |
| IL13Ra2 | CD27 | BTNL3 | CD8 |
| IL13Ra2 | CD27 | BTNL3 | CD3ζ |
| IL13Ra2 | CD27 | BTNL3 | CD3δ |
| IL13Ra2 | CD27 | BTNL3 | CD3γ |
| IL13Ra2 | CD27 | BTNL3 | CD3ε |
| IL13Ra2 | CD27 | BTNL3 | FcγRI-γ |
| IL13Ra2 | CD27 | BTNL3 | FcγRIII-γ |
| IL13Ra2 | CD27 | BTNL3 | FcεRIβ |
| IL13Ra2 | CD27 | BTNL3 | FcεRIγ |
| IL13Ra2 | CD27 | BTNL3 | DAP10 |
| IL13Ra2 | CD27 | BTNL3 | DAP12 |
| IL13Ra2 | CD27 | BTNL3 | CD32 |
| IL13Ra2 | CD27 | BTNL3 | CD79a |
| IL13Ra2 | CD27 | BTNL3 | CD79b |
| IL13Ra2 | CD27 | NKG2D | CD8 |
| IL13Ra2 | CD27 | NKG2D | CD3ζ |
| IL13Ra2 | CD27 | NKG2D | CD3δ |
| IL13Ra2 | CD27 | NKG2D | CD3γ |
| IL13Ra2 | CD27 | NKG2D | CD3ε |
| IL13Ra2 | CD27 | NKG2D | FcγRI-γ |
| IL13Ra2 | CD27 | NKG2D | FcγRIII-γ |
| IL13Ra2 | CD27 | NKG2D | FcεRIβ |
| IL13Ra2 | CD27 | NKG2D | FcεRIγ |
| IL13Ra2 | CD27 | NKG2D | DAP10 |
| IL13Ra2 | CD27 | NKG2D | DAP12 |
| IL13Ra2 | CD27 | NKG2D | CD32 |
| IL13Ra2 | CD27 | NKG2D | CD79a |
| IL13Ra2 | CD27 | NKG2D | CD79b |
| IL13Ra2 | CD28δ | CD28 | CD8 |
| IL13Ra2 | CD28δ | CD28 | CD3ζ |
| IL13Ra2 | CD28δ | CD28 | CD3δ |
| IL13Ra2 | CD28δ | CD28 | CD3γ |
| IL13Ra2 | CD28δ | CD28 | CD3ε |
| IL13Ra2 | CD28δ | CD28 | FcγRI-γ |
| IL13Ra2 | CD28δ | CD28 | FcγRIII-γ |
| IL13Ra2 | CD28δ | CD28 | FcεRIβ |
| IL13Ra2 | CD28δ | CD28 | FcεRIγ |
| IL13Ra2 | CD28δ | CD28 | DAP10 |
| IL13Ra2 | CD28δ | CD28 | DAP12 |
| IL13Ra2 | CD28δ | CD28 | CD32 |
| IL13Ra2 | CD28δ | CD28 | CD79a |
| IL13Ra2 | CD28δ | CD28 | CD79b |
| IL13Ra2 | CD28δ | CD8 | CD8 |
| IL13Ra2 | CD28δ | CD8 | CD3ζ |
| IL13Ra2 | CD28δ | CD8 | CD3δ |
| IL13Ra2 | CD28δ | CD8 | CD3γ |
| IL13Ra2 | CD28δ | CD8 | CD3ε |
| IL13Ra2 | CD28δ | CD8 | FcγRI-γ |
| IL13Ra2 | CD28δ | CD8 | FcγRIII-γ |
| IL13Ra2 | CD28δ | CD8 | FcεRIβ |
| IL13Ra2 | CD28δ | CD8 | FcεRIγ |
| IL13Ra2 | CD28δ | CD8 | DAP10 |
| IL13Ra2 | CD28δ | CD8 | DAP12 |
| IL13Ra2 | CD28δ | CD8 | CD32 |
| IL13Ra2 | CD28δ | CD8 | CD79a |
| IL13Ra2 | CD28δ | CD8 | CD79b |
| IL13Ra2 | CD28δ | CD4 | CD8 |
| IL13Ra2 | CD28δ | CD4 | CD3ζ |
| IL13Ra2 | CD28δ | CD4 | CD3δ |
| IL13Ra2 | CD28δ | CD4 | CD3γ |
| IL13Ra2 | CD28δ | CD4 | CD3ε |
| IL13Ra2 | CD28δ | CD4 | FcγRI-γ |
| IL13Ra2 | CD28δ | CD4 | FcγRIII-γ |
| IL13Ra2 | CD28δ | CD4 | FcεRIβ |
| IL13Ra2 | CD28δ | CD4 | FcεRIγ |
| IL13Ra2 | CD28δ | CD4 | DAP10 |
| IL13Ra2 | CD28δ | CD4 | DAP12 |
| IL13Ra2 | CD28δ | CD4 | CD32 |
| IL13Ra2 | CD28δ | CD4 | CD79a |

TABLE 3-continued

Third Generation CARs

| ScFv | Co-stimulatory Signal | Co-stimulatory Signal | Signal Domain |
|---|---|---|---|
| IL13Ra2 | CD28δ | CD4 | CD79b |
| IL13Ra2 | CD28δ | b2c | CD8 |
| IL13Ra2 | CD28δ | b2c | CD3ζ |
| IL13Ra2 | CD28δ | b2c | CD3δ |
| IL13Ra2 | CD28δ | b2c | CD3γ |
| IL13Ra2 | CD28δ | b2c | CD3ε |
| IL13Ra2 | CD28δ | b2c | FcγRI-γ |
| IL13Ra2 | CD28δ | b2c | FcγRIII-γ |
| IL13Ra2 | CD28δ | b2c | FcεRIβ |
| IL13Ra2 | CD28δ | b2c | FcεRIγ |
| IL13Ra2 | CD28δ | b2c | DAP10 |
| IL13Ra2 | CD28δ | b2c | DAP12 |
| IL13Ra2 | CD28δ | b2c | CD32 |
| IL13Ra2 | CD28δ | b2c | CD79a |
| IL13Ra2 | CD28δ | b2c | CD79b |
| IL13Ra2 | CD28δ | CD137/41BB | CD8 |
| IL13Ra2 | CD28δ | CD137/41BB | CD3ζ |
| IL13Ra2 | CD28δ | CD137/41BB | CD3δ |
| IL13Ra2 | CD28δ | CD137/41BB | CD3γ |
| IL13Ra2 | CD28δ | CD137/41BB | CD3ε |
| IL13Ra2 | CD28δ | CD137/41BB | FcγRI-γ |
| IL13Ra2 | CD28δ | CD137/41BB | FcγRIII-γ |
| IL13Ra2 | CD28δ | CD137/41BB | FcεRIβ |
| IL13Ra2 | CD28δ | CD137/41BB | FcεRIγ |
| IL13Ra2 | CD28δ | CD137/41BB | DAP10 |
| IL13Ra2 | CD28δ | CD137/41BB | DAP12 |
| IL13Ra2 | CD28δ | CD137/41BB | CD32 |
| IL13Ra2 | CD28δ | CD137/41BB | CD79a |
| IL13Ra2 | CD28δ | CD137/41BB | CD79b |
| IL13Ra2 | CD28δ | ICOS | CD8 |
| IL13Ra2 | CD28δ | ICOS | CD3ζ |
| IL13Ra2 | CD28δ | ICOS | CD3δ |
| IL13Ra2 | CD28δ | ICOS | CD3γ |
| IL13Ra2 | CD28δ | ICOS | CD3ε |
| IL13Ra2 | CD28δ | ICOS | FcγRI-γ |
| IL13Ra2 | CD28δ | ICOS | FcγRIII-γ |
| IL13Ra2 | CD28δ | ICOS | FcεRIβ |
| IL13Ra2 | CD28δ | ICOS | FcεRIγ |
| IL13Ra2 | CD28δ | ICOS | DAP10 |
| IL13Ra2 | CD28δ | ICOS | DAP12 |
| IL13Ra2 | CD28δ | ICOS | CD32 |
| IL13Ra2 | CD28δ | ICOS | CD79a |
| IL13Ra2 | CD28δ | ICOS | CD79b |
| IL13Ra2 | CD28δ | CD27 | CD8 |
| IL13Ra2 | CD28δ | CD27 | CD3ζ |
| IL13Ra2 | CD28δ | CD27 | CD3δ |
| IL13Ra2 | CD28δ | CD27 | CD3γ |
| IL13Ra2 | CD28δ | CD27 | CD3ε |
| IL13Ra2 | CD28δ | CD27 | FcγRI-γ |
| IL13Ra2 | CD28δ | CD27 | FcγRIII-γ |
| IL13Ra2 | CD28δ | CD27 | FcεRIβ |
| IL13Ra2 | CD28δ | CD27 | FcεRIγ |
| IL13Ra2 | CD28δ | CD27 | DAP10 |
| IL13Ra2 | CD28δ | CD27 | DAP12 |
| IL13Ra2 | CD28δ | CD27 | CD32 |
| IL13Ra2 | CD28δ | CD27 | CD79a |
| IL13Ra2 | CD28δ | CD27 | CD79b |
| IL13Ra2 | CD28δ | CD28δ | CD8 |
| IL13Ra2 | CD28δ | CD28δ | CD3ζ |
| IL13Ra2 | CD28δ | CD28δ | CD3δ |
| IL13Ra2 | CD28δ | CD28δ | CD3γ |
| IL13Ra2 | CD28δ | CD28δ | CD3ε |
| IL13Ra2 | CD28δ | CD28δ | FcγRI-γ |
| IL13Ra2 | CD28δ | CD28δ | FcγRIII-γ |
| IL13Ra2 | CD28δ | CD28δ | FcεRIβ |
| IL13Ra2 | CD28δ | CD28δ | FcεRIγ |
| IL13Ra2 | CD28δ | CD28δ | DAP10 |
| IL13Ra2 | CD28δ | CD28δ | DAP12 |
| IL13Ra2 | CD28δ | CD28δ | CD32 |
| IL13Ra2 | CD28δ | CD28δ | CD79a |
| IL13Ra2 | CD28δ | CD28δ | CD79b |
| IL13Ra2 | CD28δ | CD80 | CD8 |
| IL13Ra2 | CD28δ | CD80 | CD3ζ |
| IL13Ra2 | CD28δ | CD80 | CD3δ |
| IL13Ra2 | CD28δ | CD80 | CD3γ |
| IL13Ra2 | CD28δ | CD80 | CD3ε |
| IL13Ra2 | CD28δ | CD80 | FcγRI-γ |
| IL13Ra2 | CD28δ | CD80 | FcγRIII-γ |
| IL13Ra2 | CD28δ | CD80 | FcεRIβ |
| IL13Ra2 | CD28δ | CD80 | FcεRIγ |
| IL13Ra2 | CD28δ | CD80 | DAP10 |
| IL13Ra2 | CD28δ | CD80 | DAP12 |
| IL13Ra2 | CD28δ | CD80 | CD32 |
| IL13Ra2 | CD28δ | CD80 | CD79a |
| IL13Ra2 | CD28δ | CD80 | CD79b |
| IL13Ra2 | CD28δ | CD86 | CD8 |
| IL13Ra2 | CD28δ | CD86 | CD3ζ |
| IL13Ra2 | CD28δ | CD86 | CD3δ |
| IL13Ra2 | CD28δ | CD86 | CD3γ |
| IL13Ra2 | CD28δ | CD86 | CD3ε |
| IL13Ra2 | CD28δ | CD86 | FcγRI-γ |
| IL13Ra2 | CD28δ | CD86 | FcγRIII-γ |
| IL13Ra2 | CD28δ | CD86 | FcεRIβ |
| IL13Ra2 | CD28δ | CD86 | FcεRIγ |
| IL13Ra2 | CD28δ | CD86 | DAP10 |
| IL13Ra2 | CD28δ | CD86 | DAP12 |
| IL13Ra2 | CD28δ | CD86 | CD32 |
| IL13Ra2 | CD28δ | CD86 | CD79a |
| IL13Ra2 | CD28δ | CD86 | CD79b |
| IL13Ra2 | CD28δ | OX40 | CD8 |
| IL13Ra2 | CD28δ | OX40 | CD3ζ |
| IL13Ra2 | CD28δ | OX40 | CD3δ |
| IL13Ra2 | CD28δ | OX40 | CD3γ |
| IL13Ra2 | CD28δ | OX40 | CD3ε |
| IL13Ra2 | CD28δ | OX40 | FcγRI-γ |
| IL13Ra2 | CD28δ | OX40 | FcγRIII-γ |
| IL13Ra2 | CD28δ | OX40 | FcεRIβ |
| IL13Ra2 | CD28δ | OX40 | FcεRIγ |
| IL13Ra2 | CD28δ | OX40 | DAP10 |
| IL13Ra2 | CD28δ | OX40 | DAP12 |
| IL13Ra2 | CD28δ | OX40 | CD32 |
| IL13Ra2 | CD28δ | OX40 | CD79a |
| IL13Ra2 | CD28δ | OX40 | CD79b |
| IL13Ra2 | CD28δ | DAP10 | CD8 |
| IL13Ra2 | CD28δ | DAP10 | CD3ζ |
| IL13Ra2 | CD28δ | DAP10 | CD3δ |
| IL13Ra2 | CD28δ | DAP10 | CD3γ |
| IL13Ra2 | CD28δ | DAP10 | CD3ε |
| IL13Ra2 | CD28δ | DAP10 | FcγRI-γ |
| IL13Ra2 | CD28δ | DAP10 | FcγRIII-γ |
| IL13Ra2 | CD28δ | DAP10 | FcεRIβ |
| IL13Ra2 | CD28δ | DAP10 | FcεRIγ |
| IL13Ra2 | CD28δ | DAP10 | DAP10 |
| IL13Ra2 | CD28δ | DAP10 | DAP12 |
| IL13Ra2 | CD28δ | DAP10 | CD32 |
| IL13Ra2 | CD28δ | DAP10 | CD79a |
| IL13Ra2 | CD28δ | DAP10 | CD79b |
| IL13Ra2 | CD28δ | DAP12 | CD8 |
| IL13Ra2 | CD28δ | DAP12 | CD3ζ |
| IL13Ra2 | CD28δ | DAP12 | CD3δ |
| IL13Ra2 | CD28δ | DAP12 | CD3γ |
| IL13Ra2 | CD28δ | DAP12 | CD3ε |
| IL13Ra2 | CD28δ | DAP12 | FcγRI-γ |
| IL13Ra2 | CD28δ | DAP12 | FcγRIII-γ |
| IL13Ra2 | CD28δ | DAP12 | FcεRIβ |
| IL13Ra2 | CD28δ | DAP12 | FcεRIγ |
| IL13Ra2 | CD28δ | DAP12 | DAP10 |
| IL13Ra2 | CD28δ | DAP12 | DAP12 |
| IL13Ra2 | CD28δ | DAP12 | CD32 |
| IL13Ra2 | CD28δ | DAP12 | CD79a |
| IL13Ra2 | CD28δ | DAP12 | CD79b |
| IL13Ra2 | CD28δ | MyD88 | CD8 |
| IL13Ra2 | CD28δ | MyD88 | CD3ζ |
| IL13Ra2 | CD28δ | MyD88 | CD3δ |
| IL13Ra2 | CD28δ | MyD88 | CD3γ |
| IL13Ra2 | CD28δ | MyD88 | CD3ε |
| IL13Ra2 | CD28δ | MyD88 | FcγRI-γ |
| IL13Ra2 | CD28δ | MyD88 | FcγRIII-γ |
| IL13Ra2 | CD28δ | MyD88 | FcεRIβ |
| IL13Ra2 | CD28δ | MyD88 | FcεRIγ |

TABLE 3-continued

Third Generation CARs

| ScFv | Co-stimulatory Signal | Co-stimulatory Signal | Signal Domain |
|---|---|---|---|
| IL13Ra2 | CD28δ | MyD88 | DAP10 |
| IL13Ra2 | CD28δ | MyD88 | DAP12 |
| IL13Ra2 | CD28δ | MyD88 | CD32 |
| IL13Ra2 | CD28δ | MyD88 | CD79a |
| IL13Ra2 | CD28δ | MyD88 | CD79b |
| IL13Ra2 | CD28δ | CD7 | CD8 |
| IL13Ra2 | CD28δ | CD7 | CD3ζ |
| IL13Ra2 | CD28δ | CD7 | CD3δ |
| IL13Ra2 | CD28δ | CD7 | CD3γ |
| IL13Ra2 | CD28δ | CD7 | CD3ε |
| IL13Ra2 | CD28δ | CD7 | FcγRI-γ |
| IL13Ra2 | CD28δ | CD7 | FcγRIII-γ |
| IL13Ra2 | CD28δ | CD7 | FcεRIβ |
| IL13Ra2 | CD28δ | CD7 | FcεRIγ |
| IL13Ra2 | CD28δ | CD7 | DAP10 |
| IL13Ra2 | CD28δ | CD7 | DAP12 |
| IL13Ra2 | CD28δ | CD7 | CD32 |
| IL13Ra2 | CD28δ | CD7 | CD79a |
| IL13Ra2 | CD28δ | CD7 | CD79b |
| IL13Ra2 | CD28δ | BTNL3 | CD8 |
| IL13Ra2 | CD28δ | BTNL3 | CD3ζ |
| IL13Ra2 | CD28δ | BTNL3 | CD3δ |
| IL13Ra2 | CD28δ | BTNL3 | CD3γ |
| IL13Ra2 | CD28δ | BTNL3 | CD3ε |
| IL13Ra2 | CD28δ | BTNL3 | FcγRI-γ |
| IL13Ra2 | CD28δ | BTNL3 | FcγRIII-γ |
| IL13Ra2 | CD28δ | BTNL3 | FcεRIβ |
| IL13Ra2 | CD28δ | BTNL3 | FcεRIγ |
| IL13Ra2 | CD28δ | BTNL3 | DAP10 |
| IL13Ra2 | CD28δ | BTNL3 | DAP12 |
| IL13Ra2 | CD28δ | BTNL3 | CD32 |
| IL13Ra2 | CD28δ | BTNL3 | CD79a |
| IL13Ra2 | CD28δ | BTNL3 | CD79b |
| IL13Ra2 | CD28δ | NKG2D | CD8 |
| IL13Ra2 | CD28δ | NKG2D | CD3ζ |
| IL13Ra2 | CD28δ | NKG2D | CD3δ |
| IL13Ra2 | CD28δ | NKG2D | CD3γ |
| IL13Ra2 | CD28δ | NKG2D | CD3ε |
| IL13Ra2 | CD28δ | NKG2D | FcγRI-γ |
| IL13Ra2 | CD28δ | NKG2D | FcγRIII-γ |
| IL13Ra2 | CD28δ | NKG2D | FcεRIβ |
| IL13Ra2 | CD28δ | NKG2D | FcεRIγ |
| IL13Ra2 | CD28δ | NKG2D | DAP10 |
| IL13Ra2 | CD28δ | NKG2D | DAP12 |
| IL13Ra2 | CD28δ | NKG2D | CD32 |
| IL13Ra2 | CD28δ | NKG2D | CD79a |
| IL13Ra2 | CD28δ | NKG2D | CD79b |
| IL13Ra2 | CD80 | CD28 | CD8 |
| IL13Ra2 | CD80 | CD28 | CD3ζ |
| IL13Ra2 | CD80 | CD28 | CD3δ |
| IL13Ra2 | CD80 | CD28 | CD3γ |
| IL13Ra2 | CD80 | CD28 | CD3ε |
| IL13Ra2 | CD80 | CD28 | FcγRI-γ |
| IL13Ra2 | CD80 | CD28 | FcγRIII-γ |
| IL13Ra2 | CD80 | CD28 | FcεRIβ |
| IL13Ra2 | CD80 | CD28 | FcεRIγ |
| IL13Ra2 | CD80 | CD28 | DAP10 |
| IL13Ra2 | CD80 | CD28 | DAP12 |
| IL13Ra2 | CD80 | CD28 | CD32 |
| IL13Ra2 | CD80 | CD28 | CD79a |
| IL13Ra2 | CD80 | CD28 | CD79b |
| IL13Ra2 | CD80 | CD8 | CD8 |
| IL13Ra2 | CD80 | CD8 | CD3ζ |
| IL13Ra2 | CD80 | CD8 | CD3δ |
| IL13Ra2 | CD80 | CD8 | CD3γ |
| IL13Ra2 | CD80 | CD8 | CD3ε |
| IL13Ra2 | CD80 | CD8 | FcγRI-γ |
| IL13Ra2 | CD80 | CD8 | FcγRIII-γ |
| IL13Ra2 | CD80 | CD8 | FcεRIβ |
| IL13Ra2 | CD80 | CD8 | FcεRIγ |
| IL13Ra2 | CD80 | CD8 | DAP10 |
| IL13Ra2 | CD80 | CD8 | DAP12 |
| IL13Ra2 | CD80 | CD8 | CD32 |
| IL13Ra2 | CD80 | CD8 | CD79a |
| IL13Ra2 | CD80 | CD8 | CD79b |
| IL13Ra2 | CD80 | CD4 | CD8 |
| IL13Ra2 | CD80 | CD4 | CD3ζ |
| IL13Ra2 | CD80 | CD4 | CD3δ |
| IL13Ra2 | CD80 | CD4 | CD3γ |
| IL13Ra2 | CD80 | CD4 | CD3ε |
| IL13Ra2 | CD80 | CD4 | FcγRI-γ |
| IL13Ra2 | CD80 | CD4 | FcγRIII-γ |
| IL13Ra2 | CD80 | CD4 | FcεRIβ |
| IL13Ra2 | CD80 | CD4 | FcεRIγ |
| IL13Ra2 | CD80 | CD4 | DAP10 |
| IL13Ra2 | CD80 | CD4 | DAP12 |
| IL13Ra2 | CD80 | CD4 | CD32 |
| IL13Ra2 | CD80 | CD4 | CD79a |
| IL13Ra2 | CD80 | CD4 | CD79b |
| IL13Ra2 | CD80 | b2c | CD8 |
| IL13Ra2 | CD80 | b2c | CD3ζ |
| IL13Ra2 | CD80 | b2c | CD3δ |
| IL13Ra2 | CD80 | b2c | CD3γ |
| IL13Ra2 | CD80 | b2c | CD3ε |
| IL13Ra2 | CD80 | b2c | FcγRI-γ |
| IL13Ra2 | CD80 | b2c | FcγRIII-γ |
| IL13Ra2 | CD80 | b2c | FcεRIβ |
| IL13Ra2 | CD80 | b2c | FcεRIγ |
| IL13Ra2 | CD80 | b2c | DAP10 |
| IL13Ra2 | CD80 | b2c | DAP12 |
| IL13Ra2 | CD80 | b2c | CD32 |
| IL13Ra2 | CD80 | b2c | CD79a |
| IL13Ra2 | CD80 | b2c | CD79b |
| IL13Ra2 | CD80 | CD137/41BB | CD8 |
| IL13Ra2 | CD80 | CD137/41BB | CD3ζ |
| IL13Ra2 | CD80 | CD137/41BB | CD3δ |
| IL13Ra2 | CD80 | CD137/41BB | CD3γ |
| IL13Ra2 | CD80 | CD137/41BB | CD3ε |
| IL13Ra2 | CD80 | CD137/41BB | FcγRI-γ |
| IL13Ra2 | CD80 | CD137/41BB | FcγRIII-γ |
| IL13Ra2 | CD80 | CD137/41BB | FcεRIβ |
| IL13Ra2 | CD80 | CD137/41BB | FcεRIγ |
| IL13Ra2 | CD80 | CD137/41BB | DAP10 |
| IL13Ra2 | CD80 | CD137/41BB | DAP12 |
| IL13Ra2 | CD80 | CD137/41BB | CD32 |
| IL13Ra2 | CD80 | CD137/41BB | CD79a |
| IL13Ra2 | CD80 | CD137/41BB | CD79b |
| IL13Ra2 | CD80 | ICOS | CD8 |
| IL13Ra2 | CD80 | ICOS | CD3ζ |
| IL13Ra2 | CD80 | ICOS | CD3δ |
| IL13Ra2 | CD80 | ICOS | CD3γ |
| IL13Ra2 | CD80 | ICOS | CD3ε |
| IL13Ra2 | CD80 | ICOS | FcγRI-γ |
| IL13Ra2 | CD80 | ICOS | FcγRIII-γ |
| IL13Ra2 | CD80 | ICOS | FcεRIβ |
| IL13Ra2 | CD80 | ICOS | FcεRIγ |
| IL13Ra2 | CD80 | ICOS | DAP10 |
| IL13Ra2 | CD80 | ICOS | DAP12 |
| IL13Ra2 | CD80 | ICOS | CD32 |
| IL13Ra2 | CD80 | ICOS | CD79a |
| IL13Ra2 | CD80 | ICOS | CD79b |
| IL13Ra2 | CD80 | CD27 | CD8 |
| IL13Ra2 | CD80 | CD27 | CD3ζ |
| IL13Ra2 | CD80 | CD27 | CD3δ |
| IL13Ra2 | CD80 | CD27 | CD3γ |
| IL13Ra2 | CD80 | CD27 | CD3ε |
| IL13Ra2 | CD80 | CD27 | FcγRI-γ |
| IL13Ra2 | CD80 | CD27 | FcγRIII-γ |
| IL13Ra2 | CD80 | CD27 | FcεRIβ |
| IL13Ra2 | CD80 | CD27 | FcεRIγ |
| IL13Ra2 | CD80 | CD27 | DAP10 |
| IL13Ra2 | CD80 | CD27 | DAP12 |
| IL13Ra2 | CD80 | CD27 | CD32 |
| IL13Ra2 | CD80 | CD27 | CD79a |
| IL13Ra2 | CD80 | CD27 | CD79b |
| IL13Ra2 | CD80 | CD28δ | CD8 |
| IL13Ra2 | CD80 | CD28δ | CD3ζ |
| IL13Ra2 | CD80 | CD28δ | CD3δ |
| IL13Ra2 | CD80 | CD28δ | CD3γ |
| IL13Ra2 | CD80 | CD28δ | CD3ε |

TABLE 3-continued

Third Generation CARs

| ScFv | Co-stimulatory Signal | Co-stimulatory Signal | Signal Domain |
|---|---|---|---|
| IL13Ra2 | CD80 | CD28δ | FcγRI-γ |
| IL13Ra2 | CD80 | CD28δ | FcγRIII-γ |
| IL13Ra2 | CD80 | CD28δ | FcεRIβ |
| IL13Ra2 | CD80 | CD28δ | FcεRIγ |
| IL13Ra2 | CD80 | CD28δ | DAP10 |
| IL13Ra2 | CD80 | CD28δ | DAP12 |
| IL13Ra2 | CD80 | CD28δ | CD32 |
| IL13Ra2 | CD80 | CD28δ | CD79a |
| IL13Ra2 | CD80 | CD28δ | CD79b |
| IL13Ra2 | CD80 | CD80 | CD8 |
| IL13Ra2 | CD80 | CD80 | CD3ζ |
| IL13Ra2 | CD80 | CD80 | CD3δ |
| IL13Ra2 | CD80 | CD80 | CD3γ |
| IL13Ra2 | CD80 | CD80 | CD3ε |
| IL13Ra2 | CD80 | CD80 | FcγRI-γ |
| IL13Ra2 | CD80 | CD80 | FcγRIII-γ |
| IL13Ra2 | CD80 | CD80 | FcεRIβ |
| IL13Ra2 | CD80 | CD80 | FcεRIγ |
| IL13Ra2 | CD80 | CD80 | DAP10 |
| IL13Ra2 | CD80 | CD80 | DAP12 |
| IL13Ra2 | CD80 | CD80 | CD32 |
| IL13Ra2 | CD80 | CD80 | CD79a |
| IL13Ra2 | CD80 | CD80 | CD79b |
| IL13Ra2 | CD80 | CD86 | CD8 |
| IL13Ra2 | CD80 | CD86 | CD3ζ |
| IL13Ra2 | CD80 | CD86 | CD3δ |
| IL13Ra2 | CD80 | CD86 | CD3γ |
| IL13Ra2 | CD80 | CD86 | CD3ε |
| IL13Ra2 | CD80 | CD86 | FcγRI-γ |
| IL13Ra2 | CD80 | CD86 | FcγRIII-γ |
| IL13Ra2 | CD80 | CD86 | FcεRIβ |
| IL13Ra2 | CD80 | CD86 | FcεRIγ |
| IL13Ra2 | CD80 | CD86 | DAP10 |
| IL13Ra2 | CD80 | CD86 | DAP12 |
| IL13Ra2 | CD80 | CD86 | CD32 |
| IL13Ra2 | CD80 | CD86 | CD79a |
| IL13Ra2 | CD80 | CD86 | CD79b |
| IL13Ra2 | CD80 | OX40 | CD8 |
| IL13Ra2 | CD80 | OX40 | CD3ζ |
| IL13Ra2 | CD80 | OX40 | CD3δ |
| IL13Ra2 | CD80 | OX40 | CD3γ |
| IL13Ra2 | CD80 | OX40 | CD3ε |
| IL13Ra2 | CD80 | OX40 | FcγRI-γ |
| IL13Ra2 | CD80 | OX40 | FcγRIII-γ |
| IL13Ra2 | CD80 | OX40 | FcεRIβ |
| IL13Ra2 | CD80 | OX40 | FcεRIγ |
| IL13Ra2 | CD80 | OX40 | DAP10 |
| IL13Ra2 | CD80 | OX40 | DAP12 |
| IL13Ra2 | CD80 | OX40 | CD32 |
| IL13Ra2 | CD80 | OX40 | CD79a |
| IL13Ra2 | CD80 | OX40 | CD79b |
| IL13Ra2 | CD80 | DAP10 | CD8 |
| IL13Ra2 | CD80 | DAP10 | CD3ζ |
| IL13Ra2 | CD80 | DAP10 | CD3δ |
| IL13Ra2 | CD80 | DAP10 | CD3γ |
| IL13Ra2 | CD80 | DAP10 | CD3ε |
| IL13Ra2 | CD80 | DAP10 | FcγRI-γ |
| IL13Ra2 | CD80 | DAP10 | FcγRIII-γ |
| IL13Ra2 | CD80 | DAP10 | FcεRIβ |
| IL13Ra2 | CD80 | DAP10 | FcεRIγ |
| IL13Ra2 | CD80 | DAP10 | DAP10 |
| IL13Ra2 | CD80 | DAP10 | DAP12 |
| IL13Ra2 | CD80 | DAP10 | CD32 |
| IL13Ra2 | CD80 | DAP10 | CD79a |
| IL13Ra2 | CD80 | DAP10 | CD79b |
| IL13Ra2 | CD80 | DAP12 | CD8 |
| IL13Ra2 | CD80 | DAP12 | CD3ζ |
| IL13Ra2 | CD80 | DAP12 | CD3δ |
| IL13Ra2 | CD80 | DAP12 | CD3γ |
| IL13Ra2 | CD80 | DAP12 | CD3ε |
| IL13Ra2 | CD80 | DAP12 | FcγRI-γ |
| IL13Ra2 | CD80 | DAP12 | FcγRIII-γ |
| IL13Ra2 | CD80 | DAP12 | FcεRIβ |
| IL13Ra2 | CD80 | DAP12 | FcεRIγ |
| IL13Ra2 | CD80 | DAP12 | DAP10 |
| IL13Ra2 | CD80 | DAP12 | DAP12 |
| IL13Ra2 | CD80 | DAP12 | CD32 |
| IL13Ra2 | CD80 | DAP12 | CD79a |
| IL13Ra2 | CD80 | DAP12 | CD79b |
| IL13Ra2 | CD80 | MyD88 | CD8 |
| IL13Ra2 | CD80 | MyD88 | CD3ζ |
| IL13Ra2 | CD80 | MyD88 | CD3δ |
| IL13Ra2 | CD80 | MyD88 | CD3γ |
| IL13Ra2 | CD80 | MyD88 | CD3ε |
| IL13Ra2 | CD80 | MyD88 | FcγRI-γ |
| IL13Ra2 | CD80 | MyD88 | FcγRIII-γ |
| IL13Ra2 | CD80 | MyD88 | FcεRIβ |
| IL13Ra2 | CD80 | MyD88 | FcεRIγ |
| IL13Ra2 | CD80 | MyD88 | DAP10 |
| IL13Ra2 | CD80 | MyD88 | DAP12 |
| IL13Ra2 | CD80 | MyD88 | CD32 |
| IL13Ra2 | CD80 | MyD88 | CD79a |
| IL13Ra2 | CD80 | MyD88 | CD79b |
| IL13Ra2 | CD80 | CD7 | CD8 |
| IL13Ra2 | CD80 | CD7 | CD3ζ |
| IL13Ra2 | CD80 | CD7 | CD3δ |
| IL13Ra2 | CD80 | CD7 | CD3γ |
| IL13Ra2 | CD80 | CD7 | CD3ε |
| IL13Ra2 | CD80 | CD7 | FcγRI-γ |
| IL13Ra2 | CD80 | CD7 | FcγRIII-γ |
| IL13Ra2 | CD80 | CD7 | FcεRIβ |
| IL13Ra2 | CD80 | CD7 | FcεRIγ |
| IL13Ra2 | CD80 | CD7 | DAP10 |
| IL13Ra2 | CD80 | CD7 | DAP12 |
| IL13Ra2 | CD80 | CD7 | CD32 |
| IL13Ra2 | CD80 | CD7 | CD79a |
| IL13Ra2 | CD80 | CD7 | CD79b |
| IL13Ra2 | CD80 | BTNL3 | CD8 |
| IL13Ra2 | CD80 | BTNL3 | CD3ζ |
| IL13Ra2 | CD80 | BTNL3 | CD3δ |
| IL13Ra2 | CD80 | BTNL3 | CD3γ |
| IL13Ra2 | CD80 | BTNL3 | CD3ε |
| IL13Ra2 | CD80 | BTNL3 | FcγRI-γ |
| IL13Ra2 | CD80 | BTNL3 | FcγRIII-γ |
| IL13Ra2 | CD80 | BTNL3 | FcεRIβ |
| IL13Ra2 | CD80 | BTNL3 | FcεRIγ |
| IL13Ra2 | CD80 | BTNL3 | DAP10 |
| IL13Ra2 | CD80 | BTNL3 | DAP12 |
| IL13Ra2 | CD80 | BTNL3 | CD32 |
| IL13Ra2 | CD80 | BTNL3 | CD79a |
| IL13Ra2 | CD80 | BTNL3 | CD79b |
| IL13Ra2 | CD80 | NKG2D | CD8 |
| IL13Ra2 | CD80 | NKG2D | CD3ζ |
| IL13Ra2 | CD80 | NKG2D | CD3δ |
| IL13Ra2 | CD80 | NKG2D | CD3γ |
| IL13Ra2 | CD80 | NKG2D | CD3ε |
| IL13Ra2 | CD80 | NKG2D | FcγRI-γ |
| IL13Ra2 | CD80 | NKG2D | FcγRIII-γ |
| IL13Ra2 | CD80 | NKG2D | FcεRIβ |
| IL13Ra2 | CD80 | NKG2D | FcεRIγ |
| IL13Ra2 | CD80 | NKG2D | DAP10 |
| IL13Ra2 | CD80 | NKG2D | DAP12 |
| IL13Ra2 | CD80 | NKG2D | CD32 |
| IL13Ra2 | CD80 | NKG2D | CD79a |
| IL13Ra2 | CD80 | NKG2D | CD79b |
| IL13Ra2 | CD86 | CD28 | CD8 |
| IL13Ra2 | CD86 | CD28 | CD3ζ |
| IL13Ra2 | CD86 | CD28 | CD3δ |
| IL13Ra2 | CD86 | CD28 | CD3γ |
| IL13Ra2 | CD86 | CD28 | CD3ε |
| IL13Ra2 | CD86 | CD28 | FcγRI-γ |
| IL13Ra2 | CD86 | CD28 | FcγRIII-γ |
| IL13Ra2 | CD86 | CD28 | FcεRIβ |
| IL13Ra2 | CD86 | CD28 | FcεRIγ |
| IL13Ra2 | CD86 | CD28 | DAP10 |
| IL13Ra2 | CD86 | CD28 | DAP12 |
| IL13Ra2 | CD86 | CD28 | CD32 |
| IL13Ra2 | CD86 | CD28 | CD79a |
| IL13Ra2 | CD86 | CD28 | CD79b |
| IL13Ra2 | CD86 | CD8 | CD8 |

TABLE 3-continued

Third Generation CARs

| ScFv | Co-stimulatory Signal | Co-stimulatory Signal | Signal Domain |
|---|---|---|---|
| IL13Ra2 | CD86 | CD8 | CD3ζ |
| IL13Ra2 | CD86 | CD8 | CD3δ |
| IL13Ra2 | CD86 | CD8 | CD3γ |
| IL13Ra2 | CD86 | CD8 | CD3ε |
| IL13Ra2 | CD86 | CD8 | FcγRI-γ |
| IL13Ra2 | CD86 | CD8 | FcγRIII-γ |
| IL13Ra2 | CD86 | CD8 | FcεRIβ |
| IL13Ra2 | CD86 | CD8 | FcεRIγ |
| IL13Ra2 | CD86 | CD8 | DAP10 |
| IL13Ra2 | CD86 | CD8 | DAP12 |
| IL13Ra2 | CD86 | CD8 | CD32 |
| IL13Ra2 | CD86 | CD8 | CD79a |
| IL13Ra2 | CD86 | CD8 | CD79b |
| IL13Ra2 | CD86 | CD4 | CD8 |
| IL13Ra2 | CD86 | CD4 | CD3ζ |
| IL13Ra2 | CD86 | CD4 | CD3δ |
| IL13Ra2 | CD86 | CD4 | CD3γ |
| IL13Ra2 | CD86 | CD4 | CD3ε |
| IL13Ra2 | CD86 | CD4 | FcγRI-γ |
| IL13Ra2 | CD86 | CD4 | FcγRIII-γ |
| IL13Ra2 | CD86 | CD4 | FcεRIβ |
| IL13Ra2 | CD86 | CD4 | FcεRIγ |
| IL13Ra2 | CD86 | CD4 | DAP10 |
| IL13Ra2 | CD86 | CD4 | DAP12 |
| IL13Ra2 | CD86 | CD4 | CD32 |
| IL13Ra2 | CD86 | CD4 | CD79a |
| IL13Ra2 | CD86 | CD4 | CD79b |
| IL13Ra2 | CD86 | b2c | CD8 |
| IL13Ra2 | CD86 | b2c | CD3ζ |
| IL13Ra2 | CD86 | b2c | CD3δ |
| IL13Ra2 | CD86 | b2c | CD3γ |
| IL13Ra2 | CD86 | b2c | CD3ε |
| IL13Ra2 | CD86 | b2c | FcγRI-γ |
| IL13Ra2 | CD86 | b2c | FcγRIII-γ |
| IL13Ra2 | CD86 | b2c | FcεRIβ |
| IL13Ra2 | CD86 | b2c | FcεRIγ |
| IL13Ra2 | CD86 | b2c | DAP10 |
| IL13Ra2 | CD86 | b2c | DAP12 |
| IL13Ra2 | CD86 | b2c | CD32 |
| IL13Ra2 | CD86 | b2c | CD79a |
| IL13Ra2 | CD86 | b2c | CD79b |
| IL13Ra2 | CD86 | CD137/41BB | CD8 |
| IL13Ra2 | CD86 | CD137/41BB | CD3ζ |
| IL13Ra2 | CD86 | CD137/41BB | CD3δ |
| IL13Ra2 | CD86 | CD137/41BB | CD3γ |
| IL13Ra2 | CD86 | CD137/41BB | CD3ε |
| IL13Ra2 | CD86 | CD137/41BB | FcγRI-γ |
| IL13Ra2 | CD86 | CD137/41BB | FcγRIII-γ |
| IL13Ra2 | CD86 | CD137/41BB | FcεRIβ |
| IL13Ra2 | CD86 | CD137/41BB | FcεRIγ |
| IL13Ra2 | CD86 | CD137/41BB | DAP10 |
| IL13Ra2 | CD86 | CD137/41BB | DAP12 |
| IL13Ra2 | CD86 | CD137/41BB | CD32 |
| IL13Ra2 | CD86 | CD137/41BB | CD79a |
| IL13Ra2 | CD86 | CD137/41BB | CD79b |
| IL13Ra2 | CD86 | ICOS | CD8 |
| IL13Ra2 | CD86 | ICOS | CD3ζ |
| IL13Ra2 | CD86 | ICOS | CD3δ |
| IL13Ra2 | CD86 | ICOS | CD3γ |
| IL13Ra2 | CD86 | ICOS | CD3ε |
| IL13Ra2 | CD86 | ICOS | FcγRI-γ |
| IL13Ra2 | CD86 | ICOS | FcγRIII-γ |
| IL13Ra2 | CD86 | ICOS | FcεRIβ |
| IL13Ra2 | CD86 | ICOS | FcεRIγ |
| IL13Ra2 | CD86 | ICOS | DAP10 |
| IL13Ra2 | CD86 | ICOS | DAP12 |
| IL13Ra2 | CD86 | ICOS | CD32 |
| IL13Ra2 | CD86 | ICOS | CD79a |
| IL13Ra2 | CD86 | ICOS | CD79b |
| IL13Ra2 | CD86 | CD27 | CD8 |
| IL13Ra2 | CD86 | CD27 | CD3ζ |
| IL13Ra2 | CD86 | CD27 | CD3δ |
| IL13Ra2 | CD86 | CD27 | CD3γ |
| IL13Ra2 | CD86 | CD27 | CD3ε |
| IL13Ra2 | CD86 | CD27 | FcγRI-γ |
| IL13Ra2 | CD86 | CD27 | FcγRIII-γ |
| IL13Ra2 | CD86 | CD27 | FcεRIβ |
| IL13Ra2 | CD86 | CD27 | FcεRIγ |
| IL13Ra2 | CD86 | CD27 | DAP10 |
| IL13Ra2 | CD86 | CD27 | DAP12 |
| IL13Ra2 | CD86 | CD27 | CD32 |
| IL13Ra2 | CD86 | CD27 | CD79a |
| IL13Ra2 | CD86 | CD27 | CD79b |
| IL13Ra2 | CD86 | CD28δ | CD8 |
| IL13Ra2 | CD86 | CD28δ | CD3ζ |
| IL13Ra2 | CD86 | CD28δ | CD3δ |
| IL13Ra2 | CD86 | CD28δ | CD3γ |
| IL13Ra2 | CD86 | CD28δ | CD3ε |
| IL13Ra2 | CD86 | CD28δ | FcγRI-γ |
| IL13Ra2 | CD86 | CD28δ | FcγRIII-γ |
| IL13Ra2 | CD86 | CD28δ | FcεRIβ |
| IL13Ra2 | CD86 | CD28δ | FcεRIγ |
| IL13Ra2 | CD86 | CD28δ | DAP10 |
| IL13Ra2 | CD86 | CD28δ | DAP12 |
| IL13Ra2 | CD86 | CD28δ | CD32 |
| IL13Ra2 | CD86 | CD28δ | CD79a |
| IL13Ra2 | CD86 | CD28δ | CD79b |
| IL13Ra2 | CD86 | CD80 | CD8 |
| IL13Ra2 | CD86 | CD80 | CD3ζ |
| IL13Ra2 | CD86 | CD80 | CD3δ |
| IL13Ra2 | CD86 | CD80 | CD3γ |
| IL13Ra2 | CD86 | CD80 | CD3ε |
| IL13Ra2 | CD86 | CD80 | FcγRI-γ |
| IL13Ra2 | CD86 | CD80 | FcγRIII-γ |
| IL13Ra2 | CD86 | CD80 | FcεRIβ |
| IL13Ra2 | CD86 | CD80 | FcεRIγ |
| IL13Ra2 | CD86 | CD80 | DAP10 |
| IL13Ra2 | CD86 | CD80 | DAP12 |
| IL13Ra2 | CD86 | CD80 | CD32 |
| IL13Ra2 | CD86 | CD80 | CD79a |
| IL13Ra2 | CD86 | CD80 | CD79b |
| IL13Ra2 | CD86 | CD86 | CD8 |
| IL13Ra2 | CD86 | CD86 | CD3ζ |
| IL13Ra2 | CD86 | CD86 | CD3δ |
| IL13Ra2 | CD86 | CD86 | CD3γ |
| IL13Ra2 | CD86 | CD86 | CD3ε |
| IL13Ra2 | CD86 | CD86 | FcγRI-γ |
| IL13Ra2 | CD86 | CD86 | FcγRIII-γ |
| IL13Ra2 | CD86 | CD86 | FcεRIβ |
| IL13Ra2 | CD86 | CD86 | FcεRIγ |
| IL13Ra2 | CD86 | CD86 | DAP10 |
| IL13Ra2 | CD86 | CD86 | DAP12 |
| IL13Ra2 | CD86 | CD86 | CD32 |
| IL13Ra2 | CD86 | CD86 | CD79a |
| IL13Ra2 | CD86 | CD86 | CD79b |
| IL13Ra2 | CD86 | OX40 | CD8 |
| IL13Ra2 | CD86 | OX40 | CD3ζ |
| IL13Ra2 | CD86 | OX40 | CD3δ |
| IL13Ra2 | CD86 | OX40 | CD3γ |
| IL13Ra2 | CD86 | OX40 | CD3ε |
| IL13Ra2 | CD86 | OX40 | FcγRI-γ |
| IL13Ra2 | CD86 | OX40 | FcγRIII-γ |
| IL13Ra2 | CD86 | OX40 | FcεRIβ |
| IL13Ra2 | CD86 | OX40 | FcεRIγ |
| IL13Ra2 | CD86 | OX40 | DAP10 |
| IL13Ra2 | CD86 | OX40 | DAP12 |
| IL13Ra2 | CD86 | OX40 | CD32 |
| IL13Ra2 | CD86 | OX40 | CD79a |
| IL13Ra2 | CD86 | OX40 | CD79b |
| IL13Ra2 | CD86 | DAP10 | CD8 |
| IL13Ra2 | CD86 | DAP10 | CD3ζ |
| IL13Ra2 | CD86 | DAP10 | CD3δ |
| IL13Ra2 | CD86 | DAP10 | CD3γ |
| IL13Ra2 | CD86 | DAP10 | CD3ε |
| IL13Ra2 | CD86 | DAP10 | FcγRI-γ |
| IL13Ra2 | CD86 | DAP10 | FcγRIII-γ |
| IL13Ra2 | CD86 | DAP10 | FcεRIβ |
| IL13Ra2 | CD86 | DAP10 | FcεRIγ |
| IL13Ra2 | CD86 | DAP10 | DAP10 |
| IL13Ra2 | CD86 | DAP10 | DAP12 |

TABLE 3-continued

| | Third Generation CARs | | | | Third Generation CARs | | |
|---|---|---|---|---|---|---|---|
| ScFv | Co-stimulatory Signal | Co-stimulatory Signal | Signal Domain | ScFv | Co-stimulatory Signal | Co-stimulatory Signal | Signal Domain |
| IL13Ra2 | CD86 | DAP10 | CD32 | IL13Ra2 | OX40 | CD28 | CD3δ |
| IL13Ra2 | CD86 | DAP10 | CD79a | IL13Ra2 | OX40 | CD28 | CD3γ |
| IL13Ra2 | CD86 | DAP10 | CD79b | IL13Ra2 | OX40 | CD28 | CD3ε |
| IL13Ra2 | CD86 | DAP12 | CD8 | IL13Ra2 | OX40 | CD28 | FcγRI-γ |
| IL13Ra2 | CD86 | DAP12 | CD3ζ | IL13Ra2 | OX40 | CD28 | FcγRIII-γ |
| IL13Ra2 | CD86 | DAP12 | CD3δ | IL13Ra2 | OX40 | CD28 | FcεRIβ |
| IL13Ra2 | CD86 | DAP12 | CD3γ | IL13Ra2 | OX40 | CD28 | FcεRIγ |
| IL13Ra2 | CD86 | DAP12 | CD3ε | IL13Ra2 | OX40 | CD28 | DAP10 |
| IL13Ra2 | CD86 | DAP12 | FcγRI-γ | IL13Ra2 | OX40 | CD28 | DAP12 |
| IL13Ra2 | CD86 | DAP12 | FcγRIII-γ | IL13Ra2 | OX40 | CD28 | CD32 |
| IL13Ra2 | CD86 | DAP12 | FcεRIβ | IL13Ra2 | OX40 | CD28 | CD79a |
| IL13Ra2 | CD86 | DAP12 | FcεRIγ | IL13Ra2 | OX40 | CD28 | CD79b |
| IL13Ra2 | CD86 | DAP12 | DAP10 | IL13Ra2 | OX40 | CD8 | CD8 |
| IL13Ra2 | CD86 | DAP12 | DAP12 | IL13Ra2 | OX40 | CD8 | CD3ζ |
| IL13Ra2 | CD86 | DAP12 | CD32 | IL13Ra2 | OX40 | CD8 | CD3δ |
| IL13Ra2 | CD86 | DAP12 | CD79a | IL13Ra2 | OX40 | CD8 | CD3γ |
| IL13Ra2 | CD86 | DAP12 | CD79b | IL13Ra2 | OX40 | CD8 | CD3ε |
| IL13Ra2 | CD86 | MyD88 | CD8 | IL13Ra2 | OX40 | CD8 | FcγRI-γ |
| IL13Ra2 | CD86 | MyD88 | CD3ζ | IL13Ra2 | OX40 | CD8 | FcγRIII-γ |
| IL13Ra2 | CD86 | MyD88 | CD3δ | IL13Ra2 | OX40 | CD8 | FcεRIβ |
| IL13Ra2 | CD86 | MyD88 | CD3γ | IL13Ra2 | OX40 | CD8 | FcεRIγ |
| IL13Ra2 | CD86 | MyD88 | CD3ε | IL13Ra2 | OX40 | CD8 | DAP10 |
| IL13Ra2 | CD86 | MyD88 | FcγRI-γ | IL13Ra2 | OX40 | CD8 | DAP12 |
| IL13Ra2 | CD86 | MyD88 | FcγRIII-γ | IL13Ra2 | OX40 | CD8 | CD32 |
| IL13Ra2 | CD86 | MyD88 | FcεRIβ | IL13Ra2 | OX40 | CD8 | CD79a |
| IL13Ra2 | CD86 | MyD88 | FcεRIγ | IL13Ra2 | OX40 | CD8 | CD79b |
| IL13Ra2 | CD86 | MyD88 | DAP10 | IL13Ra2 | OX40 | CD4 | CD8 |
| IL13Ra2 | CD86 | MyD88 | DAP12 | IL13Ra2 | OX40 | CD4 | CD3ζ |
| IL13Ra2 | CD86 | MyD88 | CD32 | IL13Ra2 | OX40 | CD4 | CD3δ |
| IL13Ra2 | CD86 | MyD88 | CD79a | IL13Ra2 | OX40 | CD4 | CD3γ |
| IL13Ra2 | CD86 | MyD88 | CD79b | IL13Ra2 | OX40 | CD4 | CD3ε |
| IL13Ra2 | CD86 | CD7 | CD8 | IL13Ra2 | OX40 | CD4 | FcγRI-γ |
| IL13Ra2 | CD86 | CD7 | CD3ζ | IL13Ra2 | OX40 | CD4 | FcγRIII-γ |
| IL13Ra2 | CD86 | CD7 | CD3δ | IL13Ra2 | OX40 | CD4 | FcεRIβ |
| IL13Ra2 | CD86 | CD7 | CD3γ | IL13Ra2 | OX40 | CD4 | FcεRIγ |
| IL13Ra2 | CD86 | CD7 | CD3ε | IL13Ra2 | OX40 | CD4 | DAP10 |
| IL13Ra2 | CD86 | CD7 | FcγRI-γ | IL13Ra2 | OX40 | CD4 | DAP12 |
| IL13Ra2 | CD86 | CD7 | FcγRIII-γ | IL13Ra2 | OX40 | CD4 | CD32 |
| IL13Ra2 | CD86 | CD7 | FcεRIβ | IL13Ra2 | OX40 | CD4 | CD79a |
| IL13Ra2 | CD86 | CD7 | FcεRIγ | IL13Ra2 | OX40 | CD4 | CD79b |
| IL13Ra2 | CD86 | CD7 | DAP10 | IL13Ra2 | OX40 | b2c | CD8 |
| IL13Ra2 | CD86 | CD7 | DAP12 | IL13Ra2 | OX40 | b2c | CD3ζ |
| IL13Ra2 | CD86 | CD7 | CD32 | IL13Ra2 | OX40 | b2c | CD3δ |
| IL13Ra2 | CD86 | CD7 | CD79a | IL13Ra2 | OX40 | b2c | CD3γ |
| IL13Ra2 | CD86 | CD7 | CD79b | IL13Ra2 | OX40 | b2c | CD3ε |
| IL13Ra2 | CD86 | BTNL3 | CD8 | IL13Ra2 | OX40 | b2c | FcγRI-γ |
| IL13Ra2 | CD86 | BTNL3 | CD3ζ | IL13Ra2 | OX40 | b2c | FcγRIII-γ |
| IL13Ra2 | CD86 | BTNL3 | CD3δ | IL13Ra2 | OX40 | b2c | FcεRIβ |
| IL13Ra2 | CD86 | BTNL3 | CD3γ | IL13Ra2 | OX40 | b2c | FcεRIγ |
| IL13Ra2 | CD86 | BTNL3 | CD3ε | IL13Ra2 | OX40 | b2c | DAP10 |
| IL13Ra2 | CD86 | BTNL3 | FcγRI-γ | IL13Ra2 | OX40 | b2c | DAP12 |
| IL13Ra2 | CD86 | BTNL3 | FcγRIII-γ | IL13Ra2 | OX40 | b2c | CD32 |
| IL13Ra2 | CD86 | BTNL3 | FcεRIβ | IL13Ra2 | OX40 | b2c | CD79a |
| IL13Ra2 | CD86 | BTNL3 | FcεRIγ | IL13Ra2 | OX40 | b2c | CD79b |
| IL13Ra2 | CD86 | BTNL3 | DAP10 | IL13Ra2 | OX40 | CD137/41BB | CD8 |
| IL13Ra2 | CD86 | BTNL3 | DAP12 | IL13Ra2 | OX40 | CD137/41BB | CD3ζ |
| IL13Ra2 | CD86 | BTNL3 | CD32 | IL13Ra2 | OX40 | CD137/41BB | CD3δ |
| IL13Ra2 | CD86 | BTNL3 | CD79a | IL13Ra2 | OX40 | CD137/41BB | CD3γ |
| IL13Ra2 | CD86 | BTNL3 | CD79b | IL13Ra2 | OX40 | CD137/41BB | CD3ε |
| IL13Ra2 | CD86 | NKG2D | CD8 | IL13Ra2 | OX40 | CD137/41BB | FcγRI-γ |
| IL13Ra2 | CD86 | NKG2D | CD3ζ | IL13Ra2 | OX40 | CD137/41BB | FcγRIII-γ |
| IL13Ra2 | CD86 | NKG2D | CD3δ | IL13Ra2 | OX40 | CD137/41BB | FcεRIβ |
| IL13Ra2 | CD86 | NKG2D | CD3γ | IL13Ra2 | OX40 | CD137/41BB | FcεRIγ |
| IL13Ra2 | CD86 | NKG2D | CD3ε | IL13Ra2 | OX40 | CD137/41BB | DAP10 |
| IL13Ra2 | CD86 | NKG2D | FcγRI-γ | IL13Ra2 | OX40 | CD137/41BB | DAP12 |
| IL13Ra2 | CD86 | NKG2D | FcγRIII-γ | IL13Ra2 | OX40 | CD137/41BB | CD32 |
| IL13Ra2 | CD86 | NKG2D | FcεRIβ | IL13Ra2 | OX40 | CD137/41BB | CD79a |
| IL13Ra2 | CD86 | NKG2D | FcεRIγ | IL13Ra2 | OX40 | CD137/41BB | CD79b |
| IL13Ra2 | CD86 | NKG2D | DAP10 | IL13Ra2 | OX40 | ICOS | CD8 |
| IL13Ra2 | CD86 | NKG2D | DAP12 | IL13Ra2 | OX40 | ICOS | CD3ζ |
| IL13Ra2 | CD86 | NKG2D | CD32 | IL13Ra2 | OX40 | ICOS | CD3δ |
| IL13Ra2 | CD86 | NKG2D | CD79a | IL13Ra2 | OX40 | ICOS | CD3γ |
| IL13Ra2 | CD86 | NKG2D | CD79b | IL13Ra2 | OX40 | ICOS | CD3ε |
| IL13Ra2 | OX40 | CD28 | CD8 | IL13Ra2 | OX40 | ICOS | FcγRI-γ |
| IL13Ra2 | OX40 | CD28 | CD3ζ | IL13Ra2 | OX40 | ICOS | FcγRIII-γ |

TABLE 3-continued

Third Generation CARs

| ScFv | Co-stimulatory Signal | Co-stimulatory Signal | Signal Domain |
|---|---|---|---|
| IL13Ra2 | OX40 | ICOS | FcεRIβ |
| IL13Ra2 | OX40 | ICOS | FcεRIγ |
| IL13Ra2 | OX40 | ICOS | DAP10 |
| IL13Ra2 | OX40 | ICOS | DAP12 |
| IL13Ra2 | OX40 | ICOS | CD32 |
| IL13Ra2 | OX40 | ICOS | CD79a |
| IL13Ra2 | OX40 | ICOS | CD79b |
| IL13Ra2 | OX40 | CD27 | CD8 |
| IL13Ra2 | OX40 | CD27 | CD3ζ |
| IL13Ra2 | OX40 | CD27 | CD3δ |
| IL13Ra2 | OX40 | CD27 | CD3γ |
| IL13Ra2 | OX40 | CD27 | CD3ε |
| IL13Ra2 | OX40 | CD27 | FcγRI-γ |
| IL13Ra2 | OX40 | CD27 | FcγRIII-γ |
| IL13Ra2 | OX40 | CD27 | FcεRIβ |
| IL13Ra2 | OX40 | CD27 | FcεRIγ |
| IL13Ra2 | OX40 | CD27 | DAP10 |
| IL13Ra2 | OX40 | CD27 | DAP12 |
| IL13Ra2 | OX40 | CD27 | CD32 |
| IL13Ra2 | OX40 | CD27 | CD79a |
| IL13Ra2 | OX40 | CD27 | CD79b |
| IL13Ra2 | OX40 | CD28δ | CD8 |
| IL13Ra2 | OX40 | CD28δ | CD3ζ |
| IL13Ra2 | OX40 | CD28δ | CD3δ |
| IL13Ra2 | OX40 | CD28δ | CD3γ |
| IL13Ra2 | OX40 | CD28δ | CD3ε |
| IL13Ra2 | OX40 | CD28δ | FcγRI-γ |
| IL13Ra2 | OX40 | CD28δ | FcγRIII-γ |
| IL13Ra2 | OX40 | CD28δ | FcεRIβ |
| IL13Ra2 | OX40 | CD28δ | FcεRIγ |
| IL13Ra2 | OX40 | CD28δ | DAP10 |
| IL13Ra2 | OX40 | CD28δ | DAP12 |
| IL13Ra2 | OX40 | CD28δ | CD32 |
| IL13Ra2 | OX40 | CD28δ | CD79a |
| IL13Ra2 | OX40 | CD28δ | CD79b |
| IL13Ra2 | OX40 | CD80 | CD8 |
| IL13Ra2 | OX40 | CD80 | CD3ζ |
| IL13Ra2 | OX40 | CD80 | CD3δ |
| IL13Ra2 | OX40 | CD80 | CD3γ |
| IL13Ra2 | OX40 | CD80 | CD3ε |
| IL13Ra2 | OX40 | CD80 | FcγRI-γ |
| IL13Ra2 | OX40 | CD80 | FcγRIII-γ |
| IL13Ra2 | OX40 | CD80 | FcεRIβ |
| IL13Ra2 | OX40 | CD80 | FcεRIγ |
| IL13Ra2 | OX40 | CD80 | DAP10 |
| IL13Ra2 | OX40 | CD80 | DAP12 |
| IL13Ra2 | OX40 | CD80 | CD32 |
| IL13Ra2 | OX40 | CD80 | CD79a |
| IL13Ra2 | OX40 | CD80 | CD79b |
| IL13Ra2 | OX40 | CD86 | CD8 |
| IL13Ra2 | OX40 | CD86 | CD3ζ |
| IL13Ra2 | OX40 | CD86 | CD3δ |
| IL13Ra2 | OX40 | CD86 | CD3γ |
| IL13Ra2 | OX40 | CD86 | CD3ε |
| IL13Ra2 | OX40 | CD86 | FcγRI-γ |
| IL13Ra2 | OX40 | CD86 | FcγRIII-γ |
| IL13Ra2 | OX40 | CD86 | FcεRIβ |
| IL13Ra2 | OX40 | CD86 | FcεRIγ |
| IL13Ra2 | OX40 | CD86 | DAP10 |
| IL13Ra2 | OX40 | CD86 | DAP12 |
| IL13Ra2 | OX40 | CD86 | CD32 |
| IL13Ra2 | OX40 | CD86 | CD79a |
| IL13Ra2 | OX40 | CD86 | CD79b |
| IL13Ra2 | OX40 | OX40 | CD8 |
| IL13Ra2 | OX40 | OX40 | CD3ζ |
| IL13Ra2 | OX40 | OX40 | CD3δ |
| IL13Ra2 | OX40 | OX40 | CD3γ |
| IL13Ra2 | OX40 | OX40 | CD3ε |
| IL13Ra2 | OX40 | OX40 | FcγRI-γ |
| IL13Ra2 | OX40 | OX40 | FcγRIII-γ |
| IL13Ra2 | OX40 | OX40 | FcεRIβ |
| IL13Ra2 | OX40 | OX40 | FcεRIγ |
| IL13Ra2 | OX40 | OX40 | DAP10 |
| IL13Ra2 | OX40 | OX40 | DAP12 |
| IL13Ra2 | OX40 | OX40 | CD32 |
| IL13Ra2 | OX40 | OX40 | CD79a |
| IL13Ra2 | OX40 | OX40 | CD79b |
| IL13Ra2 | OX40 | DAP10 | CD8 |
| IL13Ra2 | OX40 | DAP10 | CD3ζ |
| IL13Ra2 | OX40 | DAP10 | CD3δ |
| IL13Ra2 | OX40 | DAP10 | CD3γ |
| IL13Ra2 | OX40 | DAP10 | CD3ε |
| IL13Ra2 | OX40 | DAP10 | FcγRI-γ |
| IL13Ra2 | OX40 | DAP10 | FcγRIII-γ |
| IL13Ra2 | OX40 | DAP10 | FcεRIβ |
| IL13Ra2 | OX40 | DAP10 | FcεRIγ |
| IL13Ra2 | OX40 | DAP10 | DAP10 |
| IL13Ra2 | OX40 | DAP10 | DAP12 |
| IL13Ra2 | OX40 | DAP10 | CD32 |
| IL13Ra2 | OX40 | DAP10 | CD79a |
| IL13Ra2 | OX40 | DAP10 | CD79b |
| IL13Ra2 | OX40 | DAP12 | CD8 |
| IL13Ra2 | OX40 | DAP12 | CD3ζ |
| IL13Ra2 | OX40 | DAP12 | CD3δ |
| IL13Ra2 | OX40 | DAP12 | CD3γ |
| IL13Ra2 | OX40 | DAP12 | CD3ε |
| IL13Ra2 | OX40 | DAP12 | FcγRI-γ |
| IL13Ra2 | OX40 | DAP12 | FcγRIII-γ |
| IL13Ra2 | OX40 | DAP12 | FcεRIβ |
| IL13Ra2 | OX40 | DAP12 | FcεRIγ |
| IL13Ra2 | OX40 | DAP12 | DAP10 |
| IL13Ra2 | OX40 | DAP12 | DAP12 |
| IL13Ra2 | OX40 | DAP12 | CD32 |
| IL13Ra2 | OX40 | DAP12 | CD79a |
| IL13Ra2 | OX40 | DAP12 | CD79b |
| IL13Ra2 | OX40 | MyD88 | CD8 |
| IL13Ra2 | OX40 | MyD88 | CD3ζ |
| IL13Ra2 | OX40 | MyD88 | CD3δ |
| IL13Ra2 | OX40 | MyD88 | CD3γ |
| IL13Ra2 | OX40 | MyD88 | CD3ε |
| IL13Ra2 | OX40 | MyD88 | FcγRI-γ |
| IL13Ra2 | OX40 | MyD88 | FcγRIII-γ |
| IL13Ra2 | OX40 | MyD88 | FcεRIβ |
| IL13Ra2 | OX40 | MyD88 | FcεRIγ |
| IL13Ra2 | OX40 | MyD88 | DAP10 |
| IL13Ra2 | OX40 | MyD88 | DAP12 |
| IL13Ra2 | OX40 | MyD88 | CD32 |
| IL13Ra2 | OX40 | MyD88 | CD79a |
| IL13Ra2 | OX40 | MyD88 | CD79b |
| IL13Ra2 | OX40 | CD7 | CD8 |
| IL13Ra2 | OX40 | CD7 | CD3ζ |
| IL13Ra2 | OX40 | CD7 | CD3δ |
| IL13Ra2 | OX40 | CD7 | CD3γ |
| IL13Ra2 | OX40 | CD7 | CD3ε |
| IL13Ra2 | OX40 | CD7 | FcγRI-γ |
| IL13Ra2 | OX40 | CD7 | FcγRIII-γ |
| IL13Ra2 | OX40 | CD7 | FcεRIβ |
| IL13Ra2 | OX40 | CD7 | FcεRIγ |
| IL13Ra2 | OX40 | CD7 | DAP10 |
| IL13Ra2 | OX40 | CD7 | DAP12 |
| IL13Ra2 | OX40 | CD7 | CD32 |
| IL13Ra2 | OX40 | CD7 | CD79a |
| IL13Ra2 | OX40 | CD7 | CD79b |
| IL13Ra2 | OX40 | BTNL3 | CD8 |
| IL13Ra2 | OX40 | BTNL3 | CD3ζ |
| IL13Ra2 | OX40 | BTNL3 | CD3δ |
| IL13Ra2 | OX40 | BTNL3 | CD3γ |
| IL13Ra2 | OX40 | BTNL3 | CD3ε |
| IL13Ra2 | OX40 | BTNL3 | FcγRI-γ |
| IL13Ra2 | OX40 | BTNL3 | FcγRIII-γ |
| IL13Ra2 | OX40 | BTNL3 | FcεRIβ |
| IL13Ra2 | OX40 | BTNL3 | FcεRIγ |
| IL13Ra2 | OX40 | BTNL3 | DAP10 |
| IL13Ra2 | OX40 | BTNL3 | DAP12 |
| IL13Ra2 | OX40 | BTNL3 | CD32 |
| IL13Ra2 | OX40 | BTNL3 | CD79a |
| IL13Ra2 | OX40 | BTNL3 | CD79b |
| IL13Ra2 | OX40 | NKG2D | CD8 |
| IL13Ra2 | OX40 | NKG2D | CD3ζ |
| IL13Ra2 | OX40 | NKG2D | CD3δ |

TABLE 3-continued

Third Generation CARs

| ScFv | Co-stimulatory Signal | Co-stimulatory Signal | Signal Domain |
| --- | --- | --- | --- |
| IL13Ra2 | OX40 | NKG2D | CD3γ |
| IL13Ra2 | OX40 | NKG2D | CD3ε |
| IL13Ra2 | OX40 | NKG2D | FcγRI-γ |
| IL13Ra2 | OX40 | NKG2D | FcγRIII-γ |
| IL13Ra2 | OX40 | NKG2D | FcεRIβ |
| IL13Ra2 | OX40 | NKG2D | FcεRIγ |
| IL13Ra2 | OX40 | NKG2D | DAP10 |
| IL13Ra2 | OX40 | NKG2D | DAP12 |
| IL13Ra2 | OX40 | NKG2D | CD32 |
| IL13Ra2 | OX40 | NKG2D | CD79a |
| IL13Ra2 | OX40 | NKG2D | CD79b |
| IL13Ra2 | DAP10 | CD28 | CD8 |
| IL13Ra2 | DAP10 | CD28 | CD3ζ |
| IL13Ra2 | DAP10 | CD28 | CD3δ |
| IL13Ra2 | DAP10 | CD28 | CD3γ |
| IL13Ra2 | DAP10 | CD28 | CD3ε |
| IL13Ra2 | DAP10 | CD28 | FcγRI-γ |
| IL13Ra2 | DAP10 | CD28 | FcγRIII-γ |
| IL13Ra2 | DAP10 | CD28 | FcεRIβ |
| IL13Ra2 | DAP10 | CD28 | FcεRIγ |
| IL13Ra2 | DAP10 | CD28 | DAP10 |
| IL13Ra2 | DAP10 | CD28 | DAP12 |
| IL13Ra2 | DAP10 | CD28 | CD32 |
| IL13Ra2 | DAP10 | CD28 | CD79a |
| IL13Ra2 | DAP10 | CD28 | CD79b |
| IL13Ra2 | DAP10 | CD8 | CD8 |
| IL13Ra2 | DAP10 | CD8 | CD3ζ |
| IL13Ra2 | DAP10 | CD8 | CD3δ |
| IL13Ra2 | DAP10 | CD8 | CD3γ |
| IL13Ra2 | DAP10 | CD8 | CD3ε |
| IL13Ra2 | DAP10 | CD8 | FcγRI-γ |
| IL13Ra2 | DAP10 | CD8 | FcγRIII-γ |
| IL13Ra2 | DAP10 | CD8 | FcεRIβ |
| IL13Ra2 | DAP10 | CD8 | FcεRIγ |
| IL13Ra2 | DAP10 | CD8 | DAP10 |
| IL13Ra2 | DAP10 | CD8 | DAP12 |
| IL13Ra2 | DAP10 | CD8 | CD32 |
| IL13Ra2 | DAP10 | CD8 | CD79a |
| IL13Ra2 | DAP10 | CD8 | CD79b |
| IL13Ra2 | DAP10 | CD4 | CD8 |
| IL13Ra2 | DAP10 | CD4 | CD3ζ |
| IL13Ra2 | DAP10 | CD4 | CD3δ |
| IL13Ra2 | DAP10 | CD4 | CD3γ |
| IL13Ra2 | DAP10 | CD4 | CD3ε |
| IL13Ra2 | DAP10 | CD4 | FcγRI-γ |
| IL13Ra2 | DAP10 | CD4 | FcγRIII-γ |
| IL13Ra2 | DAP10 | CD4 | FcεRIβ |
| IL13Ra2 | DAP10 | CD4 | FcεRIγ |
| IL13Ra2 | DAP10 | CD4 | DAP10 |
| IL13Ra2 | DAP10 | CD4 | DAP12 |
| IL13Ra2 | DAP10 | CD4 | CD32 |
| IL13Ra2 | DAP10 | CD4 | CD79a |
| IL13Ra2 | DAP10 | CD4 | CD79b |
| IL13Ra2 | DAP10 | b2c | CD8 |
| IL13Ra2 | DAP10 | b2c | CD3ζ |
| IL13Ra2 | DAP10 | b2c | CD3δ |
| IL13Ra2 | DAP10 | b2c | CD3γ |
| IL13Ra2 | DAP10 | b2c | CD3ε |
| IL13Ra2 | DAP10 | b2c | FcγRI-γ |
| IL13Ra2 | DAP10 | b2c | FcγRIII-γ |
| IL13Ra2 | DAP10 | b2c | FcεRIβ |
| IL13Ra2 | DAP10 | b2c | FcεRIγ |
| IL13Ra2 | DAP10 | b2c | DAP10 |
| IL13Ra2 | DAP10 | b2c | DAP12 |
| IL13Ra2 | DAP10 | b2c | CD32 |
| IL13Ra2 | DAP10 | b2c | CD79a |
| IL13Ra2 | DAP10 | b2c | CD79b |
| IL13Ra2 | DAP10 | CD137/41BB | CD8 |
| IL13Ra2 | DAP10 | CD137/41BB | CD3ζ |
| IL13Ra2 | DAP10 | CD137/41BB | CD3δ |
| IL13Ra2 | DAP10 | CD137/41BB | CD3γ |
| IL13Ra2 | DAP10 | CD137/41BB | CD3ε |
| IL13Ra2 | DAP10 | CD137/41BB | FcγRI-γ |
| IL13Ra2 | DAP10 | CD137/41BB | FcγRIII-γ |
| IL13Ra2 | DAP10 | CD137/41BB | FcεRIβ |
| IL13Ra2 | DAP10 | CD137/41BB | FcεRIγ |
| IL13Ra2 | DAP10 | CD137/41BB | DAP10 |
| IL13Ra2 | DAP10 | CD137/41BB | DAP12 |
| IL13Ra2 | DAP10 | CD137/41BB | CD32 |
| IL13Ra2 | DAP10 | CD137/41BB | CD79a |
| IL13Ra2 | DAP10 | CD137/41BB | CD79b |
| IL13Ra2 | DAP10 | ICOS | CD8 |
| IL13Ra2 | DAP10 | ICOS | CD3ζ |
| IL13Ra2 | DAP10 | ICOS | CD3δ |
| IL13Ra2 | DAP10 | ICOS | CD3γ |
| IL13Ra2 | DAP10 | ICOS | CD3ε |
| IL13Ra2 | DAP10 | ICOS | FcγRI-γ |
| IL13Ra2 | DAP10 | ICOS | FcγRIII-γ |
| IL13Ra2 | DAP10 | ICOS | FcεRIβ |
| IL13Ra2 | DAP10 | ICOS | FcεRIγ |
| IL13Ra2 | DAP10 | ICOS | DAP10 |
| IL13Ra2 | DAP10 | ICOS | DAP12 |
| IL13Ra2 | DAP10 | ICOS | CD32 |
| IL13Ra2 | DAP10 | ICOS | CD79a |
| IL13Ra2 | DAP10 | ICOS | CD79b |
| IL13Ra2 | DAP10 | CD27 | CD8 |
| IL13Ra2 | DAP10 | CD27 | CD3ζ |
| IL13Ra2 | DAP10 | CD27 | CD3δ |
| IL13Ra2 | DAP10 | CD27 | CD3γ |
| IL13Ra2 | DAP10 | CD27 | CD3ε |
| IL13Ra2 | DAP10 | CD27 | FcγRI-γ |
| IL13Ra2 | DAP10 | CD27 | FcγRIII-γ |
| IL13Ra2 | DAP10 | CD27 | FcεRIβ |
| IL13Ra2 | DAP10 | CD27 | FcεRIγ |
| IL13Ra2 | DAP10 | CD27 | DAP10 |
| IL13Ra2 | DAP10 | CD27 | DAP12 |
| IL13Ra2 | DAP10 | CD27 | CD32 |
| IL13Ra2 | DAP10 | CD27 | CD79a |
| IL13Ra2 | DAP10 | CD27 | CD79b |
| IL13Ra2 | DAP10 | CD28δ | CD8 |
| IL13Ra2 | DAP10 | CD28δ | CD3ζ |
| IL13Ra2 | DAP10 | CD28δ | CD3δ |
| IL13Ra2 | DAP10 | CD28δ | CD3γ |
| IL13Ra2 | DAP10 | CD28δ | CD3ε |
| IL13Ra2 | DAP10 | CD28δ | FcγRI-γ |
| IL13Ra2 | DAP10 | CD28δ | FcγRIII-γ |
| IL13Ra2 | DAP10 | CD28δ | FcεRIβ |
| IL13Ra2 | DAP10 | CD28δ | FcεRIγ |
| IL13Ra2 | DAP10 | CD28δ | DAP10 |
| IL13Ra2 | DAP10 | CD28δ | DAP12 |
| IL13Ra2 | DAP10 | CD28δ | CD32 |
| IL13Ra2 | DAP10 | CD28δ | CD79a |
| IL13Ra2 | DAP10 | CD28δ | CD79b |
| IL13Ra2 | DAP10 | CD80 | CD8 |
| IL13Ra2 | DAP10 | CD80 | CD3ζ |
| IL13Ra2 | DAP10 | CD80 | CD3δ |
| IL13Ra2 | DAP10 | CD80 | CD3γ |
| IL13Ra2 | DAP10 | CD80 | CD3ε |
| IL13Ra2 | DAP10 | CD80 | FcγRI-γ |
| IL13Ra2 | DAP10 | CD80 | FcγRIII-γ |
| IL13Ra2 | DAP10 | CD80 | FcεRIβ |
| IL13Ra2 | DAP10 | CD80 | FcεRIγ |
| IL13Ra2 | DAP10 | CD80 | DAP10 |
| IL13Ra2 | DAP10 | CD80 | DAP12 |
| IL13Ra2 | DAP10 | CD80 | CD32 |
| IL13Ra2 | DAP10 | CD80 | CD79a |
| IL13Ra2 | DAP10 | CD80 | CD79b |
| IL13Ra2 | DAP10 | CD86 | CD8 |
| IL13Ra2 | DAP10 | CD86 | CD3ζ |
| IL13Ra2 | DAP10 | CD86 | CD3δ |
| IL13Ra2 | DAP10 | CD86 | CD3γ |
| IL13Ra2 | DAP10 | CD86 | CD3ε |
| IL13Ra2 | DAP10 | CD86 | FcγRI-γ |
| IL13Ra2 | DAP10 | CD86 | FcγRIII-γ |
| IL13Ra2 | DAP10 | CD86 | FcεRIβ |
| IL13Ra2 | DAP10 | CD86 | FcεRIγ |
| IL13Ra2 | DAP10 | CD86 | DAP10 |
| IL13Ra2 | DAP10 | CD86 | DAP12 |
| IL13Ra2 | DAP10 | CD86 | CD32 |
| IL13Ra2 | DAP10 | CD86 | CD79a |

TABLE 3-continued

Third Generation CARs

| ScFv | Co-stimulatory Signal | Co-stimulatory Signal | Signal Domain |
|---|---|---|---|
| IL13Ra2 | DAP10 | CD86 | CD79b |
| IL13Ra2 | DAP10 | OX40 | CD8 |
| IL13Ra2 | DAP10 | OX40 | CD3ζ |
| IL13Ra2 | DAP10 | OX40 | CD3δ |
| IL13Ra2 | DAP10 | OX40 | CD3γ |
| IL13Ra2 | DAP10 | OX40 | CD3ε |
| IL13Ra2 | DAP10 | OX40 | FcγRI-γ |
| IL13Ra2 | DAP10 | OX40 | FcγRIII-γ |
| IL13Ra2 | DAP10 | OX40 | FcεRIβ |
| IL13Ra2 | DAP10 | OX40 | FcεRIγ |
| IL13Ra2 | DAP10 | OX40 | DAP10 |
| IL13Ra2 | DAP10 | OX40 | DAP12 |
| IL13Ra2 | DAP10 | OX40 | CD32 |
| IL13Ra2 | DAP10 | OX40 | CD79a |
| IL13Ra2 | DAP10 | OX40 | CD79b |
| IL13Ra2 | DAP10 | DAP10 | CD8 |
| IL13Ra2 | DAP10 | DAP10 | CD3ζ |
| IL13Ra2 | DAP10 | DAP10 | CD3δ |
| IL13Ra2 | DAP10 | DAP10 | CD3γ |
| IL13Ra2 | DAP10 | DAP10 | CD3ε |
| IL13Ra2 | DAP10 | DAP10 | FcγRI-γ |
| IL13Ra2 | DAP10 | DAP10 | FcγRIII-γ |
| IL13Ra2 | DAP10 | DAP10 | FcεRIβ |
| IL13Ra2 | DAP10 | DAP10 | FcεRIγ |
| IL13Ra2 | DAP10 | DAP10 | DAP10 |
| IL13Ra2 | DAP10 | DAP10 | DAP12 |
| IL13Ra2 | DAP10 | DAP10 | CD32 |
| IL13Ra2 | DAP10 | DAP10 | CD79a |
| IL13Ra2 | DAP10 | DAP10 | CD79b |
| IL13Ra2 | DAP10 | DAP12 | CD8 |
| IL13Ra2 | DAP10 | DAP12 | CD3ζ |
| IL13Ra2 | DAP10 | DAP12 | CD3δ |
| IL13Ra2 | DAP10 | DAP12 | CD3γ |
| IL13Ra2 | DAP10 | DAP12 | CD3ε |
| IL13Ra2 | DAP10 | DAP12 | FcγRI-γ |
| IL13Ra2 | DAP10 | DAP12 | FcγRIII-γ |
| IL13Ra2 | DAP10 | DAP12 | FcεRIβ |
| IL13Ra2 | DAP10 | DAP12 | FcεRIγ |
| IL13Ra2 | DAP10 | DAP12 | DAP10 |
| IL13Ra2 | DAP10 | DAP12 | DAP12 |
| IL13Ra2 | DAP10 | DAP12 | CD32 |
| IL13Ra2 | DAP10 | DAP12 | CD79a |
| IL13Ra2 | DAP10 | DAP12 | CD79b |
| IL13Ra2 | DAP10 | MyD88 | CD8 |
| IL13Ra2 | DAP10 | MyD88 | CD3ζ |
| IL13Ra2 | DAP10 | MyD88 | CD3δ |
| IL13Ra2 | DAP10 | MyD88 | CD3γ |
| IL13Ra2 | DAP10 | MyD88 | CD3ε |
| IL13Ra2 | DAP10 | MyD88 | FcγRI-γ |
| IL13Ra2 | DAP10 | MyD88 | FcγRIII-γ |
| IL13Ra2 | DAP10 | MyD88 | FcεRIβ |
| IL13Ra2 | DAP10 | MyD88 | FcεRIγ |
| IL13Ra2 | DAP10 | MyD88 | DAP10 |
| IL13Ra2 | DAP10 | MyD88 | DAP12 |
| IL13Ra2 | DAP10 | MyD88 | CD32 |
| IL13Ra2 | DAP10 | MyD88 | CD79a |
| IL13Ra2 | DAP10 | MyD88 | CD79b |
| IL13Ra2 | DAP10 | CD7 | CD8 |
| IL13Ra2 | DAP10 | CD7 | CD3ζ |
| IL13Ra2 | DAP10 | CD7 | CD3δ |
| IL13Ra2 | DAP10 | CD7 | CD3γ |
| IL13Ra2 | DAP10 | CD7 | CD3ε |
| IL13Ra2 | DAP10 | CD7 | FcγRI-γ |
| IL13Ra2 | DAP10 | CD7 | FcγRIII-γ |
| IL13Ra2 | DAP10 | CD7 | FcεRIβ |
| IL13Ra2 | DAP10 | CD7 | FcεRIγ |
| IL13Ra2 | DAP10 | CD7 | DAP10 |
| IL13Ra2 | DAP10 | CD7 | DAP12 |
| IL13Ra2 | DAP10 | CD7 | CD32 |
| IL13Ra2 | DAP10 | CD7 | CD79a |
| IL13Ra2 | DAP10 | CD7 | CD79b |
| IL13Ra2 | DAP10 | BTNL3 | CD8 |
| IL13Ra2 | DAP10 | BTNL3 | CD3ζ |
| IL13Ra2 | DAP10 | BTNL3 | CD3δ |
| IL13Ra2 | DAP10 | BTNL3 | CD3γ |
| IL13Ra2 | DAP10 | BTNL3 | CD3ε |
| IL13Ra2 | DAP10 | BTNL3 | FcγRI-γ |
| IL13Ra2 | DAP10 | BTNL3 | FcγRIII-γ |
| IL13Ra2 | DAP10 | BTNL3 | FcεRIβ |
| IL13Ra2 | DAP10 | BTNL3 | FcεRIγ |
| IL13Ra2 | DAP10 | BTNL3 | DAP10 |
| IL13Ra2 | DAP10 | BTNL3 | DAP12 |
| IL13Ra2 | DAP10 | BTNL3 | CD32 |
| IL13Ra2 | DAP10 | BTNL3 | CD79a |
| IL13Ra2 | DAP10 | BTNL3 | CD79b |
| IL13Ra2 | DAP10 | NKG2D | CD8 |
| IL13Ra2 | DAP10 | NKG2D | CD3ζ |
| IL13Ra2 | DAP10 | NKG2D | CD3δ |
| IL13Ra2 | DAP10 | NKG2D | CD3γ |
| IL13Ra2 | DAP10 | NKG2D | CD3ε |
| IL13Ra2 | DAP10 | NKG2D | FcγRI-γ |
| IL13Ra2 | DAP10 | NKG2D | FcγRIII-γ |
| IL13Ra2 | DAP10 | NKG2D | FcεRIβ |
| IL13Ra2 | DAP10 | NKG2D | FcεRIγ |
| IL13Ra2 | DAP10 | NKG2D | DAP10 |
| IL13Ra2 | DAP10 | NKG2D | DAP12 |
| IL13Ra2 | DAP10 | NKG2D | CD32 |
| IL13Ra2 | DAP10 | NKG2D | CD79a |
| IL13Ra2 | DAP10 | NKG2D | CD79b |
| IL13Ra2 | DAP12 | CD28 | CD8 |
| IL13Ra2 | DAP12 | CD28 | CD3ζ |
| IL13Ra2 | DAP12 | CD28 | CD3δ |
| IL13Ra2 | DAP12 | CD28 | CD3γ |
| IL13Ra2 | DAP12 | CD28 | CD3ε |
| IL13Ra2 | DAP12 | CD28 | FcγRI-γ |
| IL13Ra2 | DAP12 | CD28 | FcγRIII-γ |
| IL13Ra2 | DAP12 | CD28 | FcεRIβ |
| IL13Ra2 | DAP12 | CD28 | FcεRIγ |
| IL13Ra2 | DAP12 | CD28 | DAP10 |
| IL13Ra2 | DAP12 | CD28 | DAP12 |
| IL13Ra2 | DAP12 | CD28 | CD32 |
| IL13Ra2 | DAP12 | CD28 | CD79a |
| IL13Ra2 | DAP12 | CD28 | CD79b |
| IL13Ra2 | DAP12 | CD8 | CD8 |
| IL13Ra2 | DAP12 | CD8 | CD3ζ |
| IL13Ra2 | DAP12 | CD8 | CD3δ |
| IL13Ra2 | DAP12 | CD8 | CD3γ |
| IL13Ra2 | DAP12 | CD8 | CD3ε |
| IL13Ra2 | DAP12 | CD8 | FcγRI-γ |
| IL13Ra2 | DAP12 | CD8 | FcγRIII-γ |
| IL13Ra2 | DAP12 | CD8 | FcεRIβ |
| IL13Ra2 | DAP12 | CD8 | FcεRIγ |
| IL13Ra2 | DAP12 | CD8 | DAP10 |
| IL13Ra2 | DAP12 | CD8 | DAP12 |
| IL13Ra2 | DAP12 | CD8 | CD32 |
| IL13Ra2 | DAP12 | CD8 | CD79a |
| IL13Ra2 | DAP12 | CD8 | CD79b |
| IL13Ra2 | DAP12 | CD4 | CD8 |
| IL13Ra2 | DAP12 | CD4 | CD3ζ |
| IL13Ra2 | DAP12 | CD4 | CD3δ |
| IL13Ra2 | DAP12 | CD4 | CD3γ |
| IL13Ra2 | DAP12 | CD4 | CD3ε |
| IL13Ra2 | DAP12 | CD4 | FcγRI-γ |
| IL13Ra2 | DAP12 | CD4 | FcγRIII-γ |
| IL13Ra2 | DAP12 | CD4 | FcεRIβ |
| IL13Ra2 | DAP12 | CD4 | FcεRIγ |
| IL13Ra2 | DAP12 | CD4 | DAP10 |
| IL13Ra2 | DAP12 | CD4 | DAP12 |
| IL13Ra2 | DAP12 | CD4 | CD32 |
| IL13Ra2 | DAP12 | CD4 | CD79a |
| IL13Ra2 | DAP12 | CD4 | CD79b |
| IL13Ra2 | DAP12 | b2c | CD8 |
| IL13Ra2 | DAP12 | b2c | CD3ζ |
| IL13Ra2 | DAP12 | b2c | CD3δ |
| IL13Ra2 | DAP12 | b2c | CD3γ |
| IL13Ra2 | DAP12 | b2c | CD3ε |
| IL13Ra2 | DAP12 | b2c | FcγRI-γ |
| IL13Ra2 | DAP12 | b2c | FcγRIII-γ |
| IL13Ra2 | DAP12 | b2c | FcεRIβ |
| IL13Ra2 | DAP12 | b2c | FcεRIγ |

TABLE 3-continued

Third Generation CARs

| ScFv | Co-stimulatory Signal | Co-stimulatory Signal | Signal Domain |
|---|---|---|---|
| IL13Ra2 | DAP12 | b2c | DAP10 |
| IL13Ra2 | DAP12 | b2c | DAP12 |
| IL13Ra2 | DAP12 | b2c | CD32 |
| IL13Ra2 | DAP12 | b2c | CD79a |
| IL13Ra2 | DAP12 | b2c | CD79b |
| IL13Ra2 | DAP12 | CD137/41BB | CD8 |
| IL13Ra2 | DAP12 | CD137/41BB | CD3ζ |
| IL13Ra2 | DAP12 | CD137/41BB | CD3δ |
| IL13Ra2 | DAP12 | CD137/41BB | CD3γ |
| IL13Ra2 | DAP12 | CD137/41BB | CD3ε |
| IL13Ra2 | DAP12 | CD137/41BB | FcγRI-γ |
| IL13Ra2 | DAP12 | CD137/41BB | FcγRIII-γ |
| IL13Ra2 | DAP12 | CD137/41BB | FcεRIβ |
| IL13Ra2 | DAP12 | CD137/41BB | FcεRIγ |
| IL13Ra2 | DAP12 | CD137/41BB | DAP10 |
| IL13Ra2 | DAP12 | CD137/41BB | DAP12 |
| IL13Ra2 | DAP12 | CD137/41BB | CD32 |
| IL13Ra2 | DAP12 | CD137/41BB | CD79a |
| IL13Ra2 | DAP12 | CD137/41BB | CD79b |
| IL13Ra2 | DAP12 | ICOS | CD8 |
| IL13Ra2 | DAP12 | ICOS | CD3ζ |
| IL13Ra2 | DAP12 | ICOS | CD3δ |
| IL13Ra2 | DAP12 | ICOS | CD3γ |
| IL13Ra2 | DAP12 | ICOS | CD3ε |
| IL13Ra2 | DAP12 | ICOS | FcγRI-γ |
| IL13Ra2 | DAP12 | ICOS | FcγRIII-γ |
| IL13Ra2 | DAP12 | ICOS | FcεRIβ |
| IL13Ra2 | DAP12 | ICOS | FcεRIγ |
| IL13Ra2 | DAP12 | ICOS | DAP10 |
| IL13Ra2 | DAP12 | ICOS | DAP12 |
| IL13Ra2 | DAP12 | ICOS | CD32 |
| IL13Ra2 | DAP12 | ICOS | CD79a |
| IL13Ra2 | DAP12 | ICOS | CD79b |
| IL13Ra2 | DAP12 | CD27 | CD8 |
| IL13Ra2 | DAP12 | CD27 | CD3ζ |
| IL13Ra2 | DAP12 | CD27 | CD3δ |
| IL13Ra2 | DAP12 | CD27 | CD3γ |
| IL13Ra2 | DAP12 | CD27 | CD3ε |
| IL13Ra2 | DAP12 | CD27 | FcγRI-γ |
| IL13Ra2 | DAP12 | CD27 | FcγRIII-γ |
| IL13Ra2 | DAP12 | CD27 | FcεRIβ |
| IL13Ra2 | DAP12 | CD27 | FcεRIγ |
| IL13Ra2 | DAP12 | CD27 | DAP10 |
| IL13Ra2 | DAP12 | CD27 | DAP12 |
| IL13Ra2 | DAP12 | CD27 | CD32 |
| IL13Ra2 | DAP12 | CD27 | CD79a |
| IL13Ra2 | DAP12 | CD27 | CD79b |
| IL13Ra2 | DAP12 | CD28δ | CD8 |
| IL13Ra2 | DAP12 | CD28δ | CD3ζ |
| IL13Ra2 | DAP12 | CD28δ | CD3δ |
| IL13Ra2 | DAP12 | CD28δ | CD3γ |
| IL13Ra2 | DAP12 | CD28δ | CD3ε |
| IL13Ra2 | DAP12 | CD28δ | FcγRI-γ |
| IL13Ra2 | DAP12 | CD28δ | FcγRIII-γ |
| IL13Ra2 | DAP12 | CD28δ | FcεRIβ |
| IL13Ra2 | DAP12 | CD28δ | FcεRIγ |
| IL13Ra2 | DAP12 | CD28δ | DAP10 |
| IL13Ra2 | DAP12 | CD28δ | DAP12 |
| IL13Ra2 | DAP12 | CD28δ | CD32 |
| IL13Ra2 | DAP12 | CD28δ | CD79a |
| IL13Ra2 | DAP12 | CD28δ | CD79b |
| IL13Ra2 | DAP12 | CD80 | CD8 |
| IL13Ra2 | DAP12 | CD80 | CD3ζ |
| IL13Ra2 | DAP12 | CD80 | CD3δ |
| IL13Ra2 | DAP12 | CD80 | CD3γ |
| IL13Ra2 | DAP12 | CD80 | CD3ε |
| IL13Ra2 | DAP12 | CD80 | FcγRI-γ |
| IL13Ra2 | DAP12 | CD80 | FcγRIII-γ |
| IL13Ra2 | DAP12 | CD80 | FcεRIβ |
| IL13Ra2 | DAP12 | CD80 | FcεRIγ |
| IL13Ra2 | DAP12 | CD80 | DAP10 |
| IL13Ra2 | DAP12 | CD80 | DAP12 |
| IL13Ra2 | DAP12 | CD80 | CD32 |
| IL13Ra2 | DAP12 | CD80 | CD79a |
| IL13Ra2 | DAP12 | CD80 | CD79b |
| IL13Ra2 | DAP12 | CD86 | CD8 |
| IL13Ra2 | DAP12 | CD86 | CD3ζ |
| IL13Ra2 | DAP12 | CD86 | CD3δ |
| IL13Ra2 | DAP12 | CD86 | CD3γ |
| IL13Ra2 | DAP12 | CD86 | CD3ε |
| IL13Ra2 | DAP12 | CD86 | FcγRI-γ |
| IL13Ra2 | DAP12 | CD86 | FcγRIII-γ |
| IL13Ra2 | DAP12 | CD86 | FcεRIβ |
| IL13Ra2 | DAP12 | CD86 | FcεRIγ |
| IL13Ra2 | DAP12 | CD86 | DAP10 |
| IL13Ra2 | DAP12 | CD86 | DAP12 |
| IL13Ra2 | DAP12 | CD86 | CD32 |
| IL13Ra2 | DAP12 | CD86 | CD79a |
| IL13Ra2 | DAP12 | CD86 | CD79b |
| IL13Ra2 | DAP12 | OX40 | CD8 |
| IL13Ra2 | DAP12 | OX40 | CD3ζ |
| IL13Ra2 | DAP12 | OX40 | CD3δ |
| IL13Ra2 | DAP12 | OX40 | CD3γ |
| IL13Ra2 | DAP12 | OX40 | CD3ε |
| IL13Ra2 | DAP12 | OX40 | FcγRI-γ |
| IL13Ra2 | DAP12 | OX40 | FcγRIII-γ |
| IL13Ra2 | DAP12 | OX40 | FcεRIβ |
| IL13Ra2 | DAP12 | OX40 | FcεRIγ |
| IL13Ra2 | DAP12 | OX40 | DAP10 |
| IL13Ra2 | DAP12 | OX40 | DAP12 |
| IL13Ra2 | DAP12 | OX40 | CD32 |
| IL13Ra2 | DAP12 | OX40 | CD79a |
| IL13Ra2 | DAP12 | OX40 | CD79b |
| IL13Ra2 | DAP12 | DAP10 | CD8 |
| IL13Ra2 | DAP12 | DAP10 | CD3ζ |
| IL13Ra2 | DAP12 | DAP10 | CD3δ |
| IL13Ra2 | DAP12 | DAP10 | CD3γ |
| IL13Ra2 | DAP12 | DAP10 | CD3ε |
| IL13Ra2 | DAP12 | DAP10 | FcγRI-γ |
| IL13Ra2 | DAP12 | DAP10 | FcγRIII-γ |
| IL13Ra2 | DAP12 | DAP10 | FcεRIβ |
| IL13Ra2 | DAP12 | DAP10 | FcεRIγ |
| IL13Ra2 | DAP12 | DAP10 | DAP10 |
| IL13Ra2 | DAP12 | DAP10 | DAP12 |
| IL13Ra2 | DAP12 | DAP10 | CD32 |
| IL13Ra2 | DAP12 | DAP10 | CD79a |
| IL13Ra2 | DAP12 | DAP10 | CD79b |
| IL13Ra2 | DAP12 | DAP12 | CD8 |
| IL13Ra2 | DAP12 | DAP12 | CD3ζ |
| IL13Ra2 | DAP12 | DAP12 | CD3δ |
| IL13Ra2 | DAP12 | DAP12 | CD3γ |
| IL13Ra2 | DAP12 | DAP12 | CD3ε |
| IL13Ra2 | DAP12 | DAP12 | FcγRI-γ |
| IL13Ra2 | DAP12 | DAP12 | FcγRIII-γ |
| IL13Ra2 | DAP12 | DAP12 | FcεRIβ |
| IL13Ra2 | DAP12 | DAP12 | FcεRIγ |
| IL13Ra2 | DAP12 | DAP12 | DAP10 |
| IL13Ra2 | DAP12 | DAP12 | DAP12 |
| IL13Ra2 | DAP12 | DAP12 | CD32 |
| IL13Ra2 | DAP12 | DAP12 | CD79a |
| IL13Ra2 | DAP12 | DAP12 | CD79b |
| IL13Ra2 | DAP12 | MyD88 | CD8 |
| IL13Ra2 | DAP12 | MyD88 | CD3ζ |
| IL13Ra2 | DAP12 | MyD88 | CD3δ |
| IL13Ra2 | DAP12 | MyD88 | CD3γ |
| IL13Ra2 | DAP12 | MyD88 | CD3ε |
| IL13Ra2 | DAP12 | MyD88 | FcγRI-γ |
| IL13Ra2 | DAP12 | MyD88 | FcγRIII-γ |
| IL13Ra2 | DAP12 | MyD88 | FcεRIβ |
| IL13Ra2 | DAP12 | MyD88 | FcεRIγ |
| IL13Ra2 | DAP12 | MyD88 | DAP10 |
| IL13Ra2 | DAP12 | MyD88 | DAP12 |
| IL13Ra2 | DAP12 | MyD88 | CD32 |
| IL13Ra2 | DAP12 | MyD88 | CD79a |
| IL13Ra2 | DAP12 | MyD88 | CD79b |
| IL13Ra2 | DAP12 | CD7 | CD8 |
| IL13Ra2 | DAP12 | CD7 | CD3ζ |
| IL13Ra2 | DAP12 | CD7 | CD3δ |
| IL13Ra2 | DAP12 | CD7 | CD3γ |
| IL13Ra2 | DAP12 | CD7 | CD3ε |

TABLE 3-continued

Third Generation CARs

| ScFv | Co-stimulatory Signal | Co-stimulatory Signal | Signal Domain |
|---|---|---|---|
| IL13Ra2 | DAP12 | CD7 | FcγRI-γ |
| IL13Ra2 | DAP12 | CD7 | FcγRIII-γ |
| IL13Ra2 | DAP12 | CD7 | FcεRIβ |
| IL13Ra2 | DAP12 | CD7 | FcεRIγ |
| IL13Ra2 | DAP12 | CD7 | DAP10 |
| IL13Ra2 | DAP12 | CD7 | DAP12 |
| IL13Ra2 | DAP12 | CD7 | CD32 |
| IL13Ra2 | DAP12 | CD7 | CD79a |
| IL13Ra2 | DAP12 | CD7 | CD79b |
| IL13Ra2 | DAP12 | BTNL3 | CD8 |
| IL13Ra2 | DAP12 | BTNL3 | CD3ζ |
| IL13Ra2 | DAP12 | BTNL3 | CD3δ |
| IL13Ra2 | DAP12 | BTNL3 | CD3γ |
| IL13Ra2 | DAP12 | BTNL3 | CD3ε |
| IL13Ra2 | DAP12 | BTNL3 | FcγRI-γ |
| IL13Ra2 | DAP12 | BTNL3 | FcγRIII-γ |
| IL13Ra2 | DAP12 | BTNL3 | FcεRIβ |
| IL13Ra2 | DAP12 | BTNL3 | FcεRIγ |
| IL13Ra2 | DAP12 | BTNL3 | DAP10 |
| IL13Ra2 | DAP12 | BTNL3 | DAP12 |
| IL13Ra2 | DAP12 | BTNL3 | CD32 |
| IL13Ra2 | DAP12 | BTNL3 | CD79a |
| IL13Ra2 | DAP12 | BTNL3 | CD79b |
| IL13Ra2 | DAP12 | NKG2D | CD8 |
| IL13Ra2 | DAP12 | NKG2D | CD3ζ |
| IL13Ra2 | DAP12 | NKG2D | CD3δ |
| IL13Ra2 | DAP12 | NKG2D | CD3γ |
| IL13Ra2 | DAP12 | NKG2D | CD3ε |
| IL13Ra2 | DAP12 | NKG2D | FcγRI-γ |
| IL13Ra2 | DAP12 | NKG2D | FcγRIII-γ |
| IL13Ra2 | DAP12 | NKG2D | FcεRIβ |
| IL13Ra2 | DAP12 | NKG2D | FcεRIγ |
| IL13Ra2 | DAP12 | NKG2D | DAP10 |
| IL13Ra2 | DAP12 | NKG2D | DAP12 |
| IL13Ra2 | DAP12 | NKG2D | CD32 |
| IL13Ra2 | DAP12 | NKG2D | CD79a |
| IL13Ra2 | DAP12 | NKG2D | CD79b |
| IL13Ra2 | MyD88 | CD28 | CD8 |
| IL13Ra2 | MyD88 | CD28 | CD3ζ |
| IL13Ra2 | MyD88 | CD28 | CD3δ |
| IL13Ra2 | MyD88 | CD28 | CD3γ |
| IL13Ra2 | MyD88 | CD28 | CD3ε |
| IL13Ra2 | MyD88 | CD28 | FcγRI-γ |
| IL13Ra2 | MyD88 | CD28 | FcγRIII-γ |
| IL13Ra2 | MyD88 | CD28 | FcεRIβ |
| IL13Ra2 | MyD88 | CD28 | FcεRIγ |
| IL13Ra2 | MyD88 | CD28 | DAP10 |
| IL13Ra2 | MyD88 | CD28 | DAP12 |
| IL13Ra2 | MyD88 | CD28 | CD32 |
| IL13Ra2 | MyD88 | CD28 | CD79a |
| IL13Ra2 | MyD88 | CD28 | CD79b |
| IL13Ra2 | MyD88 | CD8 | CD8 |
| IL13Ra2 | MyD88 | CD8 | CD3ζ |
| IL13Ra2 | MyD88 | CD8 | CD3δ |
| IL13Ra2 | MyD88 | CD8 | CD3γ |
| IL13Ra2 | MyD88 | CD8 | CD3ε |
| IL13Ra2 | MyD88 | CD8 | FcγRI-γ |
| IL13Ra2 | MyD88 | CD8 | FcγRIII-γ |
| IL13Ra2 | MyD88 | CD8 | FcεRIβ |
| IL13Ra2 | MyD88 | CD8 | FcεRIγ |
| IL13Ra2 | MyD88 | CD8 | DAP10 |
| IL13Ra2 | MyD88 | CD8 | DAP12 |
| IL13Ra2 | MyD88 | CD8 | CD32 |
| IL13Ra2 | MyD88 | CD8 | CD79a |
| IL13Ra2 | MyD88 | CD8 | CD79b |
| IL13Ra2 | MyD88 | CD4 | CD8 |
| IL13Ra2 | MyD88 | CD4 | CD3ζ |
| IL13Ra2 | MyD88 | CD4 | CD3δ |
| IL13Ra2 | MyD88 | CD4 | CD3γ |
| IL13Ra2 | MyD88 | CD4 | CD3ε |
| IL13Ra2 | MyD88 | CD4 | FcγRI-γ |
| IL13Ra2 | MyD88 | CD4 | FcγRIII-γ |
| IL13Ra2 | MyD88 | CD4 | FcεRIβ |
| IL13Ra2 | MyD88 | CD4 | FcεRIγ |
| IL13Ra2 | MyD88 | CD4 | DAP10 |
| IL13Ra2 | MyD88 | CD4 | DAP12 |
| IL13Ra2 | MyD88 | CD4 | CD32 |
| IL13Ra2 | MyD88 | CD4 | CD79a |
| IL13Ra2 | MyD88 | CD4 | CD79b |
| IL13Ra2 | MyD88 | b2c | CD8 |
| IL13Ra2 | MyD88 | b2c | CD3ζ |
| IL13Ra2 | MyD88 | b2c | CD3δ |
| IL13Ra2 | MyD88 | b2c | CD3γ |
| IL13Ra2 | MyD88 | b2c | CD3ε |
| IL13Ra2 | MyD88 | b2c | FcγRI-γ |
| IL13Ra2 | MyD88 | b2c | FcγRIII-γ |
| IL13Ra2 | MyD88 | b2c | FcεRIβ |
| IL13Ra2 | MyD88 | b2c | FcεRIγ |
| IL13Ra2 | MyD88 | b2c | DAP10 |
| IL13Ra2 | MyD88 | b2c | DAP12 |
| IL13Ra2 | MyD88 | b2c | CD32 |
| IL13Ra2 | MyD88 | b2c | CD79a |
| IL13Ra2 | MyD88 | b2c | CD79b |
| IL13Ra2 | MyD88 | CD137/41BB | CD8 |
| IL13Ra2 | MyD88 | CD137/41BB | CD3ζ |
| IL13Ra2 | MyD88 | CD137/41BB | CD3δ |
| IL13Ra2 | MyD88 | CD137/41BB | CD3γ |
| IL13Ra2 | MyD88 | CD137/41BB | CD3ε |
| IL13Ra2 | MyD88 | CD137/41BB | FcγRI-γ |
| IL13Ra2 | MyD88 | CD137/41BB | FcγRIII-γ |
| IL13Ra2 | MyD88 | CD137/41BB | FcεRIβ |
| IL13Ra2 | MyD88 | CD137/41BB | FcεRIγ |
| IL13Ra2 | MyD88 | CD137/41BB | DAP10 |
| IL13Ra2 | MyD88 | CD137/41BB | DAP12 |
| IL13Ra2 | MyD88 | CD137/41BB | CD32 |
| IL13Ra2 | MyD88 | CD137/41BB | CD79a |
| IL13Ra2 | MyD88 | CD137/41BB | CD79b |
| IL13Ra2 | MyD88 | ICOS | CD8 |
| IL13Ra2 | MyD88 | ICOS | CD3ζ |
| IL13Ra2 | MyD88 | ICOS | CD3δ |
| IL13Ra2 | MyD88 | ICOS | CD3γ |
| IL13Ra2 | MyD88 | ICOS | CD3ε |
| IL13Ra2 | MyD88 | ICOS | FcγRI-γ |
| IL13Ra2 | MyD88 | ICOS | FcγRIII-γ |
| IL13Ra2 | MyD88 | ICOS | FcεRIβ |
| IL13Ra2 | MyD88 | ICOS | FcεRIγ |
| IL13Ra2 | MyD88 | ICOS | DAP10 |
| IL13Ra2 | MyD88 | ICOS | DAP12 |
| IL13Ra2 | MyD88 | ICOS | CD32 |
| IL13Ra2 | MyD88 | ICOS | CD79a |
| IL13Ra2 | MyD88 | ICOS | CD79b |
| IL13Ra2 | MyD88 | CD27 | CD8 |
| IL13Ra2 | MyD88 | CD27 | CD3ζ |
| IL13Ra2 | MyD88 | CD27 | CD3δ |
| IL13Ra2 | MyD88 | CD27 | CD3γ |
| IL13Ra2 | MyD88 | CD27 | CD3ε |
| IL13Ra2 | MyD88 | CD27 | FcγRI-γ |
| IL13Ra2 | MyD88 | CD27 | FcγRIII-γ |
| IL13Ra2 | MyD88 | CD27 | FcεRIβ |
| IL13Ra2 | MyD88 | CD27 | FcεRIγ |
| IL13Ra2 | MyD88 | CD27 | DAP10 |
| IL13Ra2 | MyD88 | CD27 | DAP12 |
| IL13Ra2 | MyD88 | CD27 | CD32 |
| IL13Ra2 | MyD88 | CD27 | CD79a |
| IL13Ra2 | MyD88 | CD27 | CD79b |
| IL13Ra2 | MyD88 | CD28δ | CD8 |
| IL13Ra2 | MyD88 | CD28δ | CD3ζ |
| IL13Ra2 | MyD88 | CD28δ | CD3δ |
| IL13Ra2 | MyD88 | CD28δ | CD3γ |
| IL13Ra2 | MyD88 | CD28δ | CD3ε |
| IL13Ra2 | MyD88 | CD28δ | FcγRI-γ |
| IL13Ra2 | MyD88 | CD28δ | FcγRIII-γ |
| IL13Ra2 | MyD88 | CD28δ | FcεRIβ |
| IL13Ra2 | MyD88 | CD28δ | FcεRIγ |
| IL13Ra2 | MyD88 | CD28δ | DAP10 |
| IL13Ra2 | MyD88 | CD28δ | DAP12 |
| IL13Ra2 | MyD88 | CD28δ | CD32 |
| IL13Ra2 | MyD88 | CD28δ | CD79a |
| IL13Ra2 | MyD88 | CD28δ | CD79b |
| IL13Ra2 | MyD88 | CD80 | CD8 |

TABLE 3-continued

Third Generation CARs

| ScFv | Co-stimulatory Signal | Co-stimulatory Signal | Signal Domain |
|---|---|---|---|
| IL13Ra2 | MyD88 | CD80 | CD3ζ |
| IL13Ra2 | MyD88 | CD80 | CD3δ |
| IL13Ra2 | MyD88 | CD80 | CD3γ |
| IL13Ra2 | MyD88 | CD80 | CD3ε |
| IL13Ra2 | MyD88 | CD80 | FcγRI-γ |
| IL13Ra2 | MyD88 | CD80 | FcγRIII-γ |
| IL13Ra2 | MyD88 | CD80 | FcεRIβ |
| IL13Ra2 | MyD88 | CD80 | FcεRIγ |
| IL13Ra2 | MyD88 | CD80 | DAP10 |
| IL13Ra2 | MyD88 | CD80 | DAP12 |
| IL13Ra2 | MyD88 | CD80 | CD32 |
| IL13Ra2 | MyD88 | CD80 | CD79a |
| IL13Ra2 | MyD88 | CD80 | CD79b |
| IL13Ra2 | MyD88 | CD86 | CD8 |
| IL13Ra2 | MyD88 | CD86 | CD3ζ |
| IL13Ra2 | MyD88 | CD86 | CD3δ |
| IL13Ra2 | MyD88 | CD86 | CD3γ |
| IL13Ra2 | MyD88 | CD86 | CD3ε |
| IL13Ra2 | MyD88 | CD86 | FcγRI-γ |
| IL13Ra2 | MyD88 | CD86 | FcγRIII-γ |
| IL13Ra2 | MyD88 | CD86 | FcεRIβ |
| IL13Ra2 | MyD88 | CD86 | FcεRIγ |
| IL13Ra2 | MyD88 | CD86 | DAP10 |
| IL13Ra2 | MyD88 | CD86 | DAP12 |
| IL13Ra2 | MyD88 | CD86 | CD32 |
| IL13Ra2 | MyD88 | CD86 | CD79a |
| IL13Ra2 | MyD88 | CD86 | CD79b |
| IL13Ra2 | MyD88 | OX40 | CD8 |
| IL13Ra2 | MyD88 | OX40 | CD3ζ |
| IL13Ra2 | MyD88 | OX40 | CD3δ |
| IL13Ra2 | MyD88 | OX40 | CD3γ |
| IL13Ra2 | MyD88 | OX40 | CD3ε |
| IL13Ra2 | MyD88 | OX40 | FcγRI-γ |
| IL13Ra2 | MyD88 | OX40 | FcγRIII-γ |
| IL13Ra2 | MyD88 | OX40 | FcεRIβ |
| IL13Ra2 | MyD88 | OX40 | FcεRIγ |
| IL13Ra2 | MyD88 | OX40 | DAP10 |
| IL13Ra2 | MyD88 | OX40 | DAP12 |
| IL13Ra2 | MyD88 | OX40 | CD32 |
| IL13Ra2 | MyD88 | OX40 | CD79a |
| IL13Ra2 | MyD88 | OX40 | CD79b |
| IL13Ra2 | MyD88 | DAP10 | CD8 |
| IL13Ra2 | MyD88 | DAP10 | CD3ζ |
| IL13Ra2 | MyD88 | DAP10 | CD3δ |
| IL13Ra2 | MyD88 | DAP10 | CD3γ |
| IL13Ra2 | MyD88 | DAP10 | CD3ε |
| IL13Ra2 | MyD88 | DAP10 | FcγRI-γ |
| IL13Ra2 | MyD88 | DAP10 | FcγRIII-γ |
| IL13Ra2 | MyD88 | DAP10 | FcεRIβ |
| IL13Ra2 | MyD88 | DAP10 | FcεRIγ |
| IL13Ra2 | MyD88 | DAP10 | DAP10 |
| IL13Ra2 | MyD88 | DAP10 | DAP12 |
| IL13Ra2 | MyD88 | DAP10 | CD32 |
| IL13Ra2 | MyD88 | DAP10 | CD79a |
| IL13Ra2 | MyD88 | DAP10 | CD79b |
| IL13Ra2 | MyD88 | DAP12 | CD8 |
| IL13Ra2 | MyD88 | DAP12 | CD3ζ |
| IL13Ra2 | MyD88 | DAP12 | CD3δ |
| IL13Ra2 | MyD88 | DAP12 | CD3γ |
| IL13Ra2 | MyD88 | DAP12 | CD3ε |
| IL13Ra2 | MyD88 | DAP12 | FcγRI-γ |
| IL13Ra2 | MyD88 | DAP12 | FcγRIII-γ |
| IL13Ra2 | MyD88 | DAP12 | FcεRIβ |
| IL13Ra2 | MyD88 | DAP12 | FcεRIγ |
| IL13Ra2 | MyD88 | DAP12 | DAP10 |
| IL13Ra2 | MyD88 | DAP12 | DAP12 |
| IL13Ra2 | MyD88 | DAP12 | CD32 |
| IL13Ra2 | MyD88 | DAP12 | CD79a |
| IL13Ra2 | MyD88 | DAP12 | CD79b |
| IL13Ra2 | MyD88 | MyD88 | CD8 |
| IL13Ra2 | MyD88 | MyD88 | CD3ζ |
| IL13Ra2 | MyD88 | MyD88 | CD3δ |
| IL13Ra2 | MyD88 | MyD88 | CD3γ |
| IL13Ra2 | MyD88 | MyD88 | CD3ε |
| IL13Ra2 | MyD88 | MyD88 | FcγRI-γ |
| IL13Ra2 | MyD88 | MyD88 | FcγRIII-γ |
| IL13Ra2 | MyD88 | MyD88 | FcεRIβ |
| IL13Ra2 | MyD88 | MyD88 | FcεRIγ |
| IL13Ra2 | MyD88 | MyD88 | DAP10 |
| IL13Ra2 | MyD88 | MyD88 | DAP12 |
| IL13Ra2 | MyD88 | MyD88 | CD32 |
| IL13Ra2 | MyD88 | MyD88 | CD79a |
| IL13Ra2 | MyD88 | MyD88 | CD79b |
| IL13Ra2 | MyD88 | CD7 | CD8 |
| IL13Ra2 | MyD88 | CD7 | CD3ζ |
| IL13Ra2 | MyD88 | CD7 | CD3δ |
| IL13Ra2 | MyD88 | CD7 | CD3γ |
| IL13Ra2 | MyD88 | CD7 | CD3ε |
| IL13Ra2 | MyD88 | CD7 | FcγRI-γ |
| IL13Ra2 | MyD88 | CD7 | FcγRIII-γ |
| IL13Ra2 | MyD88 | CD7 | FcεRIβ |
| IL13Ra2 | MyD88 | CD7 | FcεRIγ |
| IL13Ra2 | MyD88 | CD7 | DAP10 |
| IL13Ra2 | MyD88 | CD7 | DAP12 |
| IL13Ra2 | MyD88 | CD7 | CD32 |
| IL13Ra2 | MyD88 | CD7 | CD79a |
| IL13Ra2 | MyD88 | CD7 | CD79b |
| IL13Ra2 | MyD88 | BTNL3 | CD8 |
| IL13Ra2 | MyD88 | BTNL3 | CD3ζ |
| IL13Ra2 | MyD88 | BTNL3 | CD3δ |
| IL13Ra2 | MyD88 | BTNL3 | CD3γ |
| IL13Ra2 | MyD88 | BTNL3 | CD3ε |
| IL13Ra2 | MyD88 | BTNL3 | FcγRI-γ |
| IL13Ra2 | MyD88 | BTNL3 | FcγRIII-γ |
| IL13Ra2 | MyD88 | BTNL3 | FcεRIβ |
| IL13Ra2 | MyD88 | BTNL3 | FcεRIγ |
| IL13Ra2 | MyD88 | BTNL3 | DAP10 |
| IL13Ra2 | MyD88 | BTNL3 | DAP12 |
| IL13Ra2 | MyD88 | BTNL3 | CD32 |
| IL13Ra2 | MyD88 | BTNL3 | CD79a |
| IL13Ra2 | MyD88 | BTNL3 | CD79b |
| IL13Ra2 | MyD88 | NKG2D | CD8 |
| IL13Ra2 | MyD88 | NKG2D | CD3ζ |
| IL13Ra2 | MyD88 | NKG2D | CD3δ |
| IL13Ra2 | MyD88 | NKG2D | CD3γ |
| IL13Ra2 | MyD88 | NKG2D | CD3ε |
| IL13Ra2 | MyD88 | NKG2D | FcγRI-γ |
| IL13Ra2 | MyD88 | NKG2D | FcγRIII-γ |
| IL13Ra2 | MyD88 | NKG2D | FcεRIβ |
| IL13Ra2 | MyD88 | NKG2D | FcεRIγ |
| IL13Ra2 | MyD88 | NKG2D | DAP10 |
| IL13Ra2 | MyD88 | NKG2D | DAP12 |
| IL13Ra2 | MyD88 | NKG2D | CD32 |
| IL13Ra2 | MyD88 | NKG2D | CD79a |
| IL13Ra2 | MyD88 | NKG2D | CD79b |
| IL13Ra2 | CD7 | CD28 | CD8 |
| IL13Ra2 | CD7 | CD28 | CD3ζ |
| IL13Ra2 | CD7 | CD28 | CD3δ |
| IL13Ra2 | CD7 | CD28 | CD3γ |
| IL13Ra2 | CD7 | CD28 | CD3ε |
| IL13Ra2 | CD7 | CD28 | FcγRI-γ |
| IL13Ra2 | CD7 | CD28 | FcγRIII-γ |
| IL13Ra2 | CD7 | CD28 | FcεRIβ |
| IL13Ra2 | CD7 | CD28 | FcεRIγ |
| IL13Ra2 | CD7 | CD28 | DAP10 |
| IL13Ra2 | CD7 | CD28 | DAP12 |
| IL13Ra2 | CD7 | CD28 | CD32 |
| IL13Ra2 | CD7 | CD28 | CD79a |
| IL13Ra2 | CD7 | CD28 | CD79b |
| IL13Ra2 | CD7 | CD8 | CD8 |
| IL13Ra2 | CD7 | CD8 | CD3ζ |
| IL13Ra2 | CD7 | CD8 | CD3δ |
| IL13Ra2 | CD7 | CD8 | CD3γ |
| IL13Ra2 | CD7 | CD8 | CD3ε |
| IL13Ra2 | CD7 | CD8 | FcγRI-γ |
| IL13Ra2 | CD7 | CD8 | FcγRIII-γ |
| IL13Ra2 | CD7 | CD8 | FcεRIβ |
| IL13Ra2 | CD7 | CD8 | FcεRIγ |
| IL13Ra2 | CD7 | CD8 | DAP10 |
| IL13Ra2 | CD7 | CD8 | DAP12 |

TABLE 3-continued

Third Generation CARs

| ScFv | Co-stimulatory Signal | Co-stimulatory Signal | Signal Domain |
|---|---|---|---|
| IL13Ra2 | CD7 | CD8 | CD32 |
| IL13Ra2 | CD7 | CD8 | CD79a |
| IL13Ra2 | CD7 | CD8 | CD79b |
| IL13Ra2 | CD7 | CD4 | CD8 |
| IL13Ra2 | CD7 | CD4 | CD3ζ |
| IL13Ra2 | CD7 | CD4 | CD3δ |
| IL13Ra2 | CD7 | CD4 | CD3γ |
| IL13Ra2 | CD7 | CD4 | CD3ε |
| IL13Ra2 | CD7 | CD4 | FcγRI-γ |
| IL13Ra2 | CD7 | CD4 | FcγRIII-γ |
| IL13Ra2 | CD7 | CD4 | FcεRIβ |
| IL13Ra2 | CD7 | CD4 | FcεRIγ |
| IL13Ra2 | CD7 | CD4 | DAP10 |
| IL13Ra2 | CD7 | CD4 | DAP12 |
| IL13Ra2 | CD7 | CD4 | CD32 |
| IL13Ra2 | CD7 | CD4 | CD79a |
| IL13Ra2 | CD7 | CD4 | CD79b |
| IL13Ra2 | CD7 | b2c | CD8 |
| IL13Ra2 | CD7 | b2c | CD3ζ |
| IL13Ra2 | CD7 | b2c | CD3δ |
| IL13Ra2 | CD7 | b2c | CD3γ |
| IL13Ra2 | CD7 | b2c | CD3ε |
| IL13Ra2 | CD7 | b2c | FcγRI-γ |
| IL13Ra2 | CD7 | b2c | FcγRIII-γ |
| IL13Ra2 | CD7 | b2c | FcεRIβ |
| IL13Ra2 | CD7 | b2c | FcεRIγ |
| IL13Ra2 | CD7 | b2c | DAP10 |
| IL13Ra2 | CD7 | b2c | DAP12 |
| IL13Ra2 | CD7 | b2c | CD32 |
| IL13Ra2 | CD7 | b2c | CD79a |
| IL13Ra2 | CD7 | b2c | CD79b |
| IL13Ra2 | CD7 | CD137/41BB | CD8 |
| IL13Ra2 | CD7 | CD137/41BB | CD3ζ |
| IL13Ra2 | CD7 | CD137/41BB | CD3δ |
| IL13Ra2 | CD7 | CD137/41BB | CD3γ |
| IL13Ra2 | CD7 | CD137/41BB | CD3ε |
| IL13Ra2 | CD7 | CD137/41BB | FcγRI-γ |
| IL13Ra2 | CD7 | CD137/41BB | FcγRIII-γ |
| IL13Ra2 | CD7 | CD137/41BB | FcεRIβ |
| IL13Ra2 | CD7 | CD137/41BB | FcεRIγ |
| IL13Ra2 | CD7 | CD137/41BB | DAP10 |
| IL13Ra2 | CD7 | CD137/41BB | DAP12 |
| IL13Ra2 | CD7 | CD137/41BB | CD32 |
| IL13Ra2 | CD7 | CD137/41BB | CD79a |
| IL13Ra2 | CD7 | CD137/41BB | CD79b |
| IL13Ra2 | CD7 | ICOS | CD8 |
| IL13Ra2 | CD7 | ICOS | CD3ζ |
| IL13Ra2 | CD7 | ICOS | CD3δ |
| IL13Ra2 | CD7 | ICOS | CD3γ |
| IL13Ra2 | CD7 | ICOS | CD3ε |
| IL13Ra2 | CD7 | ICOS | FcγRI-γ |
| IL13Ra2 | CD7 | ICOS | FcγRIII-γ |
| IL13Ra2 | CD7 | ICOS | FcεRIβ |
| IL13Ra2 | CD7 | ICOS | FcεRIγ |
| IL13Ra2 | CD7 | ICOS | DAP10 |
| IL13Ra2 | CD7 | ICOS | DAP12 |
| IL13Ra2 | CD7 | ICOS | CD32 |
| IL13Ra2 | CD7 | ICOS | CD79a |
| IL13Ra2 | CD7 | ICOS | CD79b |
| IL13Ra2 | CD7 | CD27 | CD8 |
| IL13Ra2 | CD7 | CD27 | CD3ζ |
| IL13Ra2 | CD7 | CD27 | CD3δ |
| IL13Ra2 | CD7 | CD27 | CD3γ |
| IL13Ra2 | CD7 | CD27 | CD3ε |
| IL13Ra2 | CD7 | CD27 | FcγRI-γ |
| IL13Ra2 | CD7 | CD27 | FcγRIII-γ |
| IL13Ra2 | CD7 | CD27 | FcεRIβ |
| IL13Ra2 | CD7 | CD27 | FcεRIγ |
| IL13Ra2 | CD7 | CD27 | DAP10 |
| IL13Ra2 | CD7 | CD27 | DAP12 |
| IL13Ra2 | CD7 | CD27 | CD32 |
| IL13Ra2 | CD7 | CD27 | CD79a |
| IL13Ra2 | CD7 | CD27 | CD79b |
| IL13Ra2 | CD7 | CD28δ | CD8 |
| IL13Ra2 | CD7 | CD28δ | CD3ζ |
| IL13Ra2 | CD7 | CD28δ | CD3δ |
| IL13Ra2 | CD7 | CD28δ | CD3γ |
| IL13Ra2 | CD7 | CD28δ | CD3ε |
| IL13Ra2 | CD7 | CD28δ | FcγRI-γ |
| IL13Ra2 | CD7 | CD28δ | FcγRIII-γ |
| IL13Ra2 | CD7 | CD28δ | FcεRIβ |
| IL13Ra2 | CD7 | CD28δ | FcεRIγ |
| IL13Ra2 | CD7 | CD28δ | DAP10 |
| IL13Ra2 | CD7 | CD28δ | DAP12 |
| IL13Ra2 | CD7 | CD28δ | CD32 |
| IL13Ra2 | CD7 | CD28δ | CD79a |
| IL13Ra2 | CD7 | CD28δ | CD79b |
| IL13Ra2 | CD7 | CD80 | CD8 |
| IL13Ra2 | CD7 | CD80 | CD3ζ |
| IL13Ra2 | CD7 | CD80 | CD3δ |
| IL13Ra2 | CD7 | CD80 | CD3γ |
| IL13Ra2 | CD7 | CD80 | CD3ε |
| IL13Ra2 | CD7 | CD80 | FcγRI-γ |
| IL13Ra2 | CD7 | CD80 | FcγRIII-γ |
| IL13Ra2 | CD7 | CD80 | FcεRIβ |
| IL13Ra2 | CD7 | CD80 | FcεRIγ |
| IL13Ra2 | CD7 | CD80 | DAP10 |
| IL13Ra2 | CD7 | CD80 | DAP12 |
| IL13Ra2 | CD7 | CD80 | CD32 |
| IL13Ra2 | CD7 | CD80 | CD79a |
| IL13Ra2 | CD7 | CD80 | CD79b |
| IL13Ra2 | CD7 | CD86 | CD8 |
| IL13Ra2 | CD7 | CD86 | CD3ζ |
| IL13Ra2 | CD7 | CD86 | CD3δ |
| IL13Ra2 | CD7 | CD86 | CD3γ |
| IL13Ra2 | CD7 | CD86 | CD3ε |
| IL13Ra2 | CD7 | CD86 | FcγRI-γ |
| IL13Ra2 | CD7 | CD86 | FcγRIII-γ |
| IL13Ra2 | CD7 | CD86 | FcεRIβ |
| IL13Ra2 | CD7 | CD86 | FcεRIγ |
| IL13Ra2 | CD7 | CD86 | DAP10 |
| IL13Ra2 | CD7 | CD86 | DAP12 |
| IL13Ra2 | CD7 | CD86 | CD32 |
| IL13Ra2 | CD7 | CD86 | CD79a |
| IL13Ra2 | CD7 | CD86 | CD79b |
| IL13Ra2 | CD7 | OX40 | CD8 |
| IL13Ra2 | CD7 | OX40 | CD3ζ |
| IL13Ra2 | CD7 | OX40 | CD3δ |
| IL13Ra2 | CD7 | OX40 | CD3γ |
| IL13Ra2 | CD7 | OX40 | CD3ε |
| IL13Ra2 | CD7 | OX40 | FcγRI-γ |
| IL13Ra2 | CD7 | OX40 | FcγRIII-γ |
| IL13Ra2 | CD7 | OX40 | FcεRIβ |
| IL13Ra2 | CD7 | OX40 | FcεRIγ |
| IL13Ra2 | CD7 | OX40 | DAP10 |
| IL13Ra2 | CD7 | OX40 | DAP12 |
| IL13Ra2 | CD7 | OX40 | CD32 |
| IL13Ra2 | CD7 | OX40 | CD79a |
| IL13Ra2 | CD7 | OX40 | CD79b |
| IL13Ra2 | CD7 | DAP10 | CD8 |
| IL13Ra2 | CD7 | DAP10 | CD3ζ |
| IL13Ra2 | CD7 | DAP10 | CD3δ |
| IL13Ra2 | CD7 | DAP10 | CD3γ |
| IL13Ra2 | CD7 | DAP10 | CD3ε |
| IL13Ra2 | CD7 | DAP10 | FcγRI-γ |
| IL13Ra2 | CD7 | DAP10 | FcγRIII-γ |
| IL13Ra2 | CD7 | DAP10 | FcεRIβ |
| IL13Ra2 | CD7 | DAP10 | FcεRIγ |
| IL13Ra2 | CD7 | DAP10 | DAP10 |
| IL13Ra2 | CD7 | DAP10 | DAP12 |
| IL13Ra2 | CD7 | DAP10 | CD32 |
| IL13Ra2 | CD7 | DAP10 | CD79a |
| IL13Ra2 | CD7 | DAP10 | CD79b |
| IL13Ra2 | CD7 | DAP12 | CD8 |
| IL13Ra2 | CD7 | DAP12 | CD3ζ |
| IL13Ra2 | CD7 | DAP12 | CD3δ |
| IL13Ra2 | CD7 | DAP12 | CD3γ |
| IL13Ra2 | CD7 | DAP12 | CD3ε |
| IL13Ra2 | CD7 | DAP12 | FcγRI-γ |
| IL13Ra2 | CD7 | DAP12 | FcγRIII-γ |

TABLE 3-continued

Third Generation CARs

| ScFv | Co-stimulatory Signal | Co-stimulatory Signal | Signal Domain |
|---|---|---|---|
| IL13Ra2 | CD7 | DAP12 | FcεRIβ |
| IL13Ra2 | CD7 | DAP12 | FcεRIγ |
| IL13Ra2 | CD7 | DAP12 | DAP10 |
| IL13Ra2 | CD7 | DAP12 | DAP12 |
| IL13Ra2 | CD7 | DAP12 | CD32 |
| IL13Ra2 | CD7 | DAP12 | CD79a |
| IL13Ra2 | CD7 | DAP12 | CD79b |
| IL13Ra2 | CD7 | MyD88 | CD8 |
| IL13Ra2 | CD7 | MyD88 | CD3ζ |
| IL13Ra2 | CD7 | MyD88 | CD3δ |
| IL13Ra2 | CD7 | MyD88 | CD3γ |
| IL13Ra2 | CD7 | MyD88 | CD3ε |
| IL13Ra2 | CD7 | MyD88 | FcγRI-γ |
| IL13Ra2 | CD7 | MyD88 | FcγRIII-γ |
| IL13Ra2 | CD7 | MyD88 | FcεRIβ |
| IL13Ra2 | CD7 | MyD88 | FcεRIγ |
| IL13Ra2 | CD7 | MyD88 | DAP10 |
| IL13Ra2 | CD7 | MyD88 | DAP12 |
| IL13Ra2 | CD7 | MyD88 | CD32 |
| IL13Ra2 | CD7 | MyD88 | CD79a |
| IL13Ra2 | CD7 | MyD88 | CD79b |
| IL13Ra2 | CD7 | CD7 | CD8 |
| IL13Ra2 | CD7 | CD7 | CD3ζ |
| IL13Ra2 | CD7 | CD7 | CD3δ |
| IL13Ra2 | CD7 | CD7 | CD3γ |
| IL13Ra2 | CD7 | CD7 | CD3ε |
| IL13Ra2 | CD7 | CD7 | FcγRI-γ |
| IL13Ra2 | CD7 | CD7 | FcγRIII-γ |
| IL13Ra2 | CD7 | CD7 | FcεRIβ |
| IL13Ra2 | CD7 | CD7 | FcεRIγ |
| IL13Ra2 | CD7 | CD7 | DAP10 |
| IL13Ra2 | CD7 | CD7 | DAP12 |
| IL13Ra2 | CD7 | CD7 | CD32 |
| IL13Ra2 | CD7 | CD7 | CD79a |
| IL13Ra2 | CD7 | CD7 | CD79b |
| IL13Ra2 | CD7 | BTNL3 | CD8 |
| IL13Ra2 | CD7 | BTNL3 | CD3ζ |
| IL13Ra2 | CD7 | BTNL3 | CD3δ |
| IL13Ra2 | CD7 | BTNL3 | CD3γ |
| IL13Ra2 | CD7 | BTNL3 | CD3ε |
| IL13Ra2 | CD7 | BTNL3 | FcγRI-γ |
| IL13Ra2 | CD7 | BTNL3 | FcγRIII-γ |
| IL13Ra2 | CD7 | BTNL3 | FcεRIβ |
| IL13Ra2 | CD7 | BTNL3 | FcεRIγ |
| IL13Ra2 | CD7 | BTNL3 | DAP10 |
| IL13Ra2 | CD7 | BTNL3 | DAP12 |
| IL13Ra2 | CD7 | BTNL3 | CD32 |
| IL13Ra2 | CD7 | BTNL3 | CD79a |
| IL13Ra2 | CD7 | BTNL3 | CD79b |
| IL13Ra2 | CD7 | NKG2D | CD8 |
| IL13Ra2 | CD7 | NKG2D | CD3ζ |
| IL13Ra2 | CD7 | NKG2D | CD3δ |
| IL13Ra2 | CD7 | NKG2D | CD3γ |
| IL13Ra2 | CD7 | NKG2D | CD3ε |
| IL13Ra2 | CD7 | NKG2D | FcγRI-γ |
| IL13Ra2 | CD7 | NKG2D | FcγRIII-γ |
| IL13Ra2 | CD7 | NKG2D | FcεRIβ |
| IL13Ra2 | CD7 | NKG2D | FcεRIγ |
| IL13Ra2 | CD7 | NKG2D | DAP10 |
| IL13Ra2 | CD7 | NKG2D | DAP12 |
| IL13Ra2 | CD7 | NKG2D | CD32 |
| IL13Ra2 | CD7 | NKG2D | CD79a |
| IL13Ra2 | CD7 | NKG2D | CD79b |
| IL13Ra2 | BTNL3 | CD28 | CD8 |
| IL13Ra2 | BTNL3 | CD28 | CD3ζ |
| IL13Ra2 | BTNL3 | CD28 | CD3δ |
| IL13Ra2 | BTNL3 | CD28 | CD3γ |
| IL13Ra2 | BTNL3 | CD28 | CD3ε |
| IL13Ra2 | BTNL3 | CD28 | FcγRI-γ |
| IL13Ra2 | BTNL3 | CD28 | FcγRIII-γ |
| IL13Ra2 | BTNL3 | CD28 | FcεRIβ |
| IL13Ra2 | BTNL3 | CD28 | FcεRIγ |
| IL13Ra2 | BTNL3 | CD28 | DAP10 |
| IL13Ra2 | BTNL3 | CD28 | DAP12 |
| IL13Ra2 | BTNL3 | CD28 | CD32 |
| IL13Ra2 | BTNL3 | CD28 | CD79a |
| IL13Ra2 | BTNL3 | CD28 | CD79b |
| IL13Ra2 | BTNL3 | CD8 | CD8 |
| IL13Ra2 | BTNL3 | CD8 | CD3ζ |
| IL13Ra2 | BTNL3 | CD8 | CD3δ |
| IL13Ra2 | BTNL3 | CD8 | CD3γ |
| IL13Ra2 | BTNL3 | CD8 | CD3ε |
| IL13Ra2 | BTNL3 | CD8 | FcγRI-γ |
| IL13Ra2 | BTNL3 | CD8 | FcγRIII-γ |
| IL13Ra2 | BTNL3 | CD8 | FcεRIβ |
| IL13Ra2 | BTNL3 | CD8 | FcεRIγ |
| IL13Ra2 | BTNL3 | CD8 | DAP10 |
| IL13Ra2 | BTNL3 | CD8 | DAP12 |
| IL13Ra2 | BTNL3 | CD8 | CD32 |
| IL13Ra2 | BTNL3 | CD8 | CD79a |
| IL13Ra2 | BTNL3 | CD8 | CD79b |
| IL13Ra2 | BTNL3 | CD4 | CD8 |
| IL13Ra2 | BTNL3 | CD4 | CD3ζ |
| IL13Ra2 | BTNL3 | CD4 | CD3δ |
| IL13Ra2 | BTNL3 | CD4 | CD3γ |
| IL13Ra2 | BTNL3 | CD4 | CD3ε |
| IL13Ra2 | BTNL3 | CD4 | FcγRI-γ |
| IL13Ra2 | BTNL3 | CD4 | FcγRIII-γ |
| IL13Ra2 | BTNL3 | CD4 | FcεRIβ |
| IL13Ra2 | BTNL3 | CD4 | FcεRIγ |
| IL13Ra2 | BTNL3 | CD4 | DAP10 |
| IL13Ra2 | BTNL3 | CD4 | DAP12 |
| IL13Ra2 | BTNL3 | CD4 | CD32 |
| IL13Ra2 | BTNL3 | CD4 | CD79a |
| IL13Ra2 | BTNL3 | CD4 | CD79b |
| IL13Ra2 | BTNL3 | b2c | CD8 |
| IL13Ra2 | BTNL3 | b2c | CD3ζ |
| IL13Ra2 | BTNL3 | b2c | CD3δ |
| IL13Ra2 | BTNL3 | b2c | CD3γ |
| IL13Ra2 | BTNL3 | b2c | CD3ε |
| IL13Ra2 | BTNL3 | b2c | FcγRI-γ |
| IL13Ra2 | BTNL3 | b2c | FcγRIII-γ |
| IL13Ra2 | BTNL3 | b2c | FcεRIβ |
| IL13Ra2 | BTNL3 | b2c | FcεRIγ |
| IL13Ra2 | BTNL3 | b2c | DAP10 |
| IL13Ra2 | BTNL3 | b2c | DAP12 |
| IL13Ra2 | BTNL3 | b2c | CD32 |
| IL13Ra2 | BTNL3 | b2c | CD79a |
| IL13Ra2 | BTNL3 | b2c | CD79b |
| IL13Ra2 | BTNL3 | CD137/41BB | CD8 |
| IL13Ra2 | BTNL3 | CD137/41BB | CD3ζ |
| IL13Ra2 | BTNL3 | CD137/41BB | CD3δ |
| IL13Ra2 | BTNL3 | CD137/41BB | CD3γ |
| IL13Ra2 | BTNL3 | CD137/41BB | CD3ε |
| IL13Ra2 | BTNL3 | CD137/41BB | FcγRI-γ |
| IL13Ra2 | BTNL3 | CD137/41BB | FcγRIII-γ |
| IL13Ra2 | BTNL3 | CD137/41BB | FcεRIβ |
| IL13Ra2 | BTNL3 | CD137/41BB | FcεRIγ |
| IL13Ra2 | BTNL3 | CD137/41BB | DAP10 |
| IL13Ra2 | BTNL3 | CD137/41BB | DAP12 |
| IL13Ra2 | BTNL3 | CD137/41BB | CD32 |
| IL13Ra2 | BTNL3 | CD137/41BB | CD79a |
| IL13Ra2 | BTNL3 | CD137/41BB | CD79b |
| IL13Ra2 | BTNL3 | ICOS | CD8 |
| IL13Ra2 | BTNL3 | ICOS | CD3ζ |
| IL13Ra2 | BTNL3 | ICOS | CD3δ |
| IL13Ra2 | BTNL3 | ICOS | CD3γ |
| IL13Ra2 | BTNL3 | ICOS | CD3ε |
| IL13Ra2 | BTNL3 | ICOS | FcγRI-γ |
| IL13Ra2 | BTNL3 | ICOS | FcγRIII-γ |
| IL13Ra2 | BTNL3 | ICOS | FcεRIβ |
| IL13Ra2 | BTNL3 | ICOS | FcεRIγ |
| IL13Ra2 | BTNL3 | ICOS | DAP10 |
| IL13Ra2 | BTNL3 | ICOS | DAP12 |
| IL13Ra2 | BTNL3 | ICOS | CD32 |
| IL13Ra2 | BTNL3 | ICOS | CD79a |
| IL13Ra2 | BTNL3 | ICOS | CD79b |
| IL13Ra2 | BTNL3 | CD27 | CD8 |
| IL13Ra2 | BTNL3 | CD27 | CD3ζ |
| IL13Ra2 | BTNL3 | CD27 | CD3δ |

TABLE 3-continued

Third Generation CARs

| ScFv | Co-stimulatory Signal | Co-stimulatory Signal | Signal Domain |
|---|---|---|---|
| IL13Ra2 | BTNL3 | CD27 | CD3γ |
| IL13Ra2 | BTNL3 | CD27 | CD3ε |
| IL13Ra2 | BTNL3 | CD27 | FcγRI-γ |
| IL13Ra2 | BTNL3 | CD27 | FcγRIII-γ |
| IL13Ra2 | BTNL3 | CD27 | FcεRIβ |
| IL13Ra2 | BTNL3 | CD27 | FcεRIγ |
| IL13Ra2 | BTNL3 | CD27 | DAP10 |
| IL13Ra2 | BTNL3 | CD27 | DAP12 |
| IL13Ra2 | BTNL3 | CD27 | CD32 |
| IL13Ra2 | BTNL3 | CD27 | CD79a |
| IL13Ra2 | BTNL3 | CD27 | CD79b |
| IL13Ra2 | BTNL3 | CD28δ | CD8 |
| IL13Ra2 | BTNL3 | CD28δ | CD3ζ |
| IL13Ra2 | BTNL3 | CD28δ | CD3δ |
| IL13Ra2 | BTNL3 | CD28δ | CD3γ |
| IL13Ra2 | BTNL3 | CD28δ | CD3ε |
| IL13Ra2 | BTNL3 | CD28δ | FcγRI-γ |
| IL13Ra2 | BTNL3 | CD28δ | FcγRIII-γ |
| IL13Ra2 | BTNL3 | CD28δ | FcεRIβ |
| IL13Ra2 | BTNL3 | CD28δ | FcεRIγ |
| IL13Ra2 | BTNL3 | CD28δ | DAP10 |
| IL13Ra2 | BTNL3 | CD28δ | DAP12 |
| IL13Ra2 | BTNL3 | CD28δ | CD32 |
| IL13Ra2 | BTNL3 | CD28δ | CD79a |
| IL13Ra2 | BTNL3 | CD28δ | CD79b |
| IL13Ra2 | BTNL3 | CD80 | CD8 |
| IL13Ra2 | BTNL3 | CD80 | CD3ζ |
| IL13Ra2 | BTNL3 | CD80 | CD3δ |
| IL13Ra2 | BTNL3 | CD80 | CD3γ |
| IL13Ra2 | BTNL3 | CD80 | CD3ε |
| IL13Ra2 | BTNL3 | CD80 | FcγRI-γ |
| IL13Ra2 | BTNL3 | CD80 | FcγRIII-γ |
| IL13Ra2 | BTNL3 | CD80 | FcεRIβ |
| IL13Ra2 | BTNL3 | CD80 | FcεRIγ |
| IL13Ra2 | BTNL3 | CD80 | DAP10 |
| IL13Ra2 | BTNL3 | CD80 | DAP12 |
| IL13Ra2 | BTNL3 | CD80 | CD32 |
| IL13Ra2 | BTNL3 | CD80 | CD79a |
| IL13Ra2 | BTNL3 | CD80 | CD79b |
| IL13Ra2 | BTNL3 | CD86 | CD8 |
| IL13Ra2 | BTNL3 | CD86 | CD3ζ |
| IL13Ra2 | BTNL3 | CD86 | CD3δ |
| IL13Ra2 | BTNL3 | CD86 | CD3γ |
| IL13Ra2 | BTNL3 | CD86 | CD3ε |
| IL13Ra2 | BTNL3 | CD86 | FcγRI-γ |
| IL13Ra2 | BTNL3 | CD86 | FcγRIII-γ |
| IL13Ra2 | BTNL3 | CD86 | FcεRIβ |
| IL13Ra2 | BTNL3 | CD86 | FcεRIγ |
| IL13Ra2 | BTNL3 | CD86 | DAP10 |
| IL13Ra2 | BTNL3 | CD86 | DAP12 |
| IL13Ra2 | BTNL3 | CD86 | CD32 |
| IL13Ra2 | BTNL3 | CD86 | CD79a |
| IL13Ra2 | BTNL3 | CD86 | CD79b |
| IL13Ra2 | BTNL3 | OX40 | CD8 |
| IL13Ra2 | BTNL3 | OX40 | CD3ζ |
| IL13Ra2 | BTNL3 | OX40 | CD3δ |
| IL13Ra2 | BTNL3 | OX40 | CD3γ |
| IL13Ra2 | BTNL3 | OX40 | CD3ε |
| IL13Ra2 | BTNL3 | OX40 | FcγRI-γ |
| IL13Ra2 | BTNL3 | OX40 | FcγRIII-γ |
| IL13Ra2 | BTNL3 | OX40 | FcεRIβ |
| IL13Ra2 | BTNL3 | OX40 | FcεRIγ |
| IL13Ra2 | BTNL3 | OX40 | DAP10 |
| IL13Ra2 | BTNL3 | OX40 | DAP12 |
| IL13Ra2 | BTNL3 | OX40 | CD32 |
| IL13Ra2 | BTNL3 | OX40 | CD79a |
| IL13Ra2 | BTNL3 | OX40 | CD79b |
| IL13Ra2 | BTNL3 | DAP10 | CD8 |
| IL13Ra2 | BTNL3 | DAP10 | CD3ζ |
| IL13Ra2 | BTNL3 | DAP10 | CD3δ |
| IL13Ra2 | BTNL3 | DAP10 | CD3γ |
| IL13Ra2 | BTNL3 | DAP10 | CD3ε |
| IL13Ra2 | BTNL3 | DAP10 | FcγRI-γ |
| IL13Ra2 | BTNL3 | DAP10 | FcγRIII-γ |
| IL13Ra2 | BTNL3 | DAP10 | FcεRIβ |
| IL13Ra2 | BTNL3 | DAP10 | FcεRIγ |
| IL13Ra2 | BTNL3 | DAP10 | DAP10 |
| IL13Ra2 | BTNL3 | DAP10 | DAP12 |
| IL13Ra2 | BTNL3 | DAP10 | CD32 |
| IL13Ra2 | BTNL3 | DAP10 | CD79a |
| IL13Ra2 | BTNL3 | DAP10 | CD79b |
| IL13Ra2 | BTNL3 | DAP12 | CD8 |
| IL13Ra2 | BTNL3 | DAP12 | CD3ζ |
| IL13Ra2 | BTNL3 | DAP12 | CD3δ |
| IL13Ra2 | BTNL3 | DAP12 | CD3γ |
| IL13Ra2 | BTNL3 | DAP12 | CD3ε |
| IL13Ra2 | BTNL3 | DAP12 | FcγRI-γ |
| IL13Ra2 | BTNL3 | DAP12 | FcγRIII-γ |
| IL13Ra2 | BTNL3 | DAP12 | FcεRIβ |
| IL13Ra2 | BTNL3 | DAP12 | FcεRIγ |
| IL13Ra2 | BTNL3 | DAP12 | DAP10 |
| IL13Ra2 | BTNL3 | DAP12 | DAP12 |
| IL13Ra2 | BTNL3 | DAP12 | CD32 |
| IL13Ra2 | BTNL3 | DAP12 | CD79a |
| IL13Ra2 | BTNL3 | DAP12 | CD79b |
| IL13Ra2 | BTNL3 | MyD88 | CD8 |
| IL13Ra2 | BTNL3 | MyD88 | CD3ζ |
| IL13Ra2 | BTNL3 | MyD88 | CD3δ |
| IL13Ra2 | BTNL3 | MyD88 | CD3γ |
| IL13Ra2 | BTNL3 | MyD88 | CD3ε |
| IL13Ra2 | BTNL3 | MyD88 | FcγRI-γ |
| IL13Ra2 | BTNL3 | MyD88 | FcγRIII-γ |
| IL13Ra2 | BTNL3 | MyD88 | FcεRIβ |
| IL13Ra2 | BTNL3 | MyD88 | FcεRIγ |
| IL13Ra2 | BTNL3 | MyD88 | DAP10 |
| IL13Ra2 | BTNL3 | MyD88 | DAP12 |
| IL13Ra2 | BTNL3 | MyD88 | CD32 |
| IL13Ra2 | BTNL3 | MyD88 | CD79a |
| IL13Ra2 | BTNL3 | MyD88 | CD79b |
| IL13Ra2 | BTNL3 | CD7 | CD8 |
| IL13Ra2 | BTNL3 | CD7 | CD3ζ |
| IL13Ra2 | BTNL3 | CD7 | CD3δ |
| IL13Ra2 | BTNL3 | CD7 | CD3γ |
| IL13Ra2 | BTNL3 | CD7 | CD3ε |
| IL13Ra2 | BTNL3 | CD7 | FcγRI-γ |
| IL13Ra2 | BTNL3 | CD7 | FcγRIII-γ |
| IL13Ra2 | BTNL3 | CD7 | FcεRIβ |
| IL13Ra2 | BTNL3 | CD7 | FcεRIγ |
| IL13Ra2 | BTNL3 | CD7 | DAP10 |
| IL13Ra2 | BTNL3 | CD7 | DAP12 |
| IL13Ra2 | BTNL3 | CD7 | CD32 |
| IL13Ra2 | BTNL3 | CD7 | CD79a |
| IL13Ra2 | BTNL3 | CD7 | CD79b |
| IL13Ra2 | BTNL3 | BTNL3 | CD8 |
| IL13Ra2 | BTNL3 | BTNL3 | CD3ζ |
| IL13Ra2 | BTNL3 | BTNL3 | CD3δ |
| IL13Ra2 | BTNL3 | BTNL3 | CD3γ |
| IL13Ra2 | BTNL3 | BTNL3 | CD3ε |
| IL13Ra2 | BTNL3 | BTNL3 | FcγRI-γ |
| IL13Ra2 | BTNL3 | BTNL3 | FcγRIII-γ |
| IL13Ra2 | BTNL3 | BTNL3 | FcεRIβ |
| IL13Ra2 | BTNL3 | BTNL3 | FcεRIγ |
| IL13Ra2 | BTNL3 | BTNL3 | DAP10 |
| IL13Ra2 | BTNL3 | BTNL3 | DAP12 |
| IL13Ra2 | BTNL3 | BTNL3 | CD32 |
| IL13Ra2 | BTNL3 | BTNL3 | CD79a |
| IL13Ra2 | BTNL3 | BTNL3 | CD79b |
| IL13Ra2 | BTNL3 | NKG2D | CD8 |
| IL13Ra2 | BTNL3 | NKG2D | CD3ζ |
| IL13Ra2 | BTNL3 | NKG2D | CD3δ |
| IL13Ra2 | BTNL3 | NKG2D | CD3γ |
| IL13Ra2 | BTNL3 | NKG2D | CD3ε |
| IL13Ra2 | BTNL3 | NKG2D | FcγRI-γ |
| IL13Ra2 | BTNL3 | NKG2D | FcγRIII-γ |
| IL13Ra2 | BTNL3 | NKG2D | FcεRIβ |
| IL13Ra2 | BTNL3 | NKG2D | FcεRIγ |
| IL13Ra2 | BTNL3 | NKG2D | DAP10 |
| IL13Ra2 | BTNL3 | NKG2D | DAP12 |
| IL13Ra2 | BTNL3 | NKG2D | CD32 |
| IL13Ra2 | BTNL3 | NKG2D | CD79a |

TABLE 3-continued

Third Generation CARs

| ScFv | Co-stimulatory Signal | Co-stimulatory Signal | Signal Domain |
|---|---|---|---|
| IL13Ra2 | BTNL3 | NKG2D | CD79b |
| IL13Ra2 | NKG2D | CD28 | CD8 |
| IL13Ra2 | NKG2D | CD28 | CD3ζ |
| IL13Ra2 | NKG2D | CD28 | CD3δ |
| IL13Ra2 | NKG2D | CD28 | CD3γ |
| IL13Ra2 | NKG2D | CD28 | CD3ε |
| IL13Ra2 | NKG2D | CD28 | FcγRI-γ |
| IL13Ra2 | NKG2D | CD28 | FcγRIII-γ |
| IL13Ra2 | NKG2D | CD28 | FcεRIβ |
| IL13Ra2 | NKG2D | CD28 | FcεRIγ |
| IL13Ra2 | NKG2D | CD28 | DAP10 |
| IL13Ra2 | NKG2D | CD28 | DAP12 |
| IL13Ra2 | NKG2D | CD28 | CD32 |
| IL13Ra2 | NKG2D | CD28 | CD79a |
| IL13Ra2 | NKG2D | CD28 | CD79b |
| IL13Ra2 | NKG2D | CD8 | CD8 |
| IL13Ra2 | NKG2D | CD8 | CD3ζ |
| IL13Ra2 | NKG2D | CD8 | CD3δ |
| IL13Ra2 | NKG2D | CD8 | CD3γ |
| IL13Ra2 | NKG2D | CD8 | CD3ε |
| IL13Ra2 | NKG2D | CD8 | FcγRI-γ |
| IL13Ra2 | NKG2D | CD8 | FcγRIII-γ |
| IL13Ra2 | NKG2D | CD8 | FcεRIβ |
| IL13Ra2 | NKG2D | CD8 | FcεRIγ |
| IL13Ra2 | NKG2D | CD8 | DAP10 |
| IL13Ra2 | NKG2D | CD8 | DAP12 |
| IL13Ra2 | NKG2D | CD8 | CD32 |
| IL13Ra2 | NKG2D | CD8 | CD79a |
| IL13Ra2 | NKG2D | CD8 | CD79b |
| IL13Ra2 | NKG2D | CD4 | CD8 |
| IL13Ra2 | NKG2D | CD4 | CD3ζ |
| IL13Ra2 | NKG2D | CD4 | CD3δ |
| IL13Ra2 | NKG2D | CD4 | CD3γ |
| IL13Ra2 | NKG2D | CD4 | CD3ε |
| IL13Ra2 | NKG2D | CD4 | FcγRI-γ |
| IL13Ra2 | NKG2D | CD4 | FcγRIII-γ |
| IL13Ra2 | NKG2D | CD4 | FcεRIβ |
| IL13Ra2 | NKG2D | CD4 | FcεRIγ |
| IL13Ra2 | NKG2D | CD4 | DAP10 |
| IL13Ra2 | NKG2D | CD4 | DAP12 |
| IL13Ra2 | NKG2D | CD4 | CD32 |
| IL13Ra2 | NKG2D | CD4 | CD79a |
| IL13Ra2 | NKG2D | CD4 | CD79b |
| IL13Ra2 | NKG2D | b2c | CD8 |
| IL13Ra2 | NKG2D | b2c | CD3ζ |
| IL13Ra2 | NKG2D | b2c | CD3δ |
| IL13Ra2 | NKG2D | b2c | CD3γ |
| IL13Ra2 | NKG2D | b2c | CD3ε |
| IL13Ra2 | NKG2D | b2c | FcγRI-γ |
| IL13Ra2 | NKG2D | b2c | FcγRIII-γ |
| IL13Ra2 | NKG2D | b2c | FcεRIβ |
| IL13Ra2 | NKG2D | b2c | FcεRIγ |
| IL13Ra2 | NKG2D | b2c | DAP10 |
| IL13Ra2 | NKG2D | b2c | DAP12 |
| IL13Ra2 | NKG2D | b2c | CD32 |
| IL13Ra2 | NKG2D | b2c | CD79a |
| IL13Ra2 | NKG2D | b2c | CD79b |
| IL13Ra2 | NKG2D | CD137/41BB | CD8 |
| IL13Ra2 | NKG2D | CD137/41BB | CD3ζ |
| IL13Ra2 | NKG2D | CD137/41BB | CD3δ |
| IL13Ra2 | NKG2D | CD137/41BB | CD3γ |
| IL13Ra2 | NKG2D | CD137/41BB | CD3ε |
| IL13Ra2 | NKG2D | CD137/41BB | FcγRI-γ |
| IL13Ra2 | NKG2D | CD137/41BB | FcγRIII-γ |
| IL13Ra2 | NKG2D | CD137/41BB | FcεRIβ |
| IL13Ra2 | NKG2D | CD137/41BB | FcεRIγ |
| IL13Ra2 | NKG2D | CD137/41BB | DAP10 |
| IL13Ra2 | NKG2D | CD137/41BB | DAP12 |
| IL13Ra2 | NKG2D | CD137/41BB | CD32 |
| IL13Ra2 | NKG2D | CD137/41BB | CD79a |
| IL13Ra2 | NKG2D | CD137/41BB | CD79b |
| IL13Ra2 | NKG2D | ICOS | CD8 |
| IL13Ra2 | NKG2D | ICOS | CD3ζ |
| IL13Ra2 | NKG2D | ICOS | CD3δ |
| IL13Ra2 | NKG2D | ICOS | CD3γ |
| IL13Ra2 | NKG2D | ICOS | CD3ε |
| IL13Ra2 | NKG2D | ICOS | FcγRI-γ |
| IL13Ra2 | NKG2D | ICOS | FcγRIII-γ |
| IL13Ra2 | NKG2D | ICOS | FcεRIβ |
| IL13Ra2 | NKG2D | ICOS | FcεRIγ |
| IL13Ra2 | NKG2D | ICOS | DAP10 |
| IL13Ra2 | NKG2D | ICOS | DAP12 |
| IL13Ra2 | NKG2D | ICOS | CD32 |
| IL13Ra2 | NKG2D | ICOS | CD79a |
| IL13Ra2 | NKG2D | ICOS | CD79b |
| IL13Ra2 | NKG2D | CD27 | CD8 |
| IL13Ra2 | NKG2D | CD27 | CD3ζ |
| IL13Ra2 | NKG2D | CD27 | CD3δ |
| IL13Ra2 | NKG2D | CD27 | CD3γ |
| IL13Ra2 | NKG2D | CD27 | CD3ε |
| IL13Ra2 | NKG2D | CD27 | FcγRI-γ |
| IL13Ra2 | NKG2D | CD27 | FcγRIII-γ |
| IL13Ra2 | NKG2D | CD27 | FcεRIβ |
| IL13Ra2 | NKG2D | CD27 | FcεRIγ |
| IL13Ra2 | NKG2D | CD27 | DAP10 |
| IL13Ra2 | NKG2D | CD27 | DAP12 |
| IL13Ra2 | NKG2D | CD27 | CD32 |
| IL13Ra2 | NKG2D | CD27 | CD79a |
| IL13Ra2 | NKG2D | CD27 | CD79b |
| IL13Ra2 | NKG2D | CD28δ | CD8 |
| IL13Ra2 | NKG2D | CD28δ | CD3ζ |
| IL13Ra2 | NKG2D | CD28δ | CD3δ |
| IL13Ra2 | NKG2D | CD28δ | CD3γ |
| IL13Ra2 | NKG2D | CD28δ | CD3ε |
| IL13Ra2 | NKG2D | CD28δ | FcγRI-γ |
| IL13Ra2 | NKG2D | CD28δ | FcγRIII-γ |
| IL13Ra2 | NKG2D | CD28δ | FcεRIβ |
| IL13Ra2 | NKG2D | CD28δ | FcεRIγ |
| IL13Ra2 | NKG2D | CD28δ | DAP10 |
| IL13Ra2 | NKG2D | CD28δ | DAP12 |
| IL13Ra2 | NKG2D | CD28δ | CD32 |
| IL13Ra2 | NKG2D | CD28δ | CD79a |
| IL13Ra2 | NKG2D | CD28δ | CD79b |
| IL13Ra2 | NKG2D | CD80 | CD8 |
| IL13Ra2 | NKG2D | CD80 | CD3ζ |
| IL13Ra2 | NKG2D | CD80 | CD3δ |
| IL13Ra2 | NKG2D | CD80 | CD3γ |
| IL13Ra2 | NKG2D | CD80 | CD3ε |
| IL13Ra2 | NKG2D | CD80 | FcγRI-γ |
| IL13Ra2 | NKG2D | CD80 | FcγRIII-γ |
| IL13Ra2 | NKG2D | CD80 | FcεRIβ |
| IL13Ra2 | NKG2D | CD80 | FcεRIγ |
| IL13Ra2 | NKG2D | CD80 | DAP10 |
| IL13Ra2 | NKG2D | CD80 | DAP12 |
| IL13Ra2 | NKG2D | CD80 | CD32 |
| IL13Ra2 | NKG2D | CD80 | CD79a |
| IL13Ra2 | NKG2D | CD80 | CD79b |
| IL13Ra2 | NKG2D | CD86 | CD8 |
| IL13Ra2 | NKG2D | CD86 | CD3ζ |
| IL13Ra2 | NKG2D | CD86 | CD3δ |
| IL13Ra2 | NKG2D | CD86 | CD3γ |
| IL13Ra2 | NKG2D | CD86 | CD3ε |
| IL13Ra2 | NKG2D | CD86 | FcγRI-γ |
| IL13Ra2 | NKG2D | CD86 | FcγRIII-γ |
| IL13Ra2 | NKG2D | CD86 | FcεRIβ |
| IL13Ra2 | NKG2D | CD86 | FcεRIγ |
| IL13Ra2 | NKG2D | CD86 | DAP10 |
| IL13Ra2 | NKG2D | CD86 | DAP12 |
| IL13Ra2 | NKG2D | CD86 | CD32 |
| IL13Ra2 | NKG2D | CD86 | CD79a |
| IL13Ra2 | NKG2D | CD86 | CD79b |
| IL13Ra2 | NKG2D | OX40 | CD8 |
| IL13Ra2 | NKG2D | OX40 | CD3ζ |
| IL13Ra2 | NKG2D | OX40 | CD3δ |
| IL13Ra2 | NKG2D | OX40 | CD3γ |
| IL13Ra2 | NKG2D | OX40 | CD3ε |
| IL13Ra2 | NKG2D | OX40 | FcγRI-γ |
| IL13Ra2 | NKG2D | OX40 | FcγRIII-γ |
| IL13Ra2 | NKG2D | OX40 | FcεRIβ |
| IL13Ra2 | NKG2D | OX40 | FcεRIγ |

TABLE 3-continued

Third Generation CARs

| ScFv | Co-stimulatory Signal | Co-stimulatory Signal | Signal Domain |
|---|---|---|---|
| IL13Ra2 | NKG2D | OX40 | DAP10 |
| IL13Ra2 | NKG2D | OX40 | DAP12 |
| IL13Ra2 | NKG2D | OX40 | CD32 |
| IL13Ra2 | NKG2D | OX40 | CD79a |
| IL13Ra2 | NKG2D | OX40 | CD79b |
| IL13Ra2 | NKG2D | DAP10 | CD8 |
| IL13Ra2 | NKG2D | DAP10 | CD3ζ |
| IL13Ra2 | NKG2D | DAP10 | CD3δ |
| IL13Ra2 | NKG2D | DAP10 | CD3γ |
| IL13Ra2 | NKG2D | DAP10 | CD3ε |
| IL13Ra2 | NKG2D | DAP10 | FcγRI-γ |
| IL13Ra2 | NKG2D | DAP10 | FcγRIII-γ |
| IL13Ra2 | NKG2D | DAP10 | FcεRIβ |
| IL13Ra2 | NKG2D | DAP10 | FcεRIγ |
| IL13Ra2 | NKG2D | DAP10 | DAP10 |
| IL13Ra2 | NKG2D | DAP10 | DAP12 |
| IL13Ra2 | NKG2D | DAP10 | CD32 |
| IL13Ra2 | NKG2D | DAP10 | CD79a |
| IL13Ra2 | NKG2D | DAP10 | CD79b |
| IL13Ra2 | NKG2D | DAP12 | CD8 |
| IL13Ra2 | NKG2D | DAP12 | CD3ζ |
| IL13Ra2 | NKG2D | DAP12 | CD3δ |
| IL13Ra2 | NKG2D | DAP12 | CD3γ |
| IL13Ra2 | NKG2D | DAP12 | CD3ε |
| IL13Ra2 | NKG2D | DAP12 | FcγRI-γ |
| IL13Ra2 | NKG2D | DAP12 | FcγRIII-γ |
| IL13Ra2 | NKG2D | DAP12 | FcεRIβ |
| IL13Ra2 | NKG2D | DAP12 | FcεRIγ |
| IL13Ra2 | NKG2D | DAP12 | DAP10 |
| IL13Ra2 | NKG2D | DAP12 | DAP12 |
| IL13Ra2 | NKG2D | DAP12 | CD32 |
| IL13Ra2 | NKG2D | DAP12 | CD79a |
| IL13Ra2 | NKG2D | DAP12 | CD79b |
| IL13Ra2 | NKG2D | MyD88 | CD8 |
| IL13Ra2 | NKG2D | MyD88 | CD3ζ |
| IL13Ra2 | NKG2D | MyD88 | CD3δ |
| IL13Ra2 | NKG2D | MyD88 | CD3γ |
| IL13Ra2 | NKG2D | MyD88 | CD3ε |
| IL13Ra2 | NKG2D | MyD88 | FcγRI-γ |
| IL13Ra2 | NKG2D | MyD88 | FcγRIII-γ |
| IL13Ra2 | NKG2D | MyD88 | FcεRIβ |
| IL13Ra2 | NKG2D | MyD88 | FcεRIγ |
| IL13Ra2 | NKG2D | MyD88 | DAP10 |
| IL13Ra2 | NKG2D | MyD88 | DAP12 |
| IL13Ra2 | NKG2D | MyD88 | CD32 |
| IL13Ra2 | NKG2D | MyD88 | CD79a |
| IL13Ra2 | NKG2D | MyD88 | CD79b |
| IL13Ra2 | NKG2D | CD7 | CD8 |
| IL13Ra2 | NKG2D | CD7 | CD3ζ |
| IL13Ra2 | NKG2D | CD7 | CD3δ |
| IL13Ra2 | NKG2D | CD7 | CD3γ |
| IL13Ra2 | NKG2D | CD7 | CD3ε |
| IL13Ra2 | NKG2D | CD7 | FcγRI-γ |
| IL13Ra2 | NKG2D | CD7 | FcγRIII-γ |
| IL13Ra2 | NKG2D | CD7 | FcεRIβ |
| IL13Ra2 | NKG2D | CD7 | FcεRIγ |
| IL13Ra2 | NKG2D | CD7 | DAP10 |
| IL13Ra2 | NKG2D | CD7 | DAP12 |
| IL13Ra2 | NKG2D | CD7 | CD32 |
| IL13Ra2 | NKG2D | CD7 | CD79a |
| IL13Ra2 | NKG2D | CD7 | CD79b |
| IL13Ra2 | NKG2D | BTNL3 | CD8 |
| IL13Ra2 | NKG2D | BTNL3 | CD3ζ |
| IL13Ra2 | NKG2D | BTNL3 | CD3δ |
| IL13Ra2 | NKG2D | BTNL3 | CD3γ |
| IL13Ra2 | NKG2D | BTNL3 | CD3ε |
| IL13Ra2 | NKG2D | BTNL3 | FcγRI-γ |
| IL13Ra2 | NKG2D | BTNL3 | FcγRIII-γ |
| IL13Ra2 | NKG2D | BTNL3 | FcεRIβ |
| IL13Ra2 | NKG2D | BTNL3 | FcεRIγ |
| IL13Ra2 | NKG2D | BTNL3 | DAP10 |
| IL13Ra2 | NKG2D | BTNL3 | DAP12 |
| IL13Ra2 | NKG2D | BTNL3 | CD32 |
| IL13Ra2 | NKG2D | BTNL3 | CD79a |
| IL13Ra2 | NKG2D | BTNL3 | CD79b |
| IL13Ra2 | NKG2D | NKG2D | CD8 |
| IL13Ra2 | NKG2D | NKG2D | CD3ζ |
| IL13Ra2 | NKG2D | NKG2D | CD3δ |
| IL13Ra2 | NKG2D | NKG2D | CD3γ |
| IL13Ra2 | NKG2D | NKG2D | CD3ε |
| IL13Ra2 | NKG2D | NKG2D | FcγRI-γ |
| IL13Ra2 | NKG2D | NKG2D | FcγRIII-γ |
| IL13Ra2 | NKG2D | NKG2D | FcεRIβ |
| IL13Ra2 | NKG2D | NKG2D | FcεRIγ |
| IL13Ra2 | NKG2D | NKG2D | DAP10 |
| IL13Ra2 | NKG2D | NKG2D | DAP12 |
| IL13Ra2 | NKG2D | NKG2D | CD32 |
| IL13Ra2 | NKG2D | NKG2D | CD79a |
| IL13Ra2 | NKG2D | NKG2D | CD79b |

In some embodiments, the anti-IL13Ra2 binding agent is single chain variable fragment (scFv) antibody. The affinity/specificity of an anti-IL13Ra2 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-IL13Ra2 $V_H$ domain comprises one, two, or three of the following CDR domains: CDR1: TKYGVH (SEQ ID NO:16), CDR2: VKWAGGSTDYNSALMS (SEQ ID NO:17), and CDR3: DHRDAMDY (SEQ ID NO:18). In some aspects, where the anti-IL13Ra2 $V_H$ domain can comprises two of the CDRs as set forth in SEQ ID Nos: 16, 17, and 18, it is understood and herein contemplated that any combination of two of those CDRs can be present. For example, SEQ ID NO: 16 and 18, SEQ ID NO: 16 and 17, or SEQ ID NO: 17 and 18.

In some embodiments, the anti-IL13Ra2 $V_L$T comprises one, two, or three of the following CDR domains: CDR1: TASLSVSSTYLH (SEQ ID NO:19), CDR2: SASYRST (SEQ ID NO:20), and CDR3: QHHYSAPWT (SEQ ID NO:21). In some aspects, where the anti-IL13Ra2 $V_L$ domain can comprises two of the CDRs as set forth in SEQ ID Nos: 19, 20, and 21, it is understood and herein contemplated that any combination of two of those CDRs can be present. For example, SEQ ID NO: 19 and 20, SEQ ID NO: 19 and 21, or SEQ ID NO: 20 and 21.

In some embodiments, the anti-IL13Ra2 $V_H$ domain comprises one, two, or three of the following CDR domains: CDR1: SRNGMS (SEQ ID NO:22), CDR2: TVSSGGSYIYYADSVKG (SEQ ID NO:23), and CDR3: QGTTALATRFFDV (SEQ ID NO:24). In some aspects, where the anti-IL13Ra2 $V_H$ domain can comprises two of the CDRs as set forth in SEQ ID Nos: 22, 23, and 24, it is understood and herein contemplated that any combination of two of those CDRs can be present. For example, SEQ ID NO: 22 and 23, SEQ ID NO: 22 and 24, or SEQ ID NO: 23 and 24.

In some embodiments, the anti-IL13Ra2 $V_L$T comprises one, two, or three of the following CDR domains: CDR1: KASQDVGTAVA (SEQ ID NO:25), CDR2: SASYRST (SEQ ID NO:26), and CDR3: QHHYSAPWT (SEQ ID NO:27). In some aspects, where the anti-IL13Ra2 $V_L$ domain can comprises two of the CDRs as set forth in SEQ ID Nos: 25, 26, and 27, it is understood and herein contemplated that any combination of two of those CDRs can be present. For example, SEQ ID NO: 25 and 26, SEQ ID NO: 25 and 27, or SEQ ID NO: 26 and 27.

It is further understood and herein contemplated that the anti-IL13Ra2 $V_H$ domain can comprise any combination of any of the $V_H$ domain CDRs disclosed herein including SEQ ID NOs: 16, 17, and 18; SEQ ID NOs:16, 17, and 24; SEQ ID NOs: 16, 23, and 18; SEQ ID NOs: 16, 23, and 24; SEQ ID NOs: 22, 23, and 24; SEQ ID NOs: 22, 23, and 18; SEQ ID NOs: 22, 17, and 18; or SEQ ID NOs: 22, 17, and 24. Similarly, is some aspects the anti-IL13Ra2 $V_L$ domain can comprise any combination of any of the $V_L$ domain CDRs disclosed herein including SEQ ID NOs: 19, 20, and 21; SEQ ID NOs:19, 20, and 27; SEQ ID NOs: 19, 26, and 22; SEQ ID NOs: 19, 26, and 27; SEQ ID NOs: 25, 26, and 27; SEQ ID NOs: 25, 26, and 21; SEQ ID NOs: 25, 20, and 27; or SEQ ID NOs: 25, 20, and 21. It is further understood and herein contemplated that any of the disclosed anti-IL13Ra2 $V_H$ domain CDR combinations can be combined with any of the disclosed anti-IL13Ra2 $V_L$ domain CDR combinations In some cases, the anti-IL13Ra2 $V_H$ domain comprises the amino acid sequence EVQLVESGGGLVQPGGSLRLSCAASGFTFSRNGMSWVRQAPGKGLEWVATVSSGGSYIYYADSVKGRFTISRDNAKNSLYLQMNSLRAEDTAVYYCARQGTTA LATRFFDVWGQGTLVTVSS (SEQ ID NO:1), or a fragment or variant thereof able to bind IL13Ra2.

In some cases, the anti-IL13Ra2 $V_H$ domain comprises the amino acid sequence EVQLVESGGGLVQPGGSLRLSCAASGFTFTKYGVHWVRQAPGKGLEWVAV KWAGGSTDYNSALMSRFTISRDNAKNSLYLQMNSLRAEDTAVYYCARDHR DAMDYWGQGTLVTVSS (SEQ ID NO:2), or a fragment or variant thereof able to bind IL13Ra2.

In some cases, the anti-IL13Ra2 $V_H$ domain comprises the amino acid sequence EVQLVESGGGLVQPGGSLRLSCAASGFTFSRNGMSWVRQTPDKRLEWVATVSSGGSYIYYADSVKGRFTISRDNAKNSLYLQMSSLRAEDTAVYYCARQGTTA LATRFFDVWGQGTLVTVSS (SEQ ID NO:28), or a fragment or variant thereof able to bind IL13Ra2.

In some cases, the anti-IL13Ra2 $V_H$ domain comprises the amino acid sequence EVQLVESGGGLVQPGGSLRLSCAASGFSLTKYGVHWVRQAPGKGLEWVGV KWAGGSTDYNSALMSRLTISRDNAKSSLYLQMNSLRAEDTAVYYCARDHRD AMDYWGQGTLVTVSS (SEQ ID NO:29), or a fragment or variant thereof able to bind IL13Ra2.

In some cases, the anti-IL13Ra2 $V_H$ domain comprises the amino acid sequence EVQLVESGGGLVQPGGSLRLSCAASGFTFTKYGVHWVRQAPGKGLEWVAV KWAGGSTDYNSALMSRFTISKDNAKNSLYLQMNSLRAEDTAVYYCARDHR DAMDYWGQGTLVTVSS (SEQ ID NO:30), or a fragment or variant thereof able to bind IL13Ra2.

In some cases, the anti-IL13Ra2 $V_H$ domain comprises the amino acid sequence EVQLVESGGGLVQPGGSLRLSCAASGFSLTKYGVHWVRQAPGKGLEWVAV KWAGGSTDYNSALMSRFTISKDNAKNSLYLQMNSLRAEDTAVYYCARDHR DAMDYWGQGTLVTVSS (SEQ ID NO:31), or a fragment or variant thereof able to bind IL13Ra2.

In some cases, the anti-IL13Ra2 $V_H$ domain comprises the amino acid sequence EVQLVESGGGLVQPGGSLRLSCAASGFSLTKYGVHWVRQAPGKGLEWVAV KWAGGSTDYNSALMSRFTISRDNAKNSLYLQMNSLRAEDTAVYYCARDHR DAMDYWGQGTLVTVSS (SEQ ID NO:32), or a fragment or variant thereof able to bind IL13Ra2.

In some cases, the anti-IL13Ra2 $V_H$ domain comprises the amino acid sequence EVQLVESGGGLVQPGGSLRLSCAASGFSLTKYGVHWVRQAPGKGLEWVGV KWAGGSTDYNSALMSRFTISKDNAKNSLYLQMNSLRAEDTAVYYCARDHR DAMDYWGQGTLVTVSS (SEQ ID NO:33), or a fragment or variant thereof able to bind IL13Ra2.

In some cases, the anti-IL13Ra2 $V_L$ domain comprises the amino acid sequence DIQMTQSPSSLSASVGDRVTITCKASQDVGTAVAWYQQKPGKAPKLLIYSAS YRSTGVPSRFSGSGSGTDFTLTISSLQPEDFATYYCQHHYSAPWTFGGGTKVEI K (SEQ ID NO:3), or a fragment or variant thereof able to bind IL13Ra2.

In some cases, the anti-IL13Ra2 $V_L$ domain comprises the amino acid sequence DDIQMTQSPSSLSASVGDRVTITCTASLSVSSTYLHWYQQKPGKAPKLLIYSTS NLASGVPSRFSGSGSGTDFTLTISSLQPEDFATYYCHQYHRSPLTFGGGTKVEI K (SEQ ID NO:4), or a fragment or variant thereof able to bind IL13Ra2.

In some cases, the anti-IL13Ra2 $V_L$ domain comprises the amino acid sequence DIQMTQSPSSLSASVGDRVTITCKASQDVGTAVAWYQQIPGKAPKLLIYSASY RSTGVPDRFSGSGSGTDFSFlISSLQPEDFATYYCQHHYSAPWTFGGGTKVEIK (SEQ ID NO:34), or a fragment or variant thereof able to bind IL13Ra2.

In some cases, the anti-IL13Ra2 $V_L$ domain comprises the amino acid sequence DIQMTQSPSSLSASVGDRVTITCTASLSVSSTYLHWYQQKPGSSPKLLIYSTSN LASGVPSRFSGSGSGTSFTLTISSLQPEDFATYYCHQYHRSPLTFGGGTKVEIK (SEQ ID NO:35), or a fragment or variant thereof able to bind IL13Ra2.

In some cases, the anti-IL13Ra2 $V_L$ domain comprises the amino acid sequence DIQMTQSPSSLSASVGDRVTITCTASLSVSSTYLHWYQQKPGKAPKLWIYSTS NLASGVPSRFSGSGSGTDFTLTISSLQPEDFATYYCHQYHRSPLTFGGGTKVEI K (SEQ ID NO:36), or a fragment or variant thereof able to bind IL13Ra2.

In some cases, the anti-IL13Ra2 $V_L$ domain comprises the amino acid sequence DIQMTQSPSSLSASVGDRVTITCTASLSVSSTYLHWYQQKPGKAPKLLIYSTSN LASGVPSRFSGSGSGTDYTLTISSLQPEDFATYYCHQYHRSPLTFGGGTKVEIK (SEQ ID NO:37), or a fragment or variant thereof able to bind IL13Ra2.

In some cases, the anti-IL13Ra2 $V_L$ domain comprises the amino acid sequence DIQMTQSPSSLSASVGDRVTITCTASLSVSSTYLHWYQQKPGKAPKLWIYSTS NLASGVPSRFSGSGSGTDYTLTISSLQPEDFATYYCHQYHRSPLTFGGGTKVEI K (SEQ ID NO:38), or a fragment or variant thereof able to bind IL13Ra2.

In some cases, the anti-IL13Ra2 $V_L$ domain comprises the amino acid sequence DIQMTQSPSSLSASVGDRVTITCTASLSVSSTYLHWYQQKPGSSPKLWIYSTSN LASGVPSRFSGSGSGTSFTLTISSLQPEDFATYYCHQYHRSPLTFGGGTKVEIK (SEQ ID NO:39), or a fragment or variant thereof able to bind IL13Ra2.

In some cases, the anti-IL13Ra2 V_L domain comprises the amino acid sequence (SEQ ID NO:40), or a fragment or variant thereof able to bind IL13Ra2.

In some cases, the anti-IL13Ra2 V_L domain comprises the amino acid sequence DIQMTQSPSSLSASVGDRVTITCTASLSVS-STYLHWYQQKPGSSPKLWIYSTSN LASGVPSRFSGSGSGTSYTLTISSLQPEDFATYY-CHQYHRSPLTFGGGTKVEIK (SEQ ID NO:41), or a fragment or variant thereof able to bind IL13Ra2.

In some cases, the anti-IL13Ra2 scFv comprises the amino acid sequence MVLLVTSLLLCELPHPAFLLIPE-VQLVESGGGLVQPGGSLRLSCAASGFTFSRN GMSWVRQAPGKGLEWVATVSSGGSYIYY-ADSVKGRFTISRDNAKNSLYLQM NSLRAEDTAVYY-CARQGTTALATRFFDVWGQGTLVTVSSGST-SGSGKPGSGE GSTKGDIQMTQSPSSLSASVGDRVTITCK-ASQDVGTAVAWYQQKPGKAPKLL IYSASYRSTGVPSRFSGSGSGTDFTLTISSLQPEDFA-TYYCQHHYSAPWTFGGG TKVEIK (SEQ ID NO:5), or a fragment or variant thereof able to bind IL13Ra2.

In some cases, the anti-IL13Ra2 scFv comprises the amino acid sequence MVLLVTSLLLCELPHPAFLLIPEVQLVESGG-GLVQPGGSLRLSCAASGFTFTK YGVHWVRQAPGK-GLEWVAVKWAGGSTDYNSALMSRFTISRDNAKNS-LYLQ MNSLRAEDTAVYYCARDHR-DAMDYWGQGTLVTVSSGSTSGSGKPGSGEGS TKGDIQMTQSPSSLSASVGDRVTITCTASLSVS-STYLHWYQQKPGKAPKLLIY STSN-LASGVPSRFSGSGSGTDFTLTISSLQPEDFATYY-CHQYHRSPLTFGGGTK VEIK (SEQ ID NO:6), or a fragment or variant thereof able to bind IL13Ra2.

In some cases, the anti-IL13Ra2 scFv is encoded by the nucleic acid sequence
ATGGTGTTGCTTGTGA-CATCTCTGCTGTTGTGCGAGCTCCCGCACCCAGCG TTTCTGCTCATCCCAGAAGTTCAACTGGTT-GAAAGTGGCGGCGGCTTGGTT CAGCCCGGTGGGTCTTTGCGATT-GAGTTGCGCCGCCAGTGGTTTTACATTC ACAAAATATGGAGTT-CACTGGGTACGACAAGCGCCTGGCAAGGGCCTTGA ATGGGTAGCAGTCAAGTGGGCTGGGGGTTCAACA-GATTACAATTCAGCTC TTATGTCCCGATTCACGA-TAAGCCGCGATAATGCGAAGAATAGTCTGTAC CTGCAAATGAATAGTCTCAGGGCTGAAGA-TACTGCTGTGTATTACTGCGC GAGAGATCATAGA-GACGCAATGGATTAT-TGGGGTCAGGGCACCTTGGTCA CTGTGAGTTCAGGGAGTA-CAAGCGGCTCTGGCAAGCCAGGAAGTGGAGA AGGATCAACCAAGGGCGATATA-CAAATGACACAATCTCCGTCATCACTTA GCG-CATCAGTCGGGACAGAGTCACTAT-TACGTGTACTGCCAGCTTGTCT GTTAGTTCCACTTATCTC-CACTGGTATCAGCAAAAACCAGGGAAAGCTCC TAAGCTTCTGATATACAGTACTT-CAAATCTCGCGTCCGGCGTCCCCTCCCG ATTCTCAGGAAGCGGCAGCGGGACAGACTT-CACTTTGACCATCAGCAGCC TCCAACCTGAGGAT-TTTGCGACTTATTACTGCCACCAATAC-CATCGGTCTC CACTCACCTTTGGCGGAGGTACTAAAGTAGAAAT-CAAG (SEQ ID NO:7), or a fragment or variant thereof encoding a polypeptide able to bind IL13Ra2.

In some cases, the anti-IL13Ra2 scFv is encoded by the nucleic acid sequence
ATGGTTCTCCTCGT-CACGAGCCTTTTGCTCTGCGAGCTTCCG-CATCCCGCA TTTCTGCTCATACCCGAGGTA-CAGCTGGTAGAGAGTGGAGGCGGATTGGT CCAGCCGGGGGGCTCCCTTA-GACTCAGTTGTGCTGCAAGTGGGTTTACCTT CACTAAATATGGCGTTCACTGGGT-GAGGCAGGCACCCGGAAAGGGGTTGG AGTGGGTAGCAGTCAAATGGGCTGGGGGCTCTA-CAGATTACAACAGTGCA CTGATGTCAAGATTCAC-GATTAGCCGAGACAATGCTAAGAATTCATTGTA TCTCCAGATGAATTCACTTAGGGCCGAA-GACACTGCCGTTTATTATTGTGC TAGAGAT-CATCGGGACGCTATGGATTAT-TGGGGACAAGGCACTCTTGTAA CTGTAAGTTCCGGTTCTACGTCTGGTTCAG-GAAAGCCGGGAAGCGGCGAA GGTTCTAC-CAAAGGAGACATACAGATGACCCAGT-CACCCTCCAGTCTTTC CGCCAGCGTAGGAGACCGGGTAACAATTA-CATGCACAGCATCCTTGTCTG TGTCCAGCACT-TACCTGCATTGGTATCAACAGAAGCCGGG-GAAGGCACCC AAACTGCTTATCTACTC-CACGTCTAACCTTGCGTCAGGCGTCCCGAGTAGG TTCAGCGGGTCCGGCAGTGGGACGGACTTTACCCT-CACTATAAGTTCACT GCAACCCGAA-GACTTTGCGACATACTATTGCCATCAGTAT-CATCGGTCTCC TTTGACATTTGGTGGGGGCACAAAGGTG-GAAATAAAGGCGGCCGCTCGCG CACT (SEQ ID NO:8), or a fragment or variant thereof encoding a polypeptide able to bind IL13Ra2.

In some embodiments, the disclosed CAR comprises a hinge and/or transmembrane domain derived from CD8. For example, the CAR can comprise the amino acid sequence (SEQ ID NO: 9)
FVPVFLPAKPTTTPAPRPPTPAPTIASQPLSLRPEACRPAAGGAVHTRGL

DFACDIYIWAPLAGTCGVLLLSLVITLYCNHRNR.

In some embodiments, the disclosed CAR comprises a hinge and/or transmembrane domain derived from CD28. For example, the CAR can comprise the amino acid sequence (SEQ ID NO: 10)
VMYPPPYLDNEKSNGTIIHVKGKHLCPSPLFPGPSKPFWVLVVVGGVLAC

YSLLVTVAFIIFWV.

In some embodiments, the disclosed CAR comprises a costimulatory domain derived from CD28. For example, the CAR can comprise the amino acid sequence RSKRSRLLHSDYMNMTPRRPGPTRKHYQPYAPPRD-FAAYRS (SEQ ID NO:11).

In some embodiments, the disclosed CAR comprises a costimulatory domain derived from 4-1BB. For example, the CAR can comprise the amino acid sequence (SEQ ID NO: 12)
RFSVVKRGRKKLLYIFKQPFMRPVQTTQEEDGCSCRFPEEEEGGCEL.

In some embodiments, the disclosed CAR comprises an intracellular signaling domain derived from CD3 zeta (CD3ζ). For example, the CAR can comprise the amino acid sequence (SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

In some embodiments, the disclosed CAR comprises a linker between the $V_H$ and $V_L$ domains having the amino acid sequence GSTSGSGKPGSGEGSTKG (SEQ ID NO:14).

In some embodiments, the disclosed CAR comprises a signal peptide having the amino acid sequence MVLLVTSLLLCELPHPAFLLIP (SEQ ID NO:15).

In some embodiments, the anti-IL13Ra2 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target IL13Ra2 and at least one additional tumor antigen. Tumor antigens are proteins that are produced by tumor cells that elicit an immune response, particularly T-cell mediated immune responses. The additional antigen binding domain can be an antibody, or a natural ligand of the tumor antigen, or a molecule that recognizes peptides derived from the tumor antigen presented by MHC molecules. The selection of the additional antigen binding domain will depend on the particular type of cancer to be treated. Tumor antigens are well known in the art and include, for example, a glioma-associated antigen, carcinoembryonic antigen (CEA), EGFRvIII, IL-11Ra, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin B1, lectin-reactive AFP, Fos-related antigen 1, ADRB3, thyroglobulin, EphA2, RAGE-1, RU1, RU2, SSX2, AKAP-4, LCK, OY-TES1, PAX5, SART3, CLL-1, fucosyl GM1, GloboH, MN-CA IX, EPCAM, EVT6-AML, TGS5, human telomerase reverse transcriptase, plysialic acid, PLAC1, RU1, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-1a, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRCSD, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUC1, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, IL13Ra2, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed IL13Ra2-specific CARs that allow expression of the IL13Ra2-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors. In one aspect, the viral vector is a murine stem cell-based γ-retroviral vector (MSGV1). Accordingly, disclosed herein are viral vectors (such as, for example an MSGV1 vector) comprising any of the nucleic acids disclosed herein.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+ T lymphocytes. In some embodiments, the T cells comprise γδ T cells, which possess a distinct T-cell receptor (TCR) having one γ chain and one δ chain instead of α and β chains.

Natural-killer (NK) cells are CD56+CD3− large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against IL13Ra2-expressing cancer cells. Accordingly, in one aspect, disclosed herein are methods of providing an anti-tumor immune response against IL13Ra2-expressing cancer cells. In other words, disclosed herein are methods of providing an anti-tumor immune response in a subject with an IL13Ra2-expressing cancer, the method comprising administering to the subject an effective amount of an immune effector cell genetically modified to express the CAR polypeptides disclosed herien, thereby providing an anti-tumor immunity in the mammal. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to IL13Ra2.

Adoptive transfer of immune effector cells expressing chimeric antigen receptors is a promising anti-cancer therapeutic. Following the collection of a patient's immune effector cells, the cells may be genetically engineered to express the disclosed IL13Ra2-specific CARs, then infused back into the patient.

As noted above, the CARs disclosed herein can elicit an anti-tumor immune response against IL13Ra2-expressing cancer cells thereby treating, inhibiting, or otherwise reducing the cancer. Accordingly, in one aspect, disclosed herein are methods of treating/inhibiting, and/or reducing a IL-13Ra2 expressing cancer or metastasis of an IL-13Ra2-expressing cancer or the proliferation of an IL-13Ra2-expressing cancer in a subject comprising administering to the subject any of the CARs disclosed herein.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodimetns formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any IL13Ra2-expressing cell in a subject undergoing unregulated growth, invasion, or metastasis. Cancers that express IL13Ra2 include prostate cancer, ovarian cancer, adenocarcinoma of the lung, breast cancer, endometrial cancer, gastric cancer, colon cancer, and pancreatic cancer. IL13Ra2 has also been found on Jurkat cells. In some aspects, the cancer is a gallbladder cancer, exocrine adenocarcinoma, or apocrine adenocarcinomas.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma (including melanoma brain metastases), squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. Accordingly, in one aspect, disclosed herein are methods of providing an anti-tumor immune response against IL13Ra2-expressing cancer cells and/or treating/inhibiting, and/or reducing a IL-13Ra2 expressing cancer or metastasis of an IL-13Ra2-expressing cancer or the proliferation of an IL-13Ra2-expressing cancer in a subject comprising administering to the subject any of the CARs disclosed herein; wherein the cancer is a melanoma (including melanoma brain metastases).

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM 1 or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-1a from the human CXC and C—C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC tag, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid subsitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, inhibiting and/or reducing the intensity or frequency of one or more a diseases or conditions, a symptom of a disease or condition, or an underlying cause of a disease or condition. Treatments provided herein are not limited to complete ablation of a disease or a condition (such as, for example, a cancer), but can include reductions in the disease, condition, or symptoms associated therewith including a 5%, 6%, 7%, 8%, 9%, 10%, 20%, 30%, 40%, 50%, 60%, 70%, 80%, 90%, 95%, 96%, 97%, 98%, 99% or great reduction in the disease, conditions, or symptoms. In one aspect, the treatment can refer to the inhbitiion of metastasis of a cancer or reduction in cancer proliferation rate rather than simply a reduction in tumor volume. Accordingly, a treatment that inhibits metastasis or reduces the rate of cancer proliferation relative to untreated controls is considered a treatment of the cancer even if tumor volume does not decrease. Treatments according to the invention may be applied preventively, prophylactically, pallatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1

A thorough gene-expression study of 59 melanoma metastases showed that multiple CTA were significantly overexpressed in a relevant proportion of melanoma specimens. The detailed description of the methods can be found in (Beard R E, et al. Clin Cancer Res. 2013 19(18):4941-50).

Figure 2:
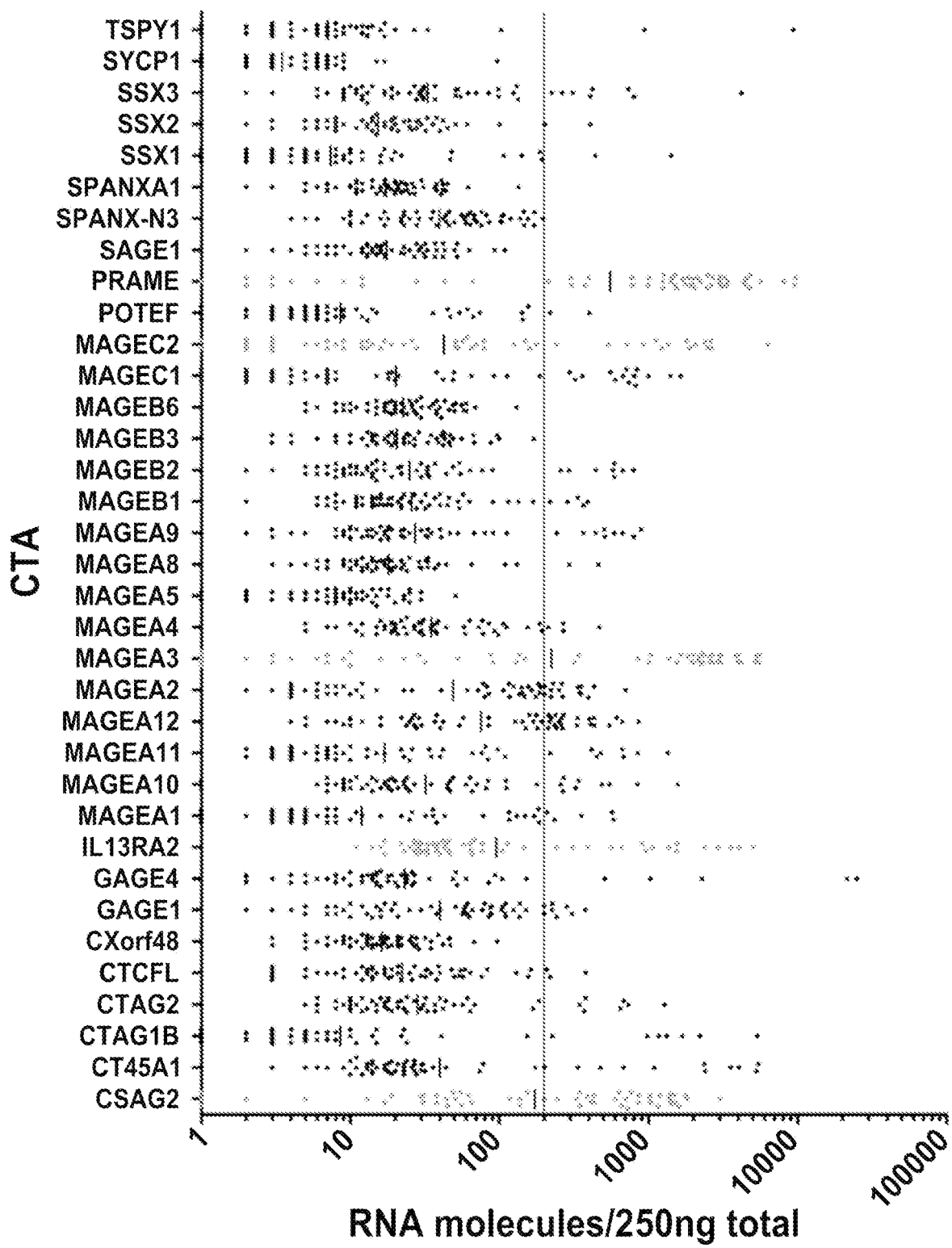
FIG. 2 shows RNA expression of 35 cancer/testis antigens (CTAs), represented as counts of target mRNA in 250 ng of total RNA, in melanoma metastases.
Figure 3:
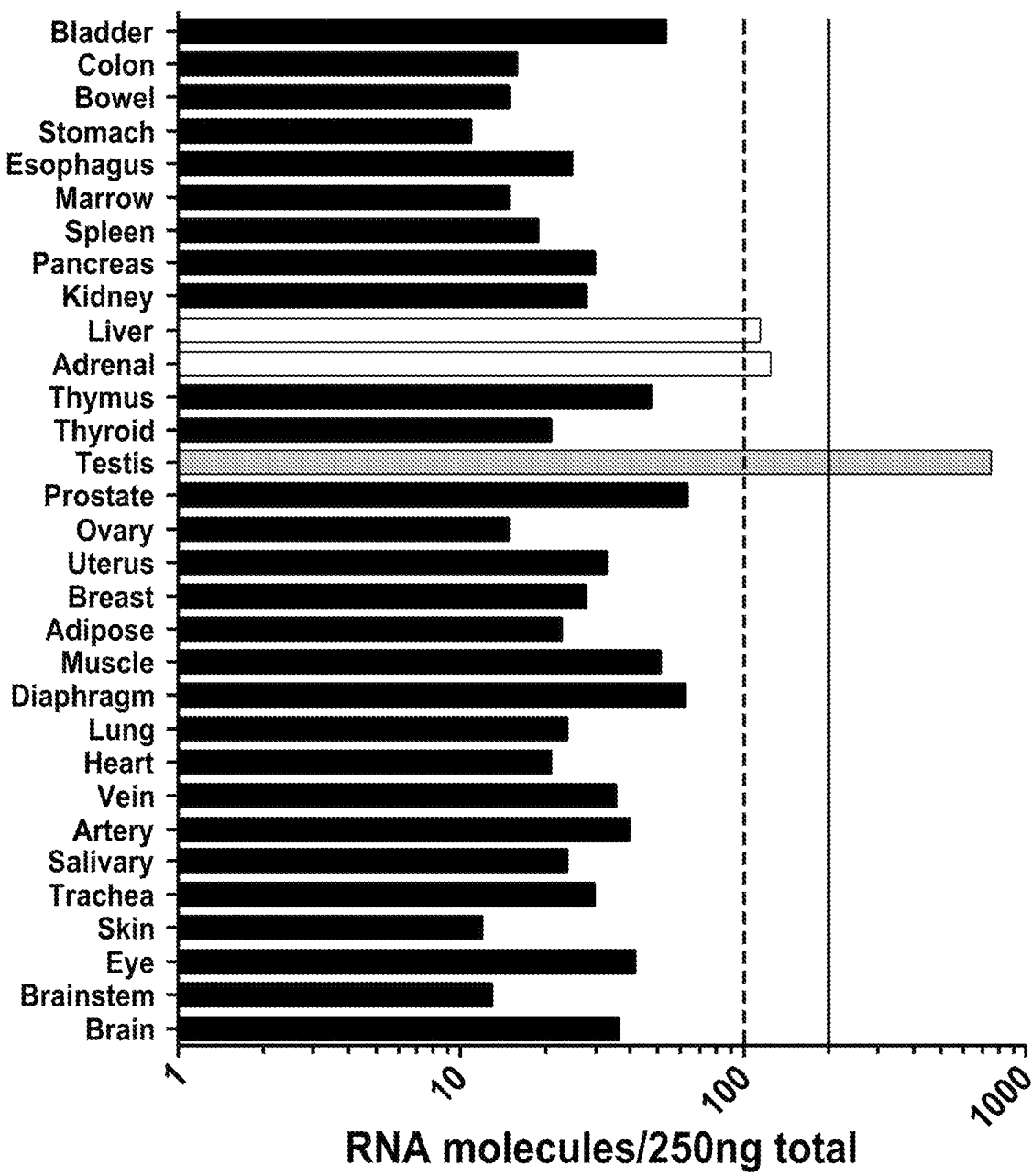
FIG. 3 shows expression of IL13RA2 in normal tissues.

Briefly, flash frozen surgically resected lesions, collected at the Surgery Branch of NCI, were homogenized and total RNA was purified using a commercial column-based kit. The expression of 97 genes (including internal reference genes) was assessed simultaneously by NanoString and normalized using the reference genes. FIG. 2 shows the results for the expression of 35 CTA, represented as counts of target mRNA in 250 ng of total RNA, each dot corresponding to one tumor sample. The expression level capable of inducing specific production of IFNgamma by TCR-transduced PBL in vitro was determined to be 200 copies (vertical line). Any expression value below 200 copies was not biologically relevant. Expression results for IL13RA2 WAS positive above 200 counts in at least 20% of the samples. The expression of each of IL13RA2 in normal tissues is shown in FIG. 3.

Example 2

CARs expressed in human primary T cells that recognize IL 13Ra2-expressing melanoma cells were designed.

Hu08-H2L
(SEQ ID NO: 5)
MVLLVTSLLLCELPHPAFLLIPEVQLVESGGGLVQPGGSLRLSCAASGF
TFSRNGMSWVRQAPGKGLEWVATVSSGGSYIYYADSVKGRFTISRDNAK
NSLYLQMNSLRAEDTAVYYCARQGTTALATRFFDVWGQGTLVTVSSGST
SGSGKPGSGEGSTKGDIQMTQSPSSLSASVGDRVTITCKASQDVGTAVA
WYQQKPGKAPKLLIYSASYRSTGVPSRFSGSGSGTDFTLTISSLQPEDF
ATYYCQHHYSAPWTFGGGTKVEIK

Hu07-H2L
(SEQ ID NO: 6)
MVLLVTSLLLCELPHPAFLLIPEVQLVESGGGLVQPGGSLRLSCAASGF
TFTKYGVHWVRQAPGKGLEWVAVKWAGGSTDYNSALMSRFTISRDNAKN
SLYLQMNSLRAEDTAVYYCARDHRDAMDYWGQGTLVTVSSGSTSGSGKP
GSGEGSTKGDIQMTQSPSSLSASVGDRVTITCTASLSVSSTYLHWYQQK
PGKAPKLLIYSTSNLASGVPSRFSGSGSGTDFTLTISSLQPEDFATYYC
HQYHRSPLTFGGGTKVEIK

Hu08-L2H
(SEQ ID NO: 16)
MVLLVTSLLLCELPHPAFLLIPDIQMTQSPSSLSASVGDRVTITCKASQ
DVGTAVAWYQQKPGKAPKLLIYSASYRSTGVPSRFSGSGSGTDFTLTIS
SLQPEDFATYYCQHHYSAPWTFGGGTKVEIKGSTSGSGKPGSGEGSTKG
EVQLVESGGGLVQPGGSLRLSCAASGFTFTKYGVHWVRQAPGKGLEWVA
VKWAGGSTDYNSALMSRFTISRDNAKNSLYLQMNSLRAEDTAVYYCARD
HRDAMDYWGQGTLVTVSS

Figure 4:
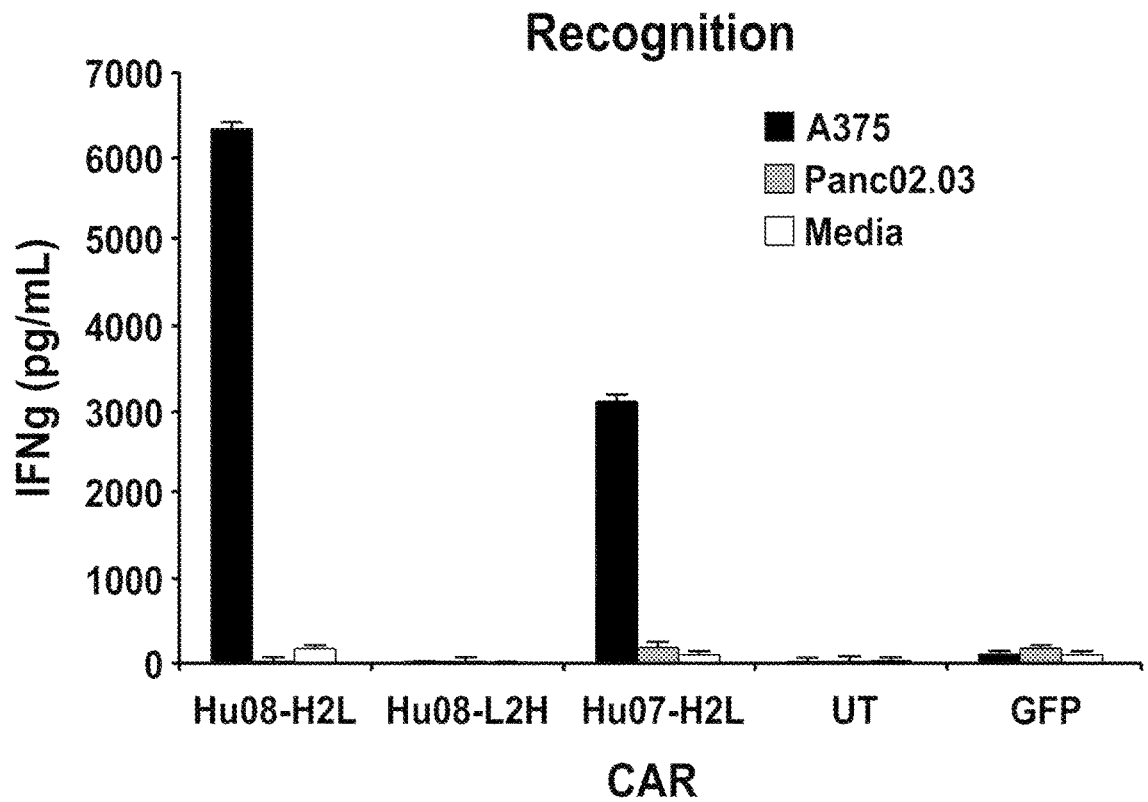
FIG. 4 is a bar graph showing IFNγ (pg/ml) levels in A375 cells contacted with Hu07H2L, Hu08H2L, and Hu08-L2H CARs. Hu08-L2H did not recognize A375 cells.
Figure 5:
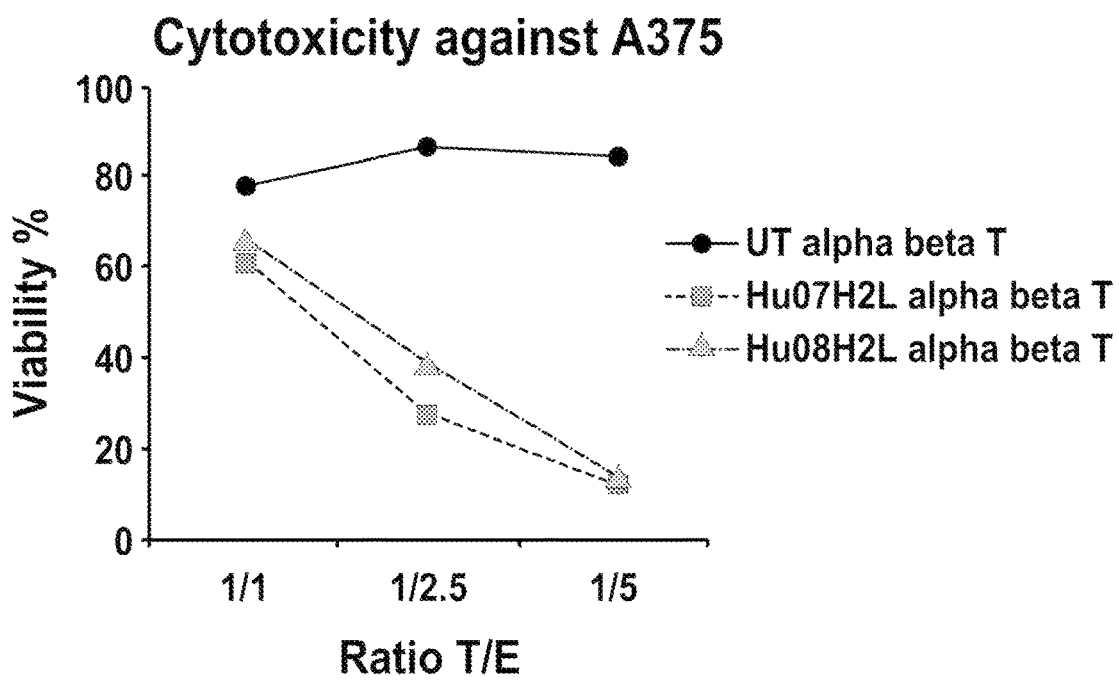
FIG. 5 shows cytotoxicity of Hu07H2L and Hu08H2L CAR-T cells against A375 cells compared to a control.

FIG. 4 is a bar graph showing IFNγ (pg/ml) levels in A375 cells contacted with Hu07H2L, Hu08H2L, and Hu08-L2H CARs. Hu08-L2H did not recognize A375 cells. FIG. 5 shows cytotoxicity of Hu07H2L and Hu08H2L CAR-T cells against A375 cells compared to a control.

Figure 6A:
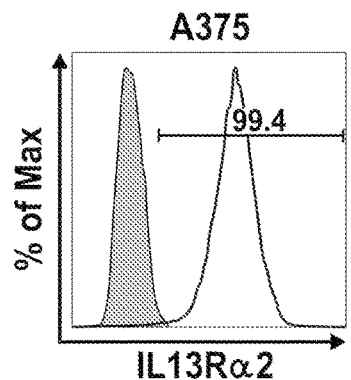
FIGS. 6A, 6B, and 6C show real-time analysis of CAR-T cell-induced cytotoxicity.
Figure 6B:
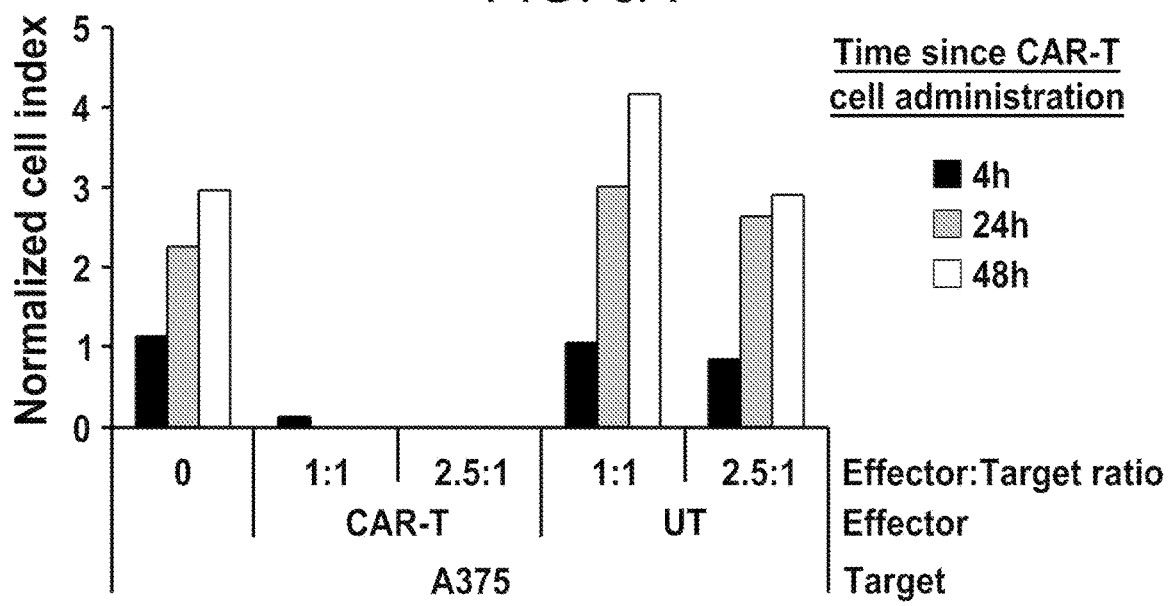
Figure 6C:
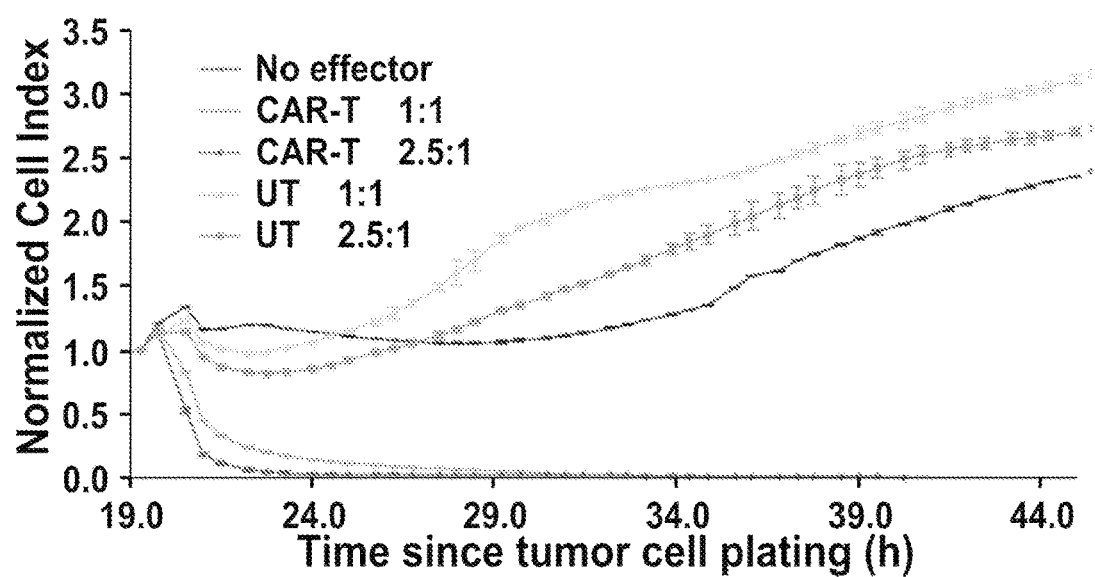

CAR-Ts produced high levels of interferon-gamma (IFNγ) when co-cultured with IL13Rα2-expressing melanoma cells, such as A375. Both CAR-T constructs exhibited a potent cytotoxic capacity, resulting in less than 20% viability in A375 cells. Real-time assessment of CAR-induced cytotoxicity showed that tumor cell destruction occurs rapidly, resulting in greater than 80% reduction in viability after 4 hours in co-culture, at a ratio of 1 CAR-T cell per tumor cell (FIG. 6). The expression of IL13RA2 on the surface of A375 melanoma cells was analyzed by flow cytometry (FIG. 6A). A375 cells were seeded in an xCELLigence E-plate, and their growth was monitored over time based on the changes in the impedance of the plate resulting from the adherence of tumor cells. After approximately 20 hours, anti-IL13RA2 Hu08-HL CAR-T cells (CAR-T) or control untransduced T cells (UT) were added at the indicated ratios. The viability of viable tumor cells over time was estimated based on the fraction of adherent cells, and expressed in a relative unit (Normalized Cell Index). A normalized cell index of 1 corresponds to the amount of adherent tumor cells at the moment when T cells were added to the culture. Error bars represent standard deviation of replicates (FIG. 6B). Next, a bar graph depicting, the normalized cell index at 4, 24, and 48 hours post CAR-T cell administration for the indicated ratios was created.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising an IL13Ra2 antigen binding domain, a transmembrane domain, an intracellular signaling domain, and a co-stimulatory signaling region; wherein the IL13Ra2 antigen binding domain is single chain variable fragment that specifically binds IL13Ra2 comprising a variable heavy (VH) domain as set forth in SEQ ID NO: 2 and a variable light (VL) domain as set forth in SEQ ID NO: 4.

2. The polypeptide of claim 1, wherein the anti-IL13Ra2 scFv comprises an amino acid sequence SEQ ID NO:6.

3. The polypeptide of claim 1, wherein the costimulatory signaling region comprises the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

4. The polypeptide of claim 1, wherein the CAR polypeptide is defined by the formula:

SP-IL13Ra2-HG-TM-CSR-ISD; or

SP-IL13Ra2-HG-TM-ISD-CSR wherein "SP" represents a signal peptide,
wherein "IL13Ra2" represents a IL13Ra2-binding region,
wherein "HG" represents and optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

5. The polypeptide of claim 1, wherein the intracellular signaling domain comprises a CD3 zeta (CD3ζ) signaling domain.

6. An isolated nucleic acid sequence encoding the recombinant polypeptide of claim 1.

7. A vector comprising the isolated nucleic acid sequence of claim 6.

8. The vector of claim 7, wherein the vector is a MSGV1 retroviral vector.

9. A cell comprising the vector of claim 7.

10. The cell of claim 9, wherein the cell is selected from the group consisting of an αβT cell, γδT cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

11. The cell of claim 9, wherein the cell exhibits an anti-tumor immunity when the antigen binding domain of the CAR binds to IL13Ra2.

12. A method of providing an anti-tumor immunity in a subject with an IL13Ra2-expressing cancer, the method comprising administering to the subject an effective amount of an immune effector cell genetically modified to express the CAR polypeptide of claim 1, thereby providing an anti-tumor immunity in the mammal.

13. The method of claim 12, wherein the immune effector cell is selected from the group consisting of a T cell, a Natural Killer (NK) cell, a cytotoxic T lymphocyte (CTL), and a regulatory T cell.

14. A chimeric antigen receptor (CAR) polypeptide, comprising an IL13Ra2 antigen binding domain, a transmembrane domain, an intracellular signaling domain, and a co-stimulatory signaling region; wherein the IL13Ra2 antigen binding domain is single chain variable fragment that specifically binds IL13Ra2 comprising a variable heavy (VH) domain comprising a complementarity determining region (CDR) 1 (CDR1), CDR2, and CDR3 as set forth in SEQ ID NOs: 16, 17, and 18, respectively; and a variable light (VL) domain comprising a CDR1, CDR2, and CDR3 as set forth in SEQ ID NOs: 19, 20, and 21, respectively.

* * * * *

SEQUENCE LISTING

<160> NUMBER OF SEQ ID NOS: 41

<210> SEQ ID NO 1
<211> LENGTH: 122
<212> TYPE: PRT
<213> ORGANISM: Artificial Sequence
<220> FEATURE:
<223> OTHER INFORMATION: Synthethic constructs

<400> SEQUENCE: 1

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
            115                 120

<210> SEQ ID NO 2
<211> LENGTH: 116
<212> TYPE: PRT
<213> ORGANISM: Artificial Sequence
<220> FEATURE:
<223> OTHER INFORMATION: Syntethic constructs

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
            115

<210> SEQ ID NO 3
<211> LENGTH: 107
<212> TYPE: PRT
<213> ORGANISM: Artificial Sequence
<220> FEATURE:
<223> OTHER INFORMATION: Syntethic constructs

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105

<210> SEQ ID NO 4
<211> LENGTH: 109
<212> TYPE: PRT
<213> ORGANISM: Artificial Sequence
<220> FEATURE:
<223> OTHER INFORMATION: Syntethic constructs

<400> SEQUENCE: 4

Asp Asp Ile Gln Met Thr Gln Ser Pro Ser Ser Leu Ser Ala Ser Val
1               5                   10                  15

Gly Asp Arg Val Thr Ile Thr Cys Thr Ala Ser Leu Ser Val Ser Ser
            20                  25                  30

Thr Tyr Leu His Trp Tyr Gln Gln Lys Pro Gly Lys Ala Pro Lys Leu
        35                  40                  45

Leu Ile Tyr Ser Thr Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys His Gln Tyr His Arg Ser
                85                  90                  95

Pro Leu Thr Phe Gly Gly Gly Thr Lys Val Glu Ile Lys
            100                 105

<210> SEQ ID NO 5
<211> LENGTH: 269
<212> TYPE: PRT
<213> ORGANISM: Artificial Sequence
<220> FEATURE:
<223> OTHER INFORMATION: Syntethic constructs

<400> SEQUENCE: 5

Met Val Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Arg Asn Gly Met Ser Trp Val Arg Gln Ala Pro Gly
    50                  55                  60

Lys Gly Leu Glu Trp Val Ala Thr Val Ser Ser Gly Gly Ser Tyr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Gln Gly Thr Thr Ala Leu Ala Thr
        115                 120                 125

Arg Phe Phe Asp Val Trp Gly Gln Gly Thr Leu Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Asp Ile Gln Met Thr Gln Ser Pro Ser Ser Leu Ser Ala Ser
```

```
                      165                 170                 175
Val Gly Asp Arg Val Thr Ile Thr Cys Lys Ala Ser Gln Asp Val Gly
            180                 185                 190

Thr Ala Val Ala Trp Tyr Gln Gln Lys Pro Gly Lys Ala Pro Lys Leu
        195                 200                 205

Leu Ile Tyr Ser Ala Ser Tyr Arg Ser Thr Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln His His Tyr Ser Ala
                245                 250                 255

Pro Trp Thr Phe Gly Gly Gly Thr Lys Val Glu Ile Lys
                260                 265

<210> SEQ ID NO 6
<211> LENGTH: 264
<212> TYPE: PRT
<213> ORGANISM: Artificial Sequence
<220> FEATURE:
<223> OTHER INFORMATION: Syntethic constructs

<400> SEQUENCE: 6

Met Val Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Thr Lys Tyr Gly Val His Trp Val Arg Gln Ala Pro Gly
    50                  55                  60

Lys Gly Leu Glu Trp Val Ala Val Lys Trp Ala Gly Gly Ser Thr Asp
65                  70                  75                  80

Tyr Asn Ser Ala Leu Met Ser Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Asp His Arg Asp Ala Met Asp Tyr Trp
        115                 120                 125

Gly Gln Gly Thr Leu Val Thr Val Ser Ser Gly Ser Thr Ser Gly Ser
    130                 135                 140

Gly Lys Pro Gly Ser Gly Glu Gly Ser Thr Lys Gly Asp Ile Gln Met
145                 150                 155                 160

Thr Gln Ser Pro Ser Ser Leu Ser Ala Ser Val Gly Asp Arg Val Thr
                165                 170                 175

Ile Thr Cys Thr Ala Ser Leu Ser Val Ser Ser Thr Tyr Leu His Trp
            180                 185                 190

Tyr Gln Gln Lys Pro Gly Lys Ala Pro Lys Leu Leu Ile Tyr Ser Thr
        195                 200                 205

Ser Asn Leu Ala Ser Gly Val Pro Ser Arg Phe Ser Gly Ser Gly Ser
    210                 215                 220

Gly Thr Asp Phe Thr Leu Thr Ile Ser Ser Leu Gln Pro Glu Asp Phe
225                 230                 235                 240

Ala Thr Tyr Tyr Cys His Gln Tyr His Arg Ser Pro Leu Thr Phe Gly
                245                 250                 255

Gly Gly Thr Lys Val Glu Ile Lys
            260
```

<210> SEQ ID NO 7
<211> LENGTH: 792
<212> TYPE: DNA
<213> ORGANISM: Artificial Sequence
<220> FEATURE:
<223> OTHER INFORMATION: Syntethic constructs

<400> SEQUENCE: 7

```
atggtgttgc ttgtgacatc tctgctgttg tgcgagctcc cgcacccagc gtttctgctc    60
atcccagaag ttcaactggt tgaaagtggc ggcggcttgg ttcagcccgg tgggtctttg   120
cgattgagtt gcgccgccag tggttttaca ttcacaaaat atggagttca ctgggtacga   180
caagcgcctg gcaagggcct tgaatgggta gcagtcaagt gggctggggg ttcaacagat   240
tacaattcag ctcttatgtc ccgattcacg ataagccgcg ataatgcgaa gaatagtctg   300
tacctgcaaa tgaatagtct cagggctgaa gatactgctg tgtattactg cgcgagagat   360
catagagacg caatggatta ttggggtcag ggcaccttgg tcactgtgag ttcagggagt   420
acaagcggct ctggcaagcc aggaagtgga gaaggatcaa ccaagggcga tatacaaatg   480
acacaatctc cgtcatcact tagcgcatca gtcggggaca gagtcactat tacgtgtact   540
gccagcttgt ctgttagttc acttatctc cactggtatc agcaaaaacc agggaaagct   600
cctaagcttc tgatatacag tacttcaaat ctcgcgtccg gcgtcccctc ccgattctca   660
ggaagcggca gcgggacaga cttcactttg accatcagca gcctccaacc tgaggatttt   720
gcgacttatt actgccacca ataccatcgg tctccactca cctttggcgg aggtactaaa   780
gtagaaatca ag                                                       792
```

<210> SEQ ID NO 8
<211> LENGTH: 809
<212> TYPE: DNA
<213> ORGANISM: Artificial Sequence
<220> FEATURE:
<223> OTHER INFORMATION: Syntethic constructs

<400> SEQUENCE: 8

```
atggttctcc tcgtcacgag ccttttgctc tgcgagcttc cgcatcccgc atttctgctc    60
atacccgagg tacagctggt agagagtgga ggcggattgg tccagccggg gggctccctt   120
agactcagtt gtgctgcaag tgggtttacc ttcactaaat atggcgttca ctgggtgagg   180
caggcacccg gaaagggggtt ggagtgggta gcagtcaaat gggctggggg ctctacagat   240
tacaacagtg cactgatgtc aagattcacg attagccgag acaatgctaa gaattcattg   300
tatctccaga tgaattcact tagggccgaa gacactgccg tttattattg tgctagagat   360
catcgggacg ctatggatta ttggggacaa ggcactcttg taactgtaag ttccggttct   420
acgtctggtt caggaaagcc gggaagcggc gaaggttcta ccaaggagac atacagatg    480
acccagtcac cctccagtct ttccgccagc gtaggagacc gggtaacaat tacatgcaca   540
gcatccttgt ctgtgtccag cacttacctg cattggtatc aacagaagcc ggggaaggca   600
cccaaactgc ttatctactc cacgtctaac cttgcgtcag gcgtcccgag taggttcagc   660
gggtccggca gtgggacgga ctttacccctc actataagtt cactgcaacc cgaagacttt   720
gcgacatact attgccatca gtatcatcgg tctcctttga catttggtgg gggcacaaag   780
gtggaaataa aggcggccgc tcgcgcact                                     809
```

-continued

```
<210> SEQ ID NO 9
<211> LENGTH: 84
<212> TYPE: PRT
<213> ORGANISM: Artificial Sequence
<220> FEATURE:
<223> OTHER INFORMATION: Syntethic constructs

<400> SEQUENCE: 9
```

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

```
<210> SEQ ID NO 10
<211> LENGTH: 64
<212> TYPE: PRT
<213> ORGANISM: Artificial Sequence
<220> FEATURE:
<223> OTHER INFORMATION: Syntethic constructs

<400> SEQUENCE: 10
```

Val Met Tyr Pro Pro Pro Tyr Leu Asp Asn Glu Lys Ser Asn Gly Thr
1               5                   10                  15

Ile Ile His Val Lys Gly Lys His Leu Cys Pro Ser Pro Leu Phe Pro
            20                  25                  30

Gly Pro Ser Lys Pro Phe Trp Val Leu Val Val Val Gly Gly Val Leu
        35                  40                  45

Ala Cys Tyr Ser Leu Leu Val Thr Val Ala Phe Ile Ile Phe Trp Val
    50                  55                  60

```
<210> SEQ ID NO 11
<211> LENGTH: 41
<212> TYPE: PRT
<213> ORGANISM: Artificial Sequence
<220> FEATURE:
<223> OTHER INFORMATION: Syntethic constructs

<400> SEQUENCE: 11
```

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

```
<210> SEQ ID NO 12
<211> LENGTH: 47
<212> TYPE: PRT
<213> ORGANISM: Artificial Sequence
<220> FEATURE:
<223> OTHER INFORMATION: Syntethic constructs

<400> SEQUENCE: 12
```

Arg Phe Ser Val Val Lys Arg Gly Arg Lys Lys Leu Leu Tyr Ile Phe
1               5                   10                  15

```
Lys Gln Pro Phe Met Arg Pro Val Gln Thr Thr Gln Glu Glu Asp Gly
            20                  25                  30

Cys Ser Cys Arg Phe Pro Glu Glu Glu Gly Gly Cys Glu Leu
        35                  40                  45

<210> SEQ ID NO 13
<211> LENGTH: 112
<212> TYPE: PRT
<213> ORGANISM: Artificial Sequence
<220> FEATURE:
<223> OTHER INFORMATION: Syntethic constructs

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 18
<212> TYPE: PRT
<213> ORGANISM: Artificial Sequence
<220> FEATURE:
<223> OTHER INFORMATION: Syntethic constructs

<400> SEQUENCE: 14

Gly Ser Thr Ser Gly Ser Gly Lys Pro Gly Ser Gly Glu Gly Ser Thr
1               5                   10                  15

Lys Gly

<210> SEQ ID NO 15
<211> LENGTH: 22
<212> TYPE: PRT
<213> ORGANISM: Artificial Sequence
<220> FEATURE:
<223> OTHER INFORMATION: Syntethic constructs

<400> SEQUENCE: 15

Met Val Leu Leu Val Thr Ser Leu Leu Leu Cys Glu Leu Pro His Pro
1               5                   10                  15

Ala Phe Leu Leu Ile Pro
            20

<210> SEQ ID NO 16
<211> LENGTH: 6
<212> TYPE: PRT
<213> ORGANISM: Artificial Sequence
<220> FEATURE:
<223> OTHER INFORMATION: Syntethic constructs

<400> SEQUENCE: 16
```

```
Thr Lys Tyr Gly Val His
1               5

<210> SEQ ID NO 17
<211> LENGTH: 16
<212> TYPE: PRT
<213> ORGANISM: Artificial Sequence
<220> FEATURE:
<223> OTHER INFORMATION: Syntethic constructs

<400> SEQUENCE: 17

Val Lys Trp Ala Gly Gly Ser Thr Asp Tyr Asn Ser Ala Leu Met Ser
1               5                   10                  15

<210> SEQ ID NO 18
<211> LENGTH: 8
<212> TYPE: PRT
<213> ORGANISM: Artificial Sequence
<220> FEATURE:
<223> OTHER INFORMATION: Syntethic constructs

<400> SEQUENCE: 18

Asp His Arg Asp Ala Met Asp Tyr
1               5

<210> SEQ ID NO 19
<211> LENGTH: 12
<212> TYPE: PRT
<213> ORGANISM: Artificial Sequence
<220> FEATURE:
<223> OTHER INFORMATION: Syntethic constructs

<400> SEQUENCE: 19

Thr Ala Ser Leu Ser Val Ser Ser Thr Tyr Leu His
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Syntethic constructs

<400> SEQUENCE: 20

Ser Ala Ser Tyr Arg Ser Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Syntethic constructs

<400> SEQUENCE: 21

Gln His His Tyr Ser Ala Pro Trp Thr
1               5

<210> SEQ ID NO 22
<211> LENGTH: 6
<212> TYPE: PRT
<213> ORGANISM: Artificial Sequence
<220> FEATURE:
<223> OTHER INFORMATION: Syntethic constructs

<400> SEQUENCE: 22

Ser Arg Asn Gly Met Ser
```

```
<210> SEQ ID NO 23
<211> LENGTH: 17
<212> TYPE: PRT
<213> ORGANISM: Artificial Sequence
<220> FEATURE:
<223> OTHER INFORMATION: Syntethic constructs

<400> SEQUENCE: 23

Thr Val Ser Ser Gly Gly Ser Tyr Ile Tyr Tyr Ala Asp Ser Val Lys
1               5                   10                  15
Gly

<210> SEQ ID NO 24
<211> LENGTH: 13
<212> TYPE: PRT
<213> ORGANISM: Artificial Sequence
<220> FEATURE:
<223> OTHER INFORMATION: Syntethic constructs

<400> SEQUENCE: 24

Gln Gly Thr Thr Ala Leu Ala Thr Arg Phe Phe Asp Val
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Syntethic constructs

<400> SEQUENCE: 25

Lys Ala Ser Gln Asp Val Gly Thr Ala Val Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Syntethic constructs

<400> SEQUENCE: 26

Ser Ala Ser Tyr Arg Ser Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Syntethic constructs

<400> SEQUENCE: 27

Gln His His Tyr Ser Ala Pro Trp Thr
1               5

<210> SEQ ID NO 28
<211> LENGTH: 122
<212> TYPE: PRT
<213> ORGANISM: Artificial Sequence
<220> FEATURE:
<223> OTHER INFORMATION: Syntethic constructs

<400> SEQUENCE: 28
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Thr Pro Asp Lys Arg Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
            115                 120
```

<210> SEQ ID NO 29
<211> LENGTH: 107
<212> TYPE: PRT
<213> ORGANISM: Artificial Sequence
<220> FEATURE:
<223> OTHER INFORMATION: Syntethic constructs

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Ile Pro Gly Lys Ala Pro Lys Leu Leu Ile
        35                  40                  45

Tyr Ser Ala Ser Tyr Arg Ser Thr Gly Val Pro Asp Arg Phe Ser Gly
    50                  55                  60

Ser Gly Ser Gly Thr Asp Phe Ser Phe Leu Leu Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105
```

<210> SEQ ID NO 30
<211> LENGTH: 116
<212> TYPE: PRT
<213> ORGANISM: Artificial Sequence
<220> FEATURE:
<223> OTHER INFORMATION: Syntethic constructs

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Lys Asp Asn Ala Lys Asn Ser Leu Tyr Leu
65                  70                  75                  80
```

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Syntethic constructs

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Lys Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Syntethic constructs

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115

```
<210> SEQ ID NO 33
<211> LENGTH: 116
<212> TYPE: PRT
<213> ORGANISM: Artificial Sequence
<220> FEATURE:
<223> OTHER INFORMATION: Syntethic constructs

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Lys Tyr
            20                  25                  30

Gly Val His Trp Val Arg Gln Ala Pro Gly Lys Gly Leu Glu Trp Val
        35                  40                  45

Gly Val Lys Trp Ala Gly Gly Ser Thr Asp Tyr Asn Ser Ala Leu Met
    50                  55                  60

Ser Arg Phe Thr Ile Ser Lys Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: Syntethic constructs

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Ile Pro Gly Lys Ala Pro Lys Leu Leu Ile
        35                  40                  45

Tyr Ser Ala Ser Tyr Arg Ser Thr Gly Val Pro Asp Arg Phe Ser Gly
    50                  55                  60

Ser Gly Ser Gly Thr Asp Phe Ser Phe Leu Leu Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105

<210> SEQ ID NO 35
<211> LENGTH: 108
<212> TYPE: PRT
<213> ORGANISM: Artificial Sequence
<220> FEATURE:
<223> OTHER INFORMATION: Syntethic constructs

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Leu Ser Val Ser Ser Thr
            20                  25                  30
```

Tyr Leu His Trp Tyr Gln Gln Lys Pro Gly Ser Ser Pro Lys Leu Leu
            35                  40                  45

Ile Tyr Ser Thr Ser Asn Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 36
<211> LENGTH: 108
<212> TYPE: PRT
<213> ORGANISM: Artificial Sequence
<220> FEATURE:
<223> OTHER INFORMATION: Syntethic constructs

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Trp
            35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 37
<211> LENGTH: 108
<212> TYPE: PRT
<213> ORGANISM: Artificial Sequence
<220> FEATURE:
<223> OTHER INFORMATION: Syntethic constructs

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

```
<210> SEQ ID NO 38
<211> LENGTH: 108
<212> TYPE: PRT
<213> ORGANISM: Artificial Sequence
<220> FEATURE:
<223> OTHER INFORMATION: Syntethic constructs

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 39
<211> LENGTH: 108
<212> TYPE: PRT
<213> ORGANISM: Artificial Sequence
<220> FEATURE:
<223> OTHER INFORMATION: Syntethic constructs

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 40
<211> LENGTH: 263
<212> TYPE: PRT
<213> ORGANISM: Artificial Sequence
<220> FEATURE:
<223> OTHER INFORMATION: Syntethic constructs

<400> SEQUENCE: 40

Met Val Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45
```

Gln Asp Val Gly Thr Ala Val Ala Trp Tyr Gln Gln Lys Pro Gly Lys
 50                  55                  60

Ala Pro Lys Leu Leu Ile Tyr Ser Ala Ser Tyr Arg Ser Thr Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln His
                100                 105                 110

His Tyr Ser Ala Pro Trp Thr Phe Gly Gly Gly Thr Lys Val Glu Ile
                115                 120                 125

Lys Gly Ser Thr Ser Gly Ser Gly Lys Pro Gly Ser Gly Glu Gly Ser
130                 135                 140

Thr Lys Gly Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Thr Lys Tyr Gly Val His Trp Val Arg Gln Ala Pro Gly Lys Gly Leu
                180                 185                 190

Glu Trp Val Ala Val Lys Trp Ala Gly Gly Ser Thr Asp Tyr Asn Ser
                195                 200                 205

Ala Leu Met Ser Arg Phe Thr Ile Ser Arg Asp Asn Ala Lys Asn Ser
                210                 215                 220

Leu Tyr Leu Gln Met Asn Ser Leu Arg Ala Glu Asp Thr Ala Val Tyr
225                 230                 235                 240

Tyr Cys Ala Arg Asp His Arg Asp Ala Met Asp Tyr Trp Gly Gln Gly
                245                 250                 255

Thr Leu Val Thr Val Ser Ser
                260

<210> SEQ ID NO 41
<211> LENGTH: 108
<212> TYPE: PRT
<213> ORGANISM: Artificial Sequence
<220> FEATURE:
<223> OTHER INFORMATION: Syntethic constructs

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
                20                  25                  30

Tyr Leu His Trp Tyr Gln Gln Lys Pro Gly Ser Ser Pro Lys Leu Trp
                35                  40                  45

Ile Tyr Ser Thr Ser Asn Leu Ala Ser Gly Val Pro Ser Arg Phe Ser
            50                  55                  60

Gly Ser Gly Ser Gly Thr Ser Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
                100                 105